(12) United States Patent
Egan et al.

(10) Patent No.: US 7,056,734 B1
(45) Date of Patent: Jun. 6, 2006

(54) DIFFERENTIATION OF NON-INSULIN PRODUCING CELLS INTO INSULIN PRODUCING CELLS BY GLP-1 OR EXENDIN-4 AND USES THEREOF

(75) Inventors: Josephine Egan, Baltimore, MD (US); Riccardo Perfetti, Washington, DC (US); Antonino Passaniti, White Hall, MD (US); Nigel Greig, Silver Spring, MD (US); Harold Holloway, Middle River, MD (US); Joel Habener, Newton Centre, MA (US); Doris Stoffers, Moorestown, NJ (US)

(73) Assignee: The United States of America as represented by the Department of Health and Human Services, NIH, Washington, DC (US)

( * ) Notice: Subject to any disclaimer, the term of this patent is extended or adjusted under 35 U.S.C. 154(b) by 0 days.

(21) Appl. No.: 09/762,538

(22) PCT Filed: Aug. 10, 1999

(86) PCT No.: PCT/US99/18099

§ 371 (c)(1),
(2), (4) Date: Jul. 19, 2001

(87) PCT Pub. No.: WO00/09666

PCT Pub. Date: Feb. 24, 2000

Related U.S. Application Data

(60) Provisional application No. 60/095,917, filed on Aug. 10, 1998.

(51) Int. Cl.
*C12N 5/00* (2006.01)
(52) U.S. Cl. ...................................... 435/325; 530/308
(58) Field of Classification Search ................ 435/325; 424/93.7; 514/2, 3
See application file for complete search history.

(56) References Cited

U.S. PATENT DOCUMENTS

| 5,424,286 A | * | 6/1995 | Eng | |
| 2003/0224983 A1 | | 12/2003 | Nielsen | .................... 514/12 |

FOREIGN PATENT DOCUMENTS

| WO | WO 95/31214 | 11/1995 |
| WO | WO 99/43705 | 9/1999 |

OTHER PUBLICATIONS

Raufman et al. Truncated GLP-1 interacts with exendin receptors on dispersed acini from guinea pig pancreas. 1992. J. Biol. Chem., 267(30):21432-27.*
Shepard et al. A single amino acid change in IFN-b1 abolishes its antiviral activity. Nature, 1981, 294:563-565.*
Mashima et al. "Formation of Insulin-Production Cells from pancreatic Acinar AR42J Cells by Hepatocyte Growth Factor." *Endocrinology* 137: 3969-3976, 1996.
Gefel et al. "Glucagon-Like Peptide I Analogs: Effects on Insulin Secretin and Adenosine 3',5'-Monophosphate Formation." *Endocrinology* 126:2164-68, 1990.
De Ore et al. "The effects of GLP-1 on insulin release in young and old rats in the fasting state and during an intravenous glucose tolerance test." *J. Geront.* 52: B245-249, 1997.
Drucker et al. "Glucagon-like Peptide 1 stimulates insulin gene expression and increases cyclic AMP in a rat islet cell line." *Proc. Natl. Acad. Sci. USA.* 84: 3434-3438, 1987.
Egan et al. "Glucagon-like peptide-1 (7-36) amide (GLP-1) enhances insulin-stimulated glucose metabolism in 3T3-11 adipocytes: one of several potential extrapancreatic sites of GLP-1 action." *Endocrinology* 135: 2070-2075, 1994.
Elahi, et al. "The insulinotropic actions of glucose-dependent insulinotropic polypeptide (GIP) and glucagon-like peptide-1 (737) in normal and diabectic subjects." *Regulatory Peptides* 51: 63-74, 1994.
Elahi, et al. "The effect of age and glucose concentration on insulin secretion by the isolated perfused pancreas." *Endocrinology* 116; 11-16, 1985.
Federal Register 63, Friday, Feb. 20, 1998, p. 8652.
Fehmann and Habener et al. "Insulinotropic hormone glucagon-like peptide-1 (7-37) stimulation of proinsulin gene expression and proisulin biosysthesis in insulinoma βTC-1 cells." *Endocrinology* 130: 159-166, 1992.
Fehmann et al. "Cell and Molecular Biology of the Incretin Hormones Glucagon-Like Peptide-I and Glucose-dependent Insulin Releasing polypeptide." *Endocrine Rev.* 16:390-410, 1995.
Goke et al. "Exendin-4 is a potent agonist and truncated exdenin- (9-39) -amide an antagonist at the GLP-1- (7-36) -amide receptor of insulin-secreting β-cells." *J.Biol. Chem.* 268: 19650-19655, 1993.
Gromada et al. "Glucagon-Like Peptide 1(7-36) Amide Stimulates Exocytosis in Human Pancreatic β-Cells by both Proximal and Distal Regulatory Steps in Stimullus-secretion Coupling." *Diabetes* 47:57-65, 1998.

(Continued)

*Primary Examiner*—Lorraine Spector
*Assistant Examiner*—Dong Jiang
(74) *Attorney, Agent, or Firm*—Needle & Rosenberg, P.C.

(57) ABSTRACT

The present invention relates to a population of insulin producing cells made by a process comprising contacting non-insulin producing cells with a growth factor selected from the group consisting of GLP-1 or Exendin-4, growth factors having amino acid sequences substantially homologous to GLP-1 or Exendin-4, and fragmets thereof. The present invention also relates to methods of differentiating non-insulin producing cells into insulin producing cells and of enriching a population of cells for insulin-producing cells. The present invention also relates to methods of treating diabetes.

40 Claims, 26 Drawing Sheets

OTHER PUBLICATIONS

Gutniak et al. "Antidiabetogentic effect of glucagon-like peptide-1 (7-36) amide in normal subjects and patients with diabetes mellitus." *N. Engl. J. Med.* 326: 1316-1322, 1992.

Guz et al. "Expression of murine STF-1, aputative insullin gene transcription factor, in β cells of pancreas, duodenal epithelium and pancreatic excrine and endocrine progenitors during ontogengy." *Development* 121: 11-18, 1995.

Hawes et al. "Distinct pathways of $G_i$-and $G_q$-mediated mitogen-activated protein kinase activaton." *J. Biol. Chem.* 270: 17148-17153, 1995.

Holz et al. "Activation of a cAMP-regulated $Ca^{2+}$ -signaling pathway in pancreatic beta-cells by the insulinotropic hormone glucagon-like-peptide-1." *J. Boil. Chem.* 270: 17749-17757, 1995.

Hosokawa et al. "Mechanism of impaired glucose-potentiated insulin secretion in diabetic 90% pancreatectomy rats. Study using glucagonlike peptide-1 (7-37)." *J. Clin. Invest.* 97: 180-1860, 1996.

Kimura et al. "High concentrations of cholecystokinin octapeptide suppress protein kinase c activity in guinea pig pancreatic acini." *Peptides* 17: 917-925, 1996.

Malhotra et al. "Exendin-4, a new peptide from heloderma suspectum venom, potentiates cholecystokinin-induced amylase from rat pancreatic acini." *Regul. Pept.* 41: 149-156, 1992.

Mashima et al. "Betacellulin and activin A. coordinately convert amylase-secreting AR42J cells into insullin-secreting cells." *J. Clin. Invest.* 97:1647-1654, 1996.

Montrose-Rafizadeh et al. "High potency antagonists of the pancreatic glucagon-like peptide-1 receptor." *J. Biol. Chem.* 272:21201-21206, 1997.

Montrose-Rafizadeh et al. "Incretin hormones regulate glucose-dependent insulin secretion in RIN 1046-38 cells: mechanism of action." *Endocrinology* 135: 589-594, 1994.

Montrose-Rafizdeh et al. "Novel signal transduction and peptide specificity of gluccagon-like peptide receptor in 3T3-L1 adipocytes." *J. Cell. Physiol.* 172: 275-280, 1997.

Nathan et al. "Insulinotropic action of glucagonlike-peptide-1-(7-37) in diabetic and nondiabetic subjects." *Diabetics Care* 15:270-276, 1992.

Nuack et al. "preserve incretin activity of Gucagon-like peptide 1 (&-36) amide but not of synthetic human gastirc inhibitory polypeptide in patients with Type-2 diabetes mellitus." *J. Clin. Invest.* 91:301-307, 1993.

Nauck et al. "normalization of fasting hyperglycemia by exogenous glluagoon-like peptide 1 (7-36) amide in Type 2 (non-insulin-dependent)0 diabetic patients." *Diabetologia* 36:741-744, 1993.

Orskov et al. "Glucagon-like peptide-1, a new hormone of the entero-insular axis." *Diabetilogia* 35: 701-711, 1992.

Perfetti et al. "Age-dependent reduction on insulin secretion and insullin mRNA in isolated islets from rats." *Am. J. Physiol.* 269: E983-990, 1995.

Ritzel et al. "Pharacokinetic, insulinotropic, and glucagonostatic properties of GLP-1 [7-36 amide] after subcutaneous injection in healthy volunteers. Dose-response-relationships." *Diabetologia* 38: 720-725, 1995.

Teitelman "Induction of beta-cell neogenesis by islet injury." *Diabetes Metabolism Rev.* 12: 91-102, 1996.

Thorens et al. "Expression cloning of the pancreatic beta cell receptor for the gluco-incretin hormone glucagon-like peptide 1." *Proc. Natl. Acad. Sci. USA* 89:8641-8645, 1992.

Thorens et al. "Cloning and functional expression of the GLP-1 receptor: Dempstration that exendin-4 is an agonist and exendin-3(9-39) is an agonist of the receptor." *Diabetes* 42: 1678-1682, 1993.

Thorens and Waeber et al. "Glucagon-like peptide-1 and the control of insulin secretion in the normal state and in NIDDM." *Diabetes* 42: 1219-1225, 1993.

Valverde and Villanueva-Penacarrillo et al. "In vitro insulinomimetic effects of GLP-1 in liver, muscle and fat." *Acta Physiologica Scandinavica* 157:359-360, 1996.

Wang et al. Glucagon-like peptides-1 can reverse the age related decline in glucose tolerance in rats. *J. Clin. Invest.* 99: 2883-2889, 1997.

Wang et al. "Glucagon-like peptide-1 affects gene transcription and messenger ribonucleic acid stablity of components of the insulin secretory system in RIN 1046-38 cells." *Endocrinology* 136: 4910-4917, 1995.

Wang et al. "GIP regulates glucose transporters, hexokinases, and glucose-induced insulin secretion in RIN 1046-38 cells." *Moll. Cell. Endo* 116: 81-87, 1996.

Wang et al. "Glucagon-like peptide-1 is a phsyiological incretin in rat." *J. Clin. Invest.* 95: 417-421, 1995.

Widmann et al. "Desensitization and phosporylation of the glucagon-llike peptide-1 (GLP-1) receptor by GLP-1 and 4-phorbol 12-Myristate 13-acetate." *Mol. Endocrinol.* 10: 62-75, 1996.

Willms et al. "Gastric emptying, glucose response, and insulin secretion after a liquid test meal: effects of exgenous glucagon-like peptide-1-(7-36) amide in Type 2 (non-insulin-dependent) diabetic patients." *J. Clin. Endocrinol. Metab.* 81: 327-332, 1996.

Yada et al. "Glucagon-like peptide-1-(7-36) amide and a rise in cyclic adenosine 3', 5'- monophosphate increase cyosolic free $Ca^{2+}$ in rat pancreatic β-cells by enhancing $Ca^{2+}$ channel activity." *Endocrinology* 133: 1685-1692.

Edvell, A. and Lindstrom P., "Proliferation of pancreatic islets in young obese hyperglycemic mice (Umea Ob/Ob)," *Experimental and Clinical Endocrinology & Diabetes* 105(4):A 36 (1997) (abstract).

\* cited by examiner

SEQUENCE LISTING

<160> NUMBER OF SEQ ID NOS: 25

<210> SEQ ID NO 1
<211> LENGTH: 30
<212> TYPE: PRT
<213> ORGANISM: Human

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 31
<212> TYPE: PRT
<213> ORGANISM: Human

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 29
<212> TYPE: PRT
<213> ORGANISM: Human

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly
            20                  25

<210> SEQ ID NO 4
<211> LENGTH: 28
<212> TYPE: PRT
<213> ORGANISM: Human

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys
            20                  25

<210> SEQ ID NO 5
<211> LENGTH: 27
<212> TYPE: PRT
<213> ORGANISM: Human

<400> SEQUENCE: 5

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val
            20                  25

<210> SEQ ID NO 6
<211> LENGTH: 26
<212> TYPE: PRT
<213> ORGANISM: Human

```
<400> SEQUENCE: 6

His Ala Glu Gly Thr Phe Thr Ser Asp Val Ser Ser Tyr Leu Glu Gly
  1               5                  10                  15

Gln Ala Ala Lys Glu Phe Ile Ala Trp Leu
             20                  25

<210> SEQ ID NO 7
<211> LENGTH: 25
<212> TYPE: PRT
<213> ORGANISM: Human

<400> SEQUENCE: 7

His Ala Glu Gly Thr Phe Thr Ser Asp Val Ser Ser Tyr Leu Glu Gly
  1               5                  10                  15

Gln Ala Ala Lys Glu Phe Ile Ala Trp
             20                  25

<210> SEQ ID NO 8
<211> LENGTH: 24
<212> TYPE: PRT
<213> ORGANISM: Human

<400> SEQUENCE: 8

His Ala Glu Gly Thr Phe Thr Ser Asp Val Ser Ser Tyr Leu Glu Gly
  1               5                  10                  15

Gln Ala Ala Lys Glu Phe Ile Ala
             20

<210> SEQ ID NO 9
<211> LENGTH: 39
<212> TYPE: PRT
<213> ORGANISM: Gila monster

<400> SEQUENCE: 9

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Pro Ser
         35

<210> SEQ ID NO 10
<211> LENGTH: 38
<212> TYPE: PRT
<213> ORGANISM: Gila monster

<400> SEQUENCE: 10

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Pro
         35

<210> SEQ ID NO 11
<211> LENGTH: 37
<212> TYPE: PRT
<213> ORGANISM: Gila monster

<400> SEQUENCE: 11
```

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro
        35

<210> SEQ ID NO 12
<211> LENGTH: 36
<212> TYPE: PRT
<213> ORGANISM: Gila monster

<400> SEQUENCE: 12

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro
        35

<210> SEQ ID NO 13
<211> LENGTH: 35
<212> TYPE: PRT
<213> ORGANISM: Gila monster

<400> SEQUENCE: 13

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala
        35

<210> SEQ ID NO 14
<211> LENGTH: 34
<212> TYPE: PRT
<213> ORGANISM: Gila monster

<400> SEQUENCE: 14

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly

<210> SEQ ID NO 15
<211> LENGTH: 33
<212> TYPE: PRT
<213> ORGANISM: Gila monster

<400> SEQUENCE: 15

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser

<210> SEQ ID NO 16
<211> LENGTH: 32
<212> TYPE: PRT

-continued

<210> SEQ ID NO 16
```
<213> ORGANISM: Gila monster

<400> SEQUENCE: 16

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

<210> SEQ ID NO 17
<211> LENGTH: 31
<212> TYPE: PRT
<213> ORGANISM: Gila monster

<400> SEQUENCE: 17

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro
            20                  25                  30

<210> SEQ ID NO 18
<211> LENGTH: 30
<212> TYPE: PRT
<213> ORGANISM: Gila monster

<400> SEQUENCE: 18

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly
            20                  25                  30

<210> SEQ ID NO 19
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 19
gatggatcct gcagaagctt ttttttttt tttttttt                              38

<210> SEQ ID NO 20
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 20
acaggtctct tctgcaacc                                                  19

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 21
aagatgactt catgcgtgcc                                                 20

<210> SEQ ID NO 22
<211> LENGTH: 28
<212> TYPE: DNA
<213> ORGANISM: Artificial Sequence
```

```
<220> FEATURE:
<223> OTHER INFORMATION: Oligonucleotide primer

<400> SEQUENCE: 22
tgcccaggct tttgtcaaac agcacctt                                          28

<210> SEQ ID NO 23
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 23
ctccagtgcc aaggtctgaa                                                   20

<210> SEQ ID NO 24
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 24
gtggctggat tgtttgtaat gctgctg                                           27

<210> SEQ ID NO 25
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 25
cggttcctct tggtgttcat caac                                              24
```

DIFFERENTIATION OF NON-INSULIN PRODUCING CELLS INTO INSULIN PRODUCING CELLS BY GLP-1 OR EXENDIN-4 AND USES THEREOF

CROSS-REFERENCE TO RELATED APPLICATIONS

This application claims the benefit of U.S. Provisional Application No. 60/095,917, filed Aug. 10, 1998.

The government has certain rights to this invention.

BACKGROUND OF THE INVENTION

1. Field of the Invention

The present invention relates to a population of insulin producing cells differentiated from non-insulin producing cells by contacting the non-insulin producing cells with Glucagon-like peptide-1 ("GLP-1"), exendin-4, or related peptides. The present invention also relates to the methods for obtaining the insulin producing cells and therapeutic uses in the treatment of diabetes mellitus.

2. Background Art

The mammalian pancreas is composed of two distinct types of glandular tissue, the exocrine cells that secrete digestive enzymes into the intestine and the endocrine cells that secrete hormones into the blood stream. Endocrine cells were traditionally believed to develop from the neural crest whereas the exocrine cells were believed to develop from the endoderm. More recent work suggests that these two cell types can come from common endodermal precursor cells located along the epithelial lining of the ducts (Teitelman, 1996). It should be noted that the endocrine cells are terminally differentiated and do not divide to make new endocrine cells. Pancreatic endodermal precursor cells are the only cells thought to produce new pancreatic endocrine cells.

The pancreas consists of ducts, which carry the exocrine enzymes (amylase and lipase) to the intestine; acinar cells, which produce the exocrine enzymes; and islets of Langerhans, which contain the endocrine cells that produce and secrete insulin, amylin, and glucagon. These hormones help to maintain normal blood glucose levels within a remarkably narrow range.

Among the islet cells are beta cells which produce and secrete insulin. Insulin production and secretion by the beta cells is controlled by blood glucose levels. Insulin release increases as blood glucose levels increase. Insulin promotes the uptake of glucose by target tissues and, thus, prevents hyperglycemia by shuttling glucose into tissues for storage.

Beta cell dysfunction and the concomitant decrease in insulin production can result in diabetes mellitus. In Type 1 diabetes, the beta cells are completely destroyed by the immune system, resulting in an absence of insulin producing cells (Physician's Guide to Insulin Dependent [Type I] Diabetes Mellitus: Diagnosis and Treatment, American Diabetes Association, 1988). In Type 2 diabetes, the beta cells become progressively less efficient as the target tissues become resistant to the effects of insulin on glucose uptake. Type 2 diabetes is a progressive disease and beta cell function continues to deteriorate despite on-going treatment with any presently available agent (UK Prospective Study Group, 1995). Thus, beta cells are absent in people with Type 1 diabetes and are functionally impaired in people with Type 2 diabetes.

Beta cell dysfunction currently is treated in several different ways. In the treatment of Type 1 diabetes or the late stages of Type 2 diabetes, insulin replacement therapy is used. Insulin therapy, although life-saving, does not restore normoglycemia, even when continuous infusions or multiple injections are used in complex regimes. For example, postprandial levels of glucose continue to be excessively high in individuals on insulin replacement therapy. Thus, insulin therapy must be delivered by multiple daily injections or continuous infusion and the effects must be carefully monitored to avoid hyperglycemia, hypoglycemia, metabolic acidosis, and ketosis.

Replacement of beta cells can be achieved with pancreatic transplants. (Scharp et al., 1991; Warnock et al., 1991). Such transplants, however, require finding a matching donor, surgical procedures for implanting the harvested tissue, and graft acceptance. After transplantation in a person with Type 1 diabetes, on-going immunosuppression therapy is required because cell surface antigens on the beta cells are recognized and attacked by the same processes that destroyed the beta cells originally. Immunosuppressive drugs, such as cyclosporin A, however, have numerous side-effects, including the increase in potential for infection. Transplantation, therefore, can result in numerous complications.

People with Type 2 diabetes are generally treated with drugs that stimulate insulin production and secretion from the beta cells. A major disadvantage of these drugs, however, is that insulin production and secretion is promoted regardless of the level of blood glucose. Thus, food intake must be balanced against the promotion of insulin production and secretion to avoid hypoglycemia or hyperglycemia.

In recent years several new agents have become available to treat Type 2 diabetes. These include metformin, acarbose and troglitazone (see Bressler and Johnson, 1997). However, the drop in hemoglobin A1c obtained by these newer agents is less than adequate (Ghazzi et al., 1997), suggesting that they will not improve the long-term control of diabetes mellitus.

Most recently, glucagon-like peptide-1 (GLP-1), a hormone normally secreted by neuroendocrine cells of the gut in response to food, has been suggested as a new treatment for Type 2 diabetes (Gutniak et al., 1992; Nauck et al., *J. Clin. Invest.*, 1993). It increases insulin release by the beta cells even in subjects with long-standing Type 2 diabetes (Nauck et al., *Diabetologia*, 1993). GLP-1 treatment has an advantage over insulin therapy because GLP-1 stimulates endogenous insulin secretion, which turns off when blood glucose levels drop (Nauck et al., *Diabetologia*, 1993; Elahi et al., 1994), when blood glucose levels are high. GLP-1 promotes euglycemia by increasing insulin release and synthesis, inhibiting glucagon release, and decreasing gastric emptying (Nauck et al., *Diabetologia*, 1993; Elahi et al., 1994; Wills et al., 1996; Nathan et al., 1992; De Ore et al., 1997). GLP-1 also induces an increase in hexokinase messenger RNA levels (Wang et al., *Endocrinology* 1995; Wang et al., 1996). GLP-1 is known to have a potent insulin-secreting effect on beta cells (Thorens and Waeber, 1993; Orskov, 1992) and to increase insulin biosynthesis and proinsulin gene expression when added to insulin-secreting cell lines for 24 hours (Drucker et al., 1987; Fehmann and Habener, 1992). In studies using RIN 1046-38 cells, twenty-four hour treatment with GLP-1 increased glucose responsiveness even after the GLP-1 had been removed for an hour and after several washings of the cells (Montrose-Rafizadeh et al., 1994). Thus, GLP-1 is an insulin releasing agent and an insulinotropic agent (i.e., an agent that increases insulin synthesis) known to have a prolonged effect on beta cells. GLP-1 is a product of posttranlational modification of proglucagon. The sequences of GLP-1 and its active fragments GLP-1 (7–37) and GLP-1 (7–36) amide are known in the art (Fehmann et al., 1995).

GLP-1 receptors have been shown to be present in the gut and in the pancreatic islets (Id.). The receptors belong to a family of G-protein-linked receptors that includes glucagon, secretin, and vasoactive intestinal peptide receptors. After binding of GLP-1 to its receptor there is a rise in cAMP in beta cells of the islets of Langerhans (Widmann et al., 1996), indicating that the receptor is coupled to the adenyl cyclase system by a stimulator G-protein. In peripheral tissues, such as liver, fat and skeletal muscle, however, no increase in cAMP with GLP-1 is seen, suggesting that GLP-1 acts through a different system on peripheral tissues (Valverde and Villanueva-Penacarrillo, 1996).

Exendin-4 is a peptide produced in the salivary glands of the Gila Monster lizard (Goke et al., 1993). The amino acid sequence for Exendin-4 is known in the art (Fehmann et al. 1995). Although it is the product of a uniquely non-mammalian gene and appears to be expressed only in the salivary gland (Chen and Drucker, 1997), Exendin-4 shares a 52% amino acid sequence homology with GLP-1 and in mammals interacts with the GLP-1 receptor (Goke et al., 1993; Thorens et al., 1993). In vitro, Exendin-4 has been shown to promote insulin secretion by insulin producing cells and, given in equimolar quantities, is more potent than GLP-1 at causing insulin release from insulin producing cells.

In vivo studies using GLP-1 have been limited to the use of single or repeated bolus injections or short-term infusions of GLP-1 and subsequent evaluation of the insulin secreting effects. In one such study, infusions of GLP-1 for two hours were tested in patients with Type 1 diabetes for the ability of GLP-1 to promote glucose uptake in muscle and release of glucose from the liver (Gutniak et al., 1992). Therapeutic uses of GLP-1 for increasing the release of insulin have been considered for Type 2 diabetes, but not for Type 1 diabetes, since Type 1 diabetes is marked by an absence of beta cells, the known target cell for GLP-1. Furthermore, GLP-1 has known limitations as a therapeutic agent in the treatment of diabetes because it has a short biological half-life (De Ore et al., 1997), even when given by a bolus subcutaneously (Ritzel et al., 1995). Exendin-4 has not been used previously in in vivo studies. Thus, studies to date have never suggested that either GLP-1 or Exendin-4 is therapeutically effective on pancreatic function in people with Type 1 diabetes or that there are GLP-1 or Exendin-4 target cells in the pancreas other than the beta cells.

SUMMARY OF THE INVENTION

It is an object of the present invention to overcome or reduce the above stated problems with the prior art by providing a population of insulin producing cells made by a process comprising contacting non-insulin producing cells with a growth factor selected from the group consisting of GLP-1 or Exendin-4, growth factors having amino acid sequences substantially homologous to GLP-1 or Exendin-4, and fragments thereof. In addition, a method of differentiating non-insulin producing cells into insulin producing cells, comprising contacting the non-insulin producing cells with a growth factor selected from the group consisting of GLP-1 or Exendin-4, growth factors having amino acid sequences substantially homologous to GLP-1 or Exendin-4, and fragments thereof is provided. Further provided is a method of enriching a population of cells for insulin-producing cells, comprising contacting the population of cells with a growth factor that promotes differentiation of non-insulin producing cells into insulin-producing cells.

Also provided is a method of treating diabetes in a subject diagnosed with Type 1 diabetes, comprising administering to the subject a growth factor selected from the group consisting of GLP-1 or Exendin-4, growth factors having amino acid sequences substantially homologous to GLP-1 or Exendin-4, and fragments thereof by continuous infusion for at least twenty-four hours. The present invention further overcomes the prior art by providing a method of treating diabetes in a subject, comprising obtaining non-insulin producing cells from the subject being treated or from a donor; contacting the non-insulin producing cells with a growth factor, thereby promoting differentiation of non-insulin producing cells into insulin-producing cells; and administering the insulin-producing cells that were promoted to differentiate from non-insulin producing cells to the diabetic subject.

BRIEF DESCRIPTION OF THE DRAWINGS

FIG. 19A shows the typical $[Ca^{2+}]_i$ response observed in at least 85% of the cells. FIG. 19B shows that the $[Ca^{2+}]_i$ response to CCK is almost completely abolished following 60 min exposure to 10 μM ryanodine (RY) and 500 nM thapsigargin (TG). FIG. 19C shows that the $[Ca^{2+}]_i$ transient is abbreviated by reduction of extracellular $Ca^{2+}$ during exposure to CCK.

FIG. 20A shows that exposure to 1 nM GLP-1 induced small, slow, prolonged $[Ca^{2+}]_i$ transients in approximately 50% of AR42J cells. The reduction in the amplitude of the subsequent exposure to 10 nM CCK is shown in FIG. 20B. FIG. 20C shows that the amplitude of the $[Ca^{2+}]_i$ transient is further reduced in response to a second exposure to CCK applied in <10 min.

FIG. 21A shows that glucagon (10 nM) induced slow, small, prolonged $[Ca^{2+}]_i$ transients in approximately 70% of cells. FIG. 21B shows that in cells treated with 10 nM glucagon for 3–10 min, the subsequent $[Ca^{2+}]_i$ transients induced by 10 nM CCK showed a slow rate of rise as well as a prolonged relaxation phase. FIG. 21C shows that brief (1–5 min) exposures to 100 nM 8BcAMP attenuated the relaxation of CCK-induced $[Ca^{2+}]_i$ transients.

FIG. 26 shows immunocytochemistry of AR42J cells. AR42J cells were fixed with glutaraldehyde, and incubated with anti-insulin or anti-glucagon antibody from Linco at a dilution of 1:300.

FIG. 28A shows insulin mRNA at 187 bp. FIG. 28B shows glucagon mRNA at 236 bp. GLP-1 (1 nM) treatment was for 3 days.

FIG. 29A is the autoradiogram and FIG. 29B represents the densitometry readings (relative units). Cells were plated at a density of $10^5$/well in 60 mm dishes, lysed and clarified lysates were then immunoprecipitated with anti-ERK antibody. The immune pellets were analyzed for ERK activity as described in herein. Lane 1, Control AR42J cells. Lane 2, GLP-1 (10 nM)-treated AR42J cells for 3 days. Lane 3, exendin-4 (0.1 nM)-treated cells for 3 days. Lane 4, GLP-1 (10 nM)-plus exendin-4 (0.1 nM)-treated cells for 3 days. Lane 5, GLP-1 (10 nM)-plus exendin-4-plus PKI (300 μM)-treated cells for 3 days. Lane 6, exendin-4 (0.1)-plus PKI (300 μM)-treated cells for 3 days. Lane 7, GLP-1 (10 nM)-plus PKI (300 μM)-treated cells for 3 days. Note that exendin-4 (0.1 nM) is approximately equivalent to GLP-1 (10 nM).

DETAILED DESCRIPTION OF THE INVENTION

Figure 1:
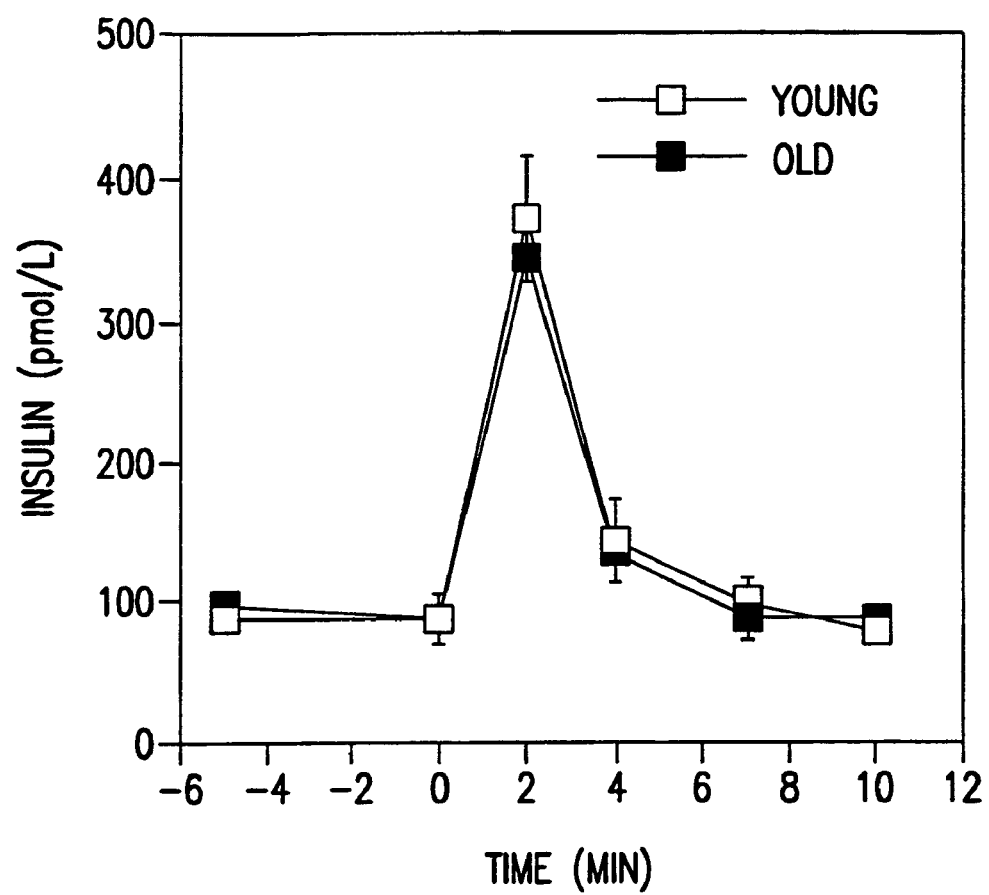
FIG. 1 shows plasma insulin levels in 3 month and 22 month old animals. GLP-1 (0.2 nmol/kg) was given intravenously to fasted, anesthetized animals.

As used in the claims, "a" can mean one or more.

The present invention provides a population of insulin producing cells made by a process comprising contacting non-insulin producing cells with a growth factor selected from the group consisting of GLP-1 or Exendin-4, growth factors having amino acid sequences substantially homologous thereto, and fragments thereof. Non-insulin producing cells, including primary acinar cells, acinar cell lines (e.g., AR42J), and stem cells, that were not previously thought to have GLP-1 receptors and not previously thought to be capable of producing insulin can respond to GLP-1 and Exendin-4, growth factors having amino acid sequences substantially homologous thereto, and fragments thereof by differentiating into insulin producing cells. The effect is to increase the number of insulin-producing cells, an effect that is desirable in the treatment of diabetes mellitus.

As used herein, "insulin producing cells" includes cells that synthesize (i.e., transcribe the insulin gene, translate the proinsulin mRNA, and modify the proinsulin mRNA into the insulin protein), express (i.e., manifest the phenotypic trait carried by the insulin gene), or secrete (release insulin into the extracellular space) insulin in a constitutive or inducible manner. Examples of known insulin producing cells include beta cells, which are located in the pancreatic islets in vivo. In order to secrete insulin, an insulin producing cell also must express IDX-1.

A population of insulin producing cells made by the present invention may contain cells (e.g., beta cells) that produce insulin without the use of the present methods and other cell types. The novelty of the present composition and methods is not negated by the presence of cells in the population that produce insulin naturally (e.g., beta cells). It is also contemplated that the population of insulin producing cells may also contain non-insulin producing cells.

By "non-insulin producing cells" is meant any cell that does not naturally synthesize, express, or secrete insulin constitutively or inducibly. Thus, the term "non-insulin producing cells" as used herein excludes beta cells. Examples of non-insulin producing cells that can be used in the methods of the present invention include pancreatic non-beta cells, such as amylase producing cells, acinar cells, cells of ductal adenocarcinoma cell lines (e.g., CD18, CD11, and Capan-I cells (see Busik et al., 1997; Schaffert et al. 1997), and stem cells. Non-pancreatic cells could also be used, for example, non-pancreatic stem cells and cells of other endocrine or exocrine organs, including, for example, pituitary cells. The non-insulin producing cells can be mammalian cells or, even more specifically, human cells. Examples of the present method using mammalian pancreatic non-islet, pancreatic amylase producing cells, pancreatic acinar cells, and stem cells are provided herein. Stem cells can include pancreatic stem cells and non-pancreatic stem cells that have been promoted to produce IDX-1, Beta 2/NeuroD, and E47. Pancreatic stem cells include duct epithelial precursor cells which give rise to both islet and acinar cells.

The non-insulin producing cells must have GLP-1 receptors or receptors substantially similar to GLP-1 receptors in order to differentiate into insulin producing cells. Preferably, the non-insulin producing cell could also show, upon contact with the growth factor, an increase in intracellular calcium and ERK/MAPK activity and activation of PKC.

As used in the present application, "growth factor" means a substance that can differentiate a non-insulin producing cell into an insulin producing cell. Preferably the growth factor will be one of a group of insulinotropic growth factors, including, for example, GLP-1, exendin-4, betacellulin, Hepatocyte Scatter Factor (HSF) and activin-A, or combinations thereof, excluding betacellulin and activin-A used together and excluding HSF and Activin-A used together. Preferably, greater than 10% of the non-insulin producing cells will differentiate into insulin producing cells upon contact with the growth factor; and, more preferably, at least about 20%, 30%, 40%, 50%, or more will differentiate into insulin producing cells upon contact with the growth factor. Thus, a population of insulin producing cells made in vitro according to the present method can comprise as low as 11% and up to 100% insulin producing cells.

By "amino acid sequences substantially homologous" to GLP-1 or exendin-4 is meant polypeptides that include one or more additional amino acids, deletions of amino acids, or substitutions in the amino acid sequence of GLP-1 or exendin-4 without appreciable loss of functional activity as compared to GLP-1 or exendin-4 in terms of the ability to differentiate insulin producing cells from non-insulin producing cells. For example, the deletion can consist of amino acids that are not essential to the presently defined differentiating activity and the substitution(s) can be conservative (i.e., basic, hydrophilic, or hydrophobic amino acids substituted for the same). Thus, it is understood that, where desired, modifications and changes may be made in the amino acid sequence of GLP-1 and Exendin-4, and a protein having like characteristics still obtained. It is thus contemplated that various changes may be made in the amino acid sequence of the GLP-1 or Exendin-4 amino acid sequence (or underlying nucleic acid sequence) without appreciable loss of biological utility or activity and possibly with an increase in such utility or activity.

The term "fragments," as used herein regarding GLP-1, Exendin-4, or growth factors having amino acid sequences substantially homologous thereto means a polypeptide sequence of at least 5 contiguous amino acids of either GLP-1, Exendin 4, or growth factors having amino acid sequences substantially homologous thereto, wherein the polypeptide sequence has the differentiating function of GLP-1 and Exendin-4 as described herein. The present fragment may have additional functions that can include antigenicity, binding to GLP-1 receptors, DNA binding (as in transcription factors), RNA binding (as in regulating RNA stability or degradation). Active fragments of GLP-1 can include, for example, GLP-1 (7–36) amide (HAEGTFTSD-VSSYLEGQAAKEFIAWLVKGR (SEQ ID NO:1)); GLP-1 (7–37) (HAEGTFTSDVSSYLEGQAAKEFIAWLVKGRG (SEQ ID NO:2)); GLP-1 (7–35) (HAEGTFTSDVS-SYLEGQAAKEFIAWLVKG (SEQ ID NO: 3)); GLP-1 (7–34) (HAEGTFTSDVSSYLEGQAAKEFIAWLVK (SEQ ID NO:4)); GLP-1 (7–33) (HAEGTFTSDVS-SYLEGQAAKEFIAWLV (SEQ ID NO:5)); GLP-1 (7–32) (HAEGTFTSDVSSYLEGQAAKEFIAWL SEQ ID NO:6)); GLP-1 (7–31) (HAEGTFTSDVSSYLEGQAAKEFIAW SEQ ID NO:7)); and GLP-1 (7–30) (HAEGTFTSDVS-SYLEGQAAKEFIA SEQ ID NO:8)). Active fragments of Exendin-4 can include, for example, Exendin-4 (1–39) (HGEGTFTSDLSKQMEEEAVR-LFIEWLKNGGPSSGAPPPS (SEQ ID NO:9)); Exendin-4 (1–38) (HGEGTFTSDLSKQMEEEAVR-LFIEWLKNGGPSSGAPPP (SEQ ID NO: 10)); Exendin-4 (1–37) (HGEGTFTSDLSKQMEEEAVR-LFIEWLKNGGPSSGAPP (SEQ ID NO: 11)); Exendin-4 (1–36) (HGEGTFTSDLSKQMEEEAVR-LFIEWLKNGGPSSGAP (SEQ ID NO: 12)); Exendin-4 (1–35) (HGEGTFTSDLSKQMEEEAVR-LFIEWLKNGGPSSGA (SEQ ID NO: 13)); Exendin-4 (1–34) (HGEGTFTSDLSKQMEEEAVR-LFIEWLKNGGPSSG (SEQ ID NO:14)); Exendin-4 (1–33) (HGEGTFTSDLSKQMEEEAVRLFIEWLKNGGPSS (SEQ ID NO: 15)); Exendin-4 (1–32) (HGEGTFTSDL-SKQMEEEAVRLFIEWLKNGGPS (SEQ ID NO: 16)); Exendin-4 (1–31) (HGEGTFTSDLSKQMEEEAVR-LFIEWLKNGGP (SEQ ID NO: 17)); and Exendin-4 (1–30) (HGEGTFTSDLSKQMEEEAVRLFIEWLKNGG (SEQ ID NO:18)).

Other fragments and modified sequences of GLP-1 are known in the art (U.S. Pat. No. 5,614,492; U.S. Pat. No. 5,545,618; European Patent Application, Publication No. EP 0658568 A1; WO 93/25579). Similar fragments and modified sequences of exendin-4 can be easily extrapolated. It is expected that (a) the following five residues of GLP-1, an H residue at position 7; a G residue at position 10; an F residue at position 12; a T residue at position 13 and a D residue at position 15, and (b) the following five residues of exendin-4, an H residue at position 1; a G residue at position 4, an F residue at position 6; a T residue at position 7 and a D residue at position 9, should be included in a fragment since these residues are highly conserved and are important for receptor binding. Thus, additional fragments or modified sequences can be easily made that exclude or alter amino acids of GLP-1 and exendin-4, other than these 5. Because the differentiation activity disclosed herein is easy to assess, the determination that a fragment is within the scope of the invention is routine.

The present invention provides a population of insulin secreting cells made by the methods described herein. Because IDX-1 expression is required for insulin secretion from a cell, the non-insulin producing cells that can be used to make insulin secreting cells should include cells that express IDX-1 constitutively or upon stimulation with a growth factor or by transfecting the cell with a nucleic acid encoding IDX-1 prior to, during, or after treatment of the non-insulin producing cells with the growth factor.

The present invention also provides a growth factor that can differentiate insulin producing cells from non-insulin producing cells. Such growth factors include but are not limited to GLP-1, Exendin-4, or growth factors having amino acid sequences substantially homologous thereto, and fragments thereof. Differentiation could occur in vivo or in vitro upon contact of the non-insulin producing cell with the growth factor. The contact could be one time by bolus, one time by continuous infusion, or repeatedly by bolus or continuous infusion.

The present invention also provides a method of screening for growth factors that differentiate an insulin producing cell from a non-insulin producing cell. More specifically, the screening method involves the steps of (1) contacting the growth factor to be screened with a non-insulin producing cell, (2) evaluating the non-insulin producing cell for characteristics of insulin producing cells, and (3) identifying the growth factors that differentiate insulin producing cells from non-insulin producing cells. The preferred characteristics of insulin producing cells include the ability to transcribe the insulin gene, the ability to translate the insulin mRNA, the ability to release or secrete insulin, the ability to store insulin, the ability to sense levels of glucose, and the ability to release insulin in a regulated fashion. Since expression of the transcription factors IDX-1, Beta 2/NeuroD, and E47 are believed to be necessary for production of insulin, these factors will also typically be expressed in the insulin-producing cell of the invention.

By "contacting" is meant an instance of exposure of the extracellular surface of a cell to a substance at physiologically effective levels. A cell can be contacted by a growth factor, for example, by adding the growth factor to the culture medium (by continuous infusion, by bolus delivery, or by changing the medium to a medium that contains growth factor) or by adding the growth factor to the intracellular fluid in vivo (by local delivery, systemic delivery, intravenous injection, bolus delivery, or continuous infusion). The duration of "contact" with a cell or group of cells is determined by the time the substance, in this case a growth factor, is present at physiologically effective levels in the medium or extracellular fluid bathing the cell. GLP-1 has a short half-life of several minutes, whereas Exendin-4's half-life is substantially longer, on the order of hours. A bolus of GLP-1 would, therefore, have contact with the cell for minutes, and a bolus of Exendin-4 would contact the cell for hours.

The contacting step in the methods of the present invention can take place in vitro. For example, in a transplantation protocol, ex vivo methods can be employed such that non-insulin producing cells are removed from a donor (e.g., the subject being treated) and maintained outside the body according to standard protocols well known in the art (see Gromada et al., 1998). While maintained outside the body, the cells could be contacted with the growth factor and the cells subsequently infused (e.g., in an acceptable carrier) or transplanted using methods well known in the art into the donor subject or a subject different from the donor subject.

Alternatively, the contacting step of the present invention can take place in vivo. Methods for administering GLP-1, Exendin-4 or related growth factors are provided herein. The GLP-1, Exendin-4, or related growth factors are administered systemically, including, for example, by a pump, by an intravenous line, or by bolus injection (Gutniak et al., 1992; European Patent Application, Publication No. 0619322 A2; U.S. Pat. No. 5,614,492; U.S. Pat. No. 5,545,618). Bolus injection can include subcutaneous, intramuscular, or intraperitoneal routes.

Non-insulin producing cells begin to differentiate into insulin producing cells after about twenty-four hours of contact with GLP-1 or Exendin-4, growth factors having amino acid sequences substantially homologous thereto, or fragments thereof. The maximum number of cells that differentiate into insulin-producing cells usually have done so after about seven days of contact. Interestingly, the new insulin producing cells continue to show the capacity to produce insulin even after contact with GLP-1 or Exendin-4, their fragments or related growth factors is discontinued. The new insulin producing cells show the capacity to produce insulin at least up to 2 weeks after contact is discontinued.

Thus, the contacting step will typically be for at least twenty-four hours. By "at least twenty-four hours," is meant twenty-four hours or greater. Specifically, the non-insulin producing cells can be contacted with the growth factor for 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 hours up to 3, 4, 5, 6, 7, or more days or any particular intervening time in hours or minutes within the above range. Preferably the non-insulin producing cells will be contacted with the growth factor for seven days.

The dosages of GLP-1, Exendin-4, their active fragments or related growth factors to be used in the in vivo or in vitro methods and processes of the invention preferably range from about 1 pmoles/kg/minute to about 100 nmoles/kg/minute for continuous administration and from about 1 nmoles/kg to about 40 mmoles/kg for bolus injection. Preferably, the dosage of GLP-1 in in vitro methods will be 10 pmoles/kg/min to about 100 nmoles/kg/min, and in in vivo methods from about 0.003 nmoles/kg/min to about 48 nmoles/kg/min. More preferably, the dosage of GLP-1 in in vitro methods ranges from about 100 picomoles/kg/minute to about 10 nanomoles/kg/minute, and in in vivo methods from about 0.03 nanomoles/kg/minute to about 4.8 nanomoles/kg/minute. The preferred dosage of exendin-4 in in vitro methods is 1 pmoles/kg/min to about 10 nmoles/kg/mine, and in in vivo from about 1 pmole/kg to about 400 pmoles/kg for a bolus injection. The more preferred dosage of exendin-4 in in vitro methods ranges from about 10 pmole/kg/minute to about 1 nmole/kg/minute, and in in vivo from about 10 pmoles/kg to about 40 pmoles/kg for a bolus injection.

A method of differentiating non-insulin producing cells into insulin producing cells, comprising contacting the non-insulin producing cells with a growth factor selected from the group consisting of GLP-1 or Exendin-4, growth factors having amino acid sequences substantially homologous thereto, and fragments thereof is provided. By "differentiating non-insulin producing cells into insulin producing cells" is meant a change in the phenotypic characteristics of the non-insulin producing cells such that the affected cells have at least the phenotypic characteristic of producing insulin. The affected cell may have all of the phenotypic characteristics of a beta cell or may have less than all of the phenotypic characteristics of a beta cell. The affected cell may produce insulin but otherwise maintain the phenotypic characteristics of the non-insulin producing cell. For example, a non-insulin producing cell, such as a pancreatic amylase producing cell (i.e., pancreatic acinar cell), that is contacted with GLP-1 or Exendin-4 can continue to express amylase, typical of an amylase producing cell, but, unlike the typical amylase producing cell, also produces insulin. Thus, a continuum between complete phenotypic change and a single phenotypic change is possible. The examples show the surprising result that insulin producing capability can be conferred upon mature non-insulin secreting cells (e.g., acinar cells). An increase in proliferation of non-insulin producing cells may precede the differentiation of non-insulin producing cells into insulin producing cells, and "differentiating" is not meant to exclude any proliferation that accompanies the change of the cell to an insulin producing phenotype.

Because of the importance of IDX-1, Beta 2/NeuroD, and E27 in the secretion of insulin, the present invention also provides a method of differentiating non-insulin producing cells into insulin producing cells that includes the additional step of transfecting the non-insulin producing cell with a nucleic acid or nucleic acids encoding IDX-1, Beta 2/NeuroD, and/or E27 prior to contacting the non-insulin producing cell with GLP-1, Exendin-4, or similar growth factor. Alternatively, an additional step can comprise transfecting a cell already contacted with GLP-1 or Exendin-4, or a similar growth factor with a nucleic acid or nucleic acids encoding IDX-1, Beta 2/NeuroD, and/or E27. If the contacted cell is in vivo, transfection could be achieved by retrograde perfusion of plasmid DNA for IDX-1 into the secretory duct of the pancreas (see Goldfine et al., 1997). Additionally, in some cases, expression or IDX-1, Beta 2/NeuroD, and E47 can result from the application of certain proteins to non-IDX expressing cells, including, for example, stem cells.

The present invention provides a method of enriching a population of cells for insulin-producing cells, comprising contacting the population of cells with a growth factor that promotes differentiation of non-insulin producing cells into insulin-producing cells. The population of cells produced by this process is expanded in the number of insulin producing cells and can be used in the treatment methods described herein.

The present invention further provides a method of promoting pancreatic amylase producing cells to produce both insulin and amylase, comprising contacting the pancreatic amylase producing cells with a growth factor selected from the group consisting of GLP-1 or Exendin-4, growth factors having amino acid sequences substantially homologous thereto, and fragments thereof. An example of this method is provided in the examples.

The present invention further provides a method of treating diabetes in a subject diagnosed with Type 1 diabetes, comprising administering to the subject a growth factor selected from the group consisting of GLP-1, growth factors having amino acid sequences substantially homologous thereto, and fragments thereof by continuous infusion for at least twenty-four hours. Alternatively, the growth factor can be selected from the group consisting of Exendin-4, growth factors having amino acid sequences substantially homologous thereto, and fragments thereof. Since Exendin-4 has a fairly long half-life, compared to GLP-1, it can be administered by bolus at least once. The treatment methods are effective to treat diabetes in a subject with Type 1 diabetes, because the growth factor promotes the differentiation of non-insulin producing cells in the subject into insulin producing cells, as described in detail herein.

The subject of the invention can include individual humans, domesticated animals, livestock (e.g., cattle, horses, pigs, etc.), pets (like cats and dogs).

By "diabetes" is meant diabetes mellitus, a metabolic disease characterized by a deficiency or absence of insulin secretion by the pancreas. As used throughout, "diabetes" includes Type 1, Type 2, Type 3, and Type 4 diabetes mellitus unless otherwise specified herein.

The present invention also provides a method of treating diabetes in a subject, comprising obtaining non-insulin producing cells from the subject being treated or from a donor; contacting the non-insulin producing cells with a growth factor in vitro, thereby promoting differentiation of non-insulin producing cells into insulin-producing cells; and administering the insulin-producing cells that were promoted to differentiate from non-insulin producing cells to the diabetic subject. In the method of treating diabetes, wherein the non-insulin producing cells are from a donor, the donor can be a cadaver. As a further embodiment of the present invention, the non-insulin producing cells can be allowed to proliferate in vitro prior to contact with the growth factor. Preferably, promoting differentiation of non-insulin producing cells into insulin-producing cells will result in greater than about 20% differentiation of non-insulin producing cells into insulin-producing cells. Even more preferably, greater than about 25%, 30%, 35%, 40%, 45%, 50%, 55%, 60%, 65%, 70%, 75%, 80%, 85%, or 90% of the treated cells will differentiate into insulin-producing cells.

Altering the surface antigens of the insulin producing cells obtained by the differentiation of the non-insulin producing cells into the insulin producing cells, can reduce the likelihood that the insulin producing cells will cause an immune response. The cells with altered surface antigens can then be administered to the diabetic subject. The cell surface antigens can be altered prior to, during, or after the non-insulin producing cells are differentiated into insulin-producing cells.

The present invention also provides a method of differentiating endothelial cells into smooth muscle cells, comprising contacting the endothelial cells with a growth factor selected from the group consisting of GLP-1 or Exendin-4, growth factors having amino acid sequences substantially homologous thereto, and fragments thereof.

The present invention will now be illustrated with reference to the following examples.

EXAMPLES OF THE INVENTION

Example 1

As GLP-1 in cultured insulinoma cells is known to impact positively on insulin secretion, insulin synthesis and insulin messenger RNA, GLP-1's effects on aging Wistar rats were evaluated.

Materials. GLP-1 and exendin [9–39] (Ex), a peptide receptor antagonist of GLP-1, were purchased from Bachem (King of Prussia, Pa.). Chemical reagents were from Sigma (St Louis, Mo.), unless otherwise stated.

Animals. Three month (young) and 22 month (old) old Wistar rats from the Wistar colony in the NIA (Baltimore, Md.) were used. They had been maintained on rat chow and fed ad libitum. All our aged rats are the offspring of ten founder families maintained at the NIA.

Protocols. To insure that old animals were capable of responding to GLP-1, we carried out an acute experiment with an intravenous bolus of GLP-1. Six old (22 months) and 6 young (3 months) Wistar rats were fasted overnight. Following anesthesia with 50 mg/kg pentobarbital, a catheter was placed in the femoral artery for blood sampling, and a bolus of GLP-1 (0.2 nmol/kg) was given into the saphenous vein over 30 sec. Blood (taken at 2, 4, 7, and 10 min) was collected for insulin determination.

The rats were implanted with an Alzet micro-osmotic pump (Alza Corp., Palo Alto, Calif.) in the interscapular region for 48 hrs. In the treated group GLP-1 was delivered at the rate of 1.5 and Ex at 15 $pmol/kg^{-1}.min^{-1}$. It has been shown that in order to prevent GLP-1's insulinotropic effect a 10-fold higher concentration of Ex is required (Wang et al., *J. Clin. Invest.*, 1995). Control animals received normal saline in their pumps and received their infusion for the same length of time.

For glucose tolerance testing, after the pumps were in place 36 hrs (n=6 each for control and GLP-1 treatment), the rats were fasted overnight, anesthetized with 50 mg/kg pentobarbital, and the pumps were removed, giving a total GLP-1 infusion time of 48 hrs. A catheter was placed in the femoral artery for blood sampling and blood was collected for GLP-1 measurement. An intraperitoneal (ip) glucose tolerance test (IPGTT, Ig/Kg BW) was administered 120 min after removal of the pumps. Blood samples were obtained at 15, 30, 45, 60, and 90 min in order to estimate glucose and insulin levels. Blood (200 µl) was drawn into heparinized tubes containing EDTA for glucose and insulin determination.

For intraislet content of insulin, 14 rats were used. Seven were treated with GLP-1, and seven with saline, as described above. After 48 hrs, preceded by an overnight fast, the animals were sacrificed and islets of Langerhans harvested as described previously (Perfetti et al., 1995; Egan et al., 1991). We then measured the intraislet insulin content in 50 islets picked at random from each individual pancreas. Picked islets were centrifuged, any residual medium was removed, the pellet was suspended in ice-cold acid-ethanol (500 ul) and homogenized. After centrifugation of the homogenate (1400×g, 4° C.) the supernatant was collected for measurement of intracellular insulin. The pellet was dissolved in formic acid and protein content was determined.

Assays. Plasma glucose was measured by the glucose oxidase method (Egan et al., 1991). Insulin and GLP-1 were measured by RIA as previously published (Wang et al., *Endocrinology*, 1995; Nathan et al., 1992). The amount of cellular proteins was measured using the Bradford method (Bio-Rad Richmond, Calif.) using bovine γ-globulin as standard.

RNA isolation and quantitation of endocrine pancreatic mRNAs.

Whole pancreata of rats that had been subjected to 48 hrs infusion with GLP-1 or saline were used to extract total RNA. After an overnight fast, animals were sacrificed, pancreata were removed and frozen in liquid nitrogen as quickly as possible. RNA was extracted by homogenization in guanidinium isothiocyanate, followed by ultracentrifugation on a 5.7 M cesium chloride cushion (Glisin et al., 1974; Chigwin et al., 1979). Poly-A RNA was then prepared from total RNA by affinity chromatography using oligo (dT) columns (Biolabs INC, Beverly, Mass.). RNA was quantified by spectrophotometric analysis at 260 nM. Slot-blot analysis using poly-A RNA was used for quantitation of mRNA levels of glucokinase, which is the main glucose sensor of the beta cell (Matschinsky, 1990), the three hexokinases, GLUT2, the major glucose transporter of the beta cell (Mueckler, 1990), and insulin. Four micrograms of poly-A RNA were diluted in 50 µl TE buffer (Tris-HCL 10 mM, EDTA 1 mM, pH 7.4), 20 µl of 37% formaldehyde and 20 µl of 10× SSC. Samples were incubated at 60° C. for 15 min and then diluted with 1 ml of ice-cold 10× SSC (1×SCC=0.15 M NaCl+0.015 sodium citrate). Each well of slot-blot minifolder was rinsed once with ice-cold 10× SSC and 300 µl of sample per well was then loaded in triplicate onto the membrane. Vacuum was applied to drain the samples through the membrane, followed by three washes of the wells with ice-cold 10× SSC. Finally, membranes were baked for 2 hrs at 80° C. in a vacuum oven for RNA crosslinking.

The hybridizations with cDNA probes (rat insulin II from Dr. S. J. Giddings, Washington University, St. Louis, Mo.; rat glucokinase from Dr. M. A. Magnuson, Vanderbilt University, Nashville, Tenn.; rat GLUT2 from Dr. M. J. Birnbaum, Harvard Medical School, Boston, Mass.; and hexokinase I, II, III cDNAs from Dr. J. E. Wilson, Michigan State University, East Lancing, Mich.) were carried out as previously described (Wang et al., *Endocrinology*, 1995; Wang et al., *Mol. Cell. Endocrinol.*, 1996). All cDNA probes were labeled with [$^{32}$P] dCTP (Amersham Life Science, Arlington Heights, Ill.) by random priming procedure using Sequenase (United States Biochemical, Cleveland, Ohio). An oligonucleotide homologous to the poly-A tail of mRNAs was synthesized on an Applied Biosystem DNA synthesizer (5'GATGGATCCTGCA-GAAGCTTTTTTTTTTTTTTTTTTT3') and used to quantify total cellular mRNA. Hybridization with oligo dT$_{20}$ was carried out in order to verify that an approximately equal amount of RNA was used for each sample. Oligonucleotide probes were end-labeled with [$^{32}$P] γATP (Amersham) using T4 polynucleotide kinase (New England Biolabs, Beverly, Mass.). The hybridizations with oligonucleotide probes were carried out as described before (Wang et al., *Endocrinology*, 1995; Wang et al., *Mol. Cell. Endocrinol.*, 1996) and quantified using a Betascope 603 blot analyzer (Betagen, Walthman, Mass.).

RNA isolation and quantitation of mRNAs in islets of Langerhans. To confirm the changes seen in whole pancreata RNA was isolated from islets of Langerhans from animals treated as described above with GLP-1. Islets were isolated and RNA extracted using the micromethod, previously described (Perfetti et al., 1995). Approximately 5 µg of total islet RNA was from one pancreas. Slot-Blot analysis was carried out to quantitate mRNA levels of the hexokinases, GLUT2, and insulin.

Statistical analysis The data were expressed as the mean±SEM. Significance of the insulin and glucose data obtained from the IPGTT were tested using repeated measures analysis of variance by SAS (SAS Institute Inc.; Cary, N.C.). If a significant interaction was documented (p<0.05), values at single time points were compared by non-paired Student's t test. All other data were analyzed using the non-paired Student's t test: a p<0.05 was judged as significant.

Response to acute iv GLP-1 bolus. Old and young fasted animals responded equally well to a bolus of 0.2 nmol/kg GLP-1 delivered over 30 sec. Their insulin responses were superimposable (FIG. 1). At 2 min after completion of the bolus the insulin response was maximal in both young (373.3±43.7 pmol/l) and old (347.7±25.7 pmol/l) animals and in both groups insulin levels had returned to baseline at 10 min.

Figure 2A:
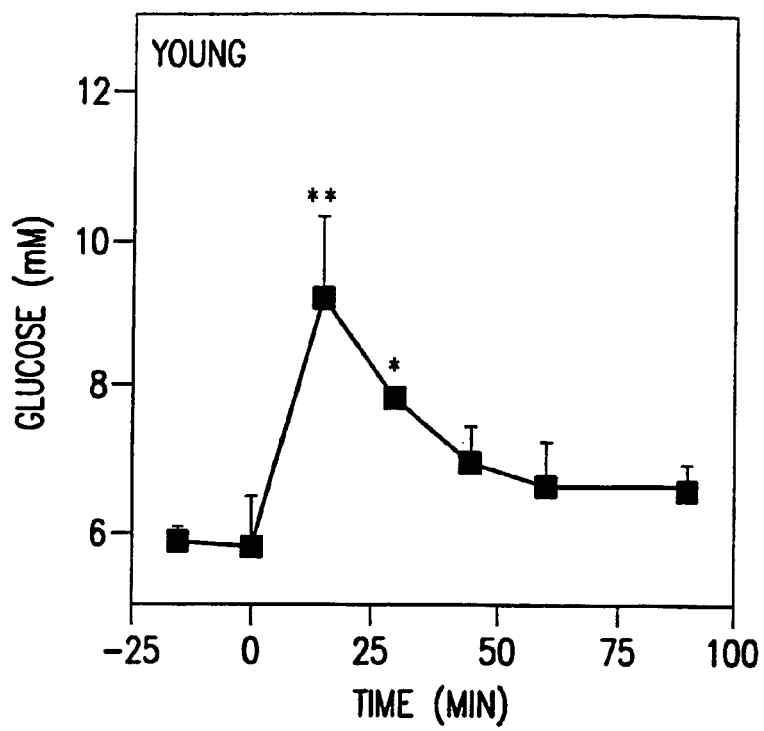
FIG. 2 shows plasma glucose levels during a glucose tolerance in 22 month old animals. GLP-1-treated animals received 1.5 pmol/kg/min for 48 hrs by subcutaneous infusion. Controls were infused with saline. Glucose (1 g/kg) was given ip and the blood glucose measured at the times indicated. The results are a mean (±SEM) of 6 treated and 6 control animals. Repeated measures analysis of variance from 0–30 min showed a value of $p<0.05$. Asterisks indicate: * $p<0.05$, ** $p<0.01$, as determined by unpaired Student's t test.
Figure 2B:
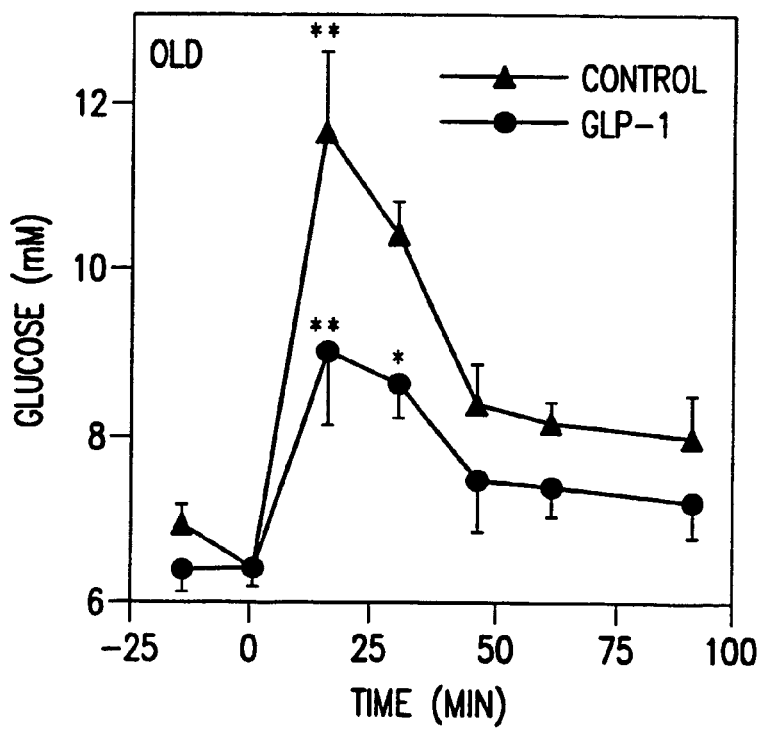
Figure 3:
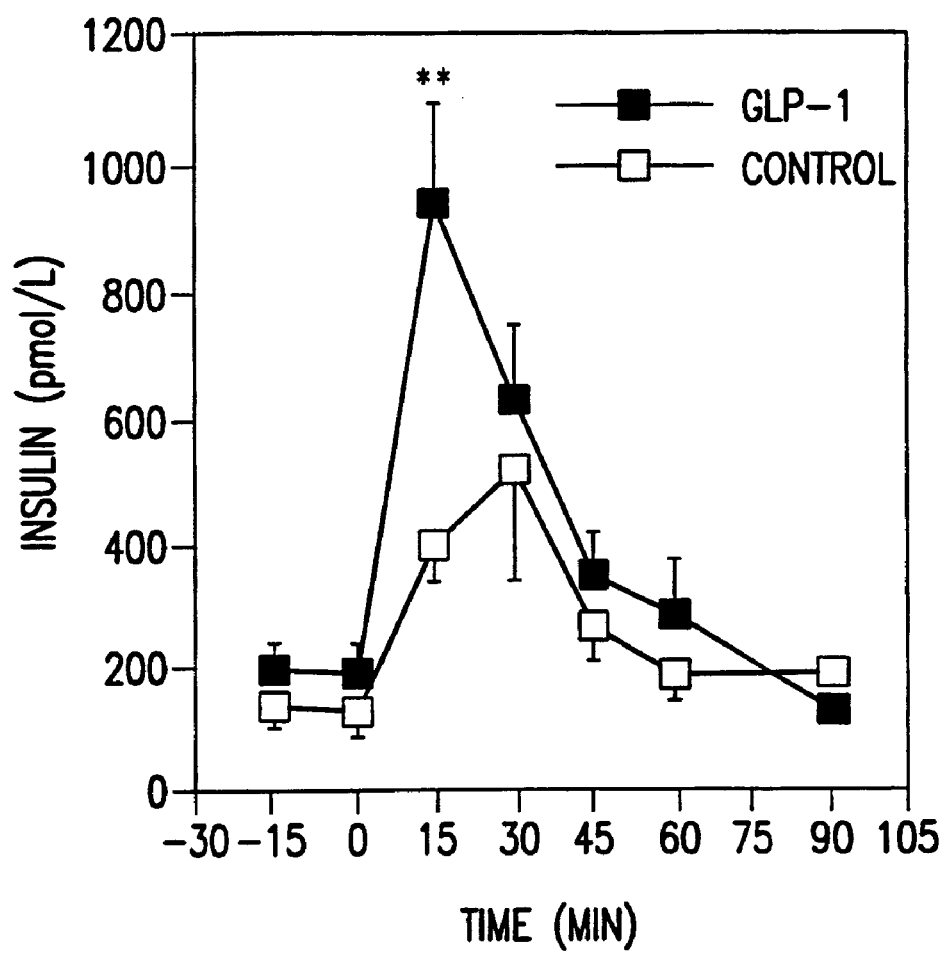
FIG. 3 shows plasma insulin levels during a glucose tolerance test in 22 month old animals. GLP-1-treated animals received 1.5 pmol/kg/min for 48 hrs by subcutaneous injection. Controls were infused with saline. Glucose (1 g/kg) was given ip and serum insulin measured at the times indicated. The results are mean (±SEM) of 6 treated and 6 control animals. Repeated measures analysis of variance from 0–30 min showed a value of $p<0.05$. The asterisk indicates a $p<0.01$, as determined by unpaired Student's t test.

Glucose tolerance testing. Old animals have frank glucose intolerance when compared to young animals during an IPGTT (FIG. 2). Fasting glucose, taken just prior to the ip glucose, was not different between treated and control animals. Blood glucose was significantly lower during the glucose tolerance test in the animals treated with GLP-1 when compared to control animals at the 15 (9.04±0.92 vs 11.61±0.23 mmol/l) and 30 (8.61±0.39 vs 10.36±0.43 mmol/l) min time points (FIG. 2). The old animals were also no longer glucose intolerant when compared with young animals. On reviewing the insulin response at the same time it can be seen that the 15 min insulin response was significantly better in the GLP-1-treated animals compared to the controls (FIG. 3). Indeed, the saline-treated rats had their peak insulin level at 30 min, while the GLP-1-treated animals peaked at 15 min. This brisk insulin response accounted for the drop in blood glucose in the treated animals (FIG. 2). Overnight fasting levels of insulin were higher in the GLP-1-treated animals but due to great intranimal variation this was not statistically different from controls (192±47 vs. 134±45 pmol/l). 48 hr infusion of GLP-1 in 22 month old Wistar rats potentiates insulin response to an IPGTT. This phenomenon is observed even after termination of the GLP-1 infusion, indicating that GLP-1 is capable of inducing long-term changes that go over and beyond modulating insulin release. The major change in the insulin-response curve was in early insulin release after the glucose load, and was induced by a shift in the maximum insulin secretion from 30 min after glucose injection, as observed in controls, to only 15 min in the GLP-1 treated rats.

Figure 4:
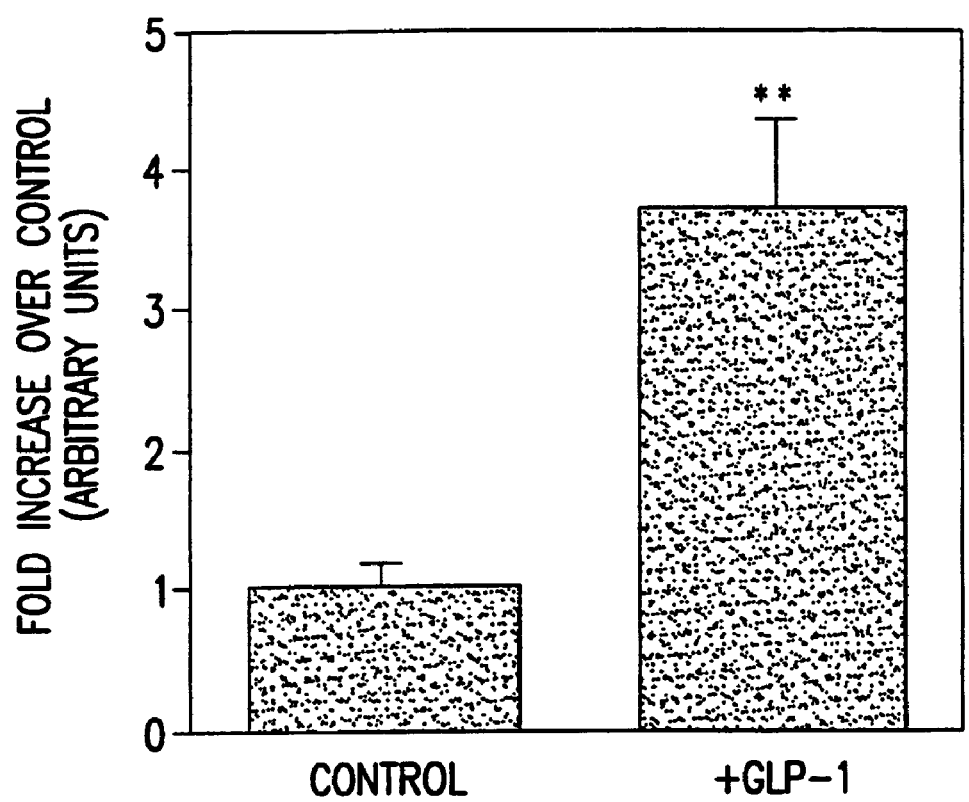
FIG. 4 shows the fold increase in islet insulin content after 48 hrs infusion of saline (control, 7 animals) or GLP-1 (1.5 pmol/kg/min, 7 animals) in 22 month old rats. ** $p<0.01$ by unpaired Student's t test.

Intraislet insulin content. There was variation in the amount of insulin between the islets from each individual pancreas as might be expected from aged animals (FIG. 4). However, there was consistently more insulin in the islets from treated animals (p<0.01). Islets from controls and GLP-1 treated rats had 5.31±1.19 vs. 19.68±3.62 ng of insulin per ug of total pancreatic proteins, respectively.

GLP-1 plasma levels. We measured plasma GLP-1 in 3 animals 6 hrs after commencement of the GLP-1 infusion to insure both that steady state GLP-1 levels were reached and to verify that the peptide was actually being infused. Plasma GLP-1 level at 6 hrs was 106.7±17.6 while at 48 hrs it was 125.0±41.4 pmol/l. Before the commencement of the glucose tolerance testing plasma GLP-1 was below the level of detectability of the assay. Fasting GLP-1 levels in control Wistar rats were 10–20 pmol/l. There was no difference in the fasting levels of GLP-1 between the young and old animals. Therefore, our infusion of GLP-1 raised plasma GLP-1 levels to approximately 6 times the fasting levels. Since fed levels in Wistar rats (Wang et al., *J. Clin. Invest.*, 1995), as well as humans (Gutniak et al., 1992), are reported to approximately double after eating, the plasma levels attained with the pumps were pharmacological.

Effect of GLP-1 on gene expression. We measured the abundance of insulin mRNA as well as mRNA levels of other factors involved in the early steps of glucose-mediated insulin release as well as glucose metabolism in beta cells. Results were quantified by densitometry, normalized by using oligo dT hybridization and expressed in relative terms by assigning the young control result a value of 1. FIG. 6 shows the blots for insulin mRNA from whole pancreata in 6 young and 12 old animals ans combined results from all the animals shown in FIG. 5. FIG. 7 shows the blots of three isolated islet RNA preparations from old animals.

Figure 5A:
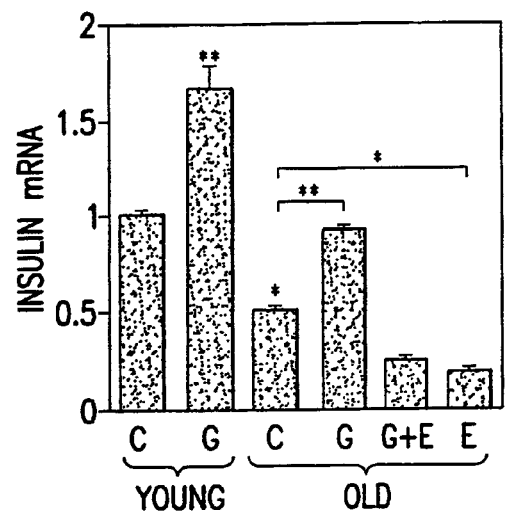
FIG. 5 shows insulin mRNA levels in pancreata from control, GLP-1-, Ex+GLP-1-, and Ex-treated 22 month old animals. Each sample represents an individual pancreas, with four animals in each treatment group.
Figure 6:
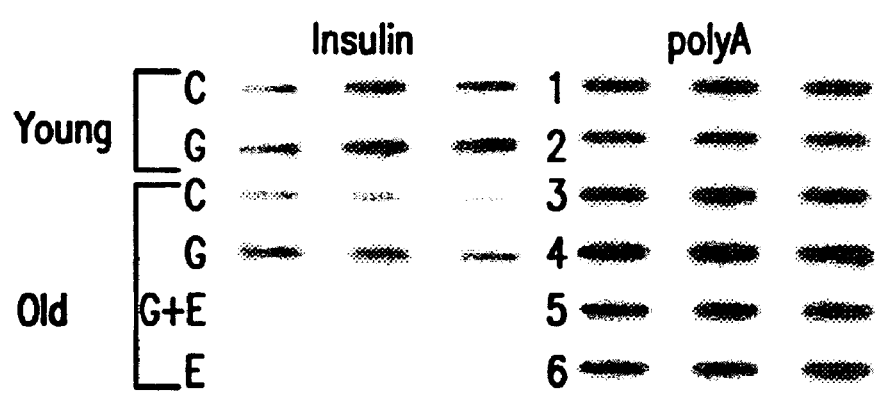
FIG. 6 shows GLUT2 mRNA levels in pancreata from control, GLP-1-, Ex+GLP-1-, and Ex-treated 22 month old animals. Each sample represents an individual pancreas, with four animals in each treatment group.
Figure 7:
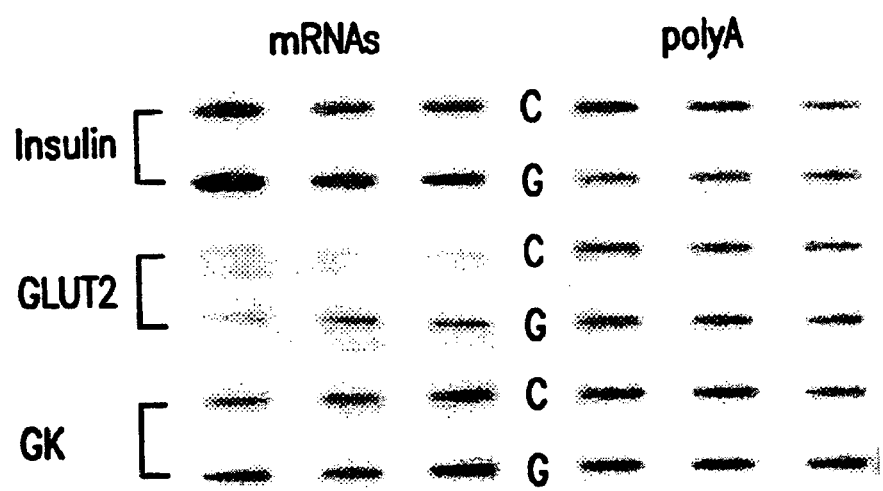
FIG. 7 shows glucokinase mRNA in pancreata from control, GLP-1-, Ex+GLP-1-, and Ex-treated 22 month old animals. Each sample represents an individual pancreas, with four animals in each treatment group.

The levels of insulin mRNA were increased approximately 50% in old vs young animals (FIG. 5A, P<0.05, and FIG. 6). GLP-1 increased the insulin mRNA in both young and old animals compared to controls (FIG. 5A, P<0.01 and FIG. 6). Similar results can be seen in the isolated islet preparations (FIG. 7). This increase was entirely prevented when the animals were treated simultaneously with Ex, an inhibitor of GLP-1 binding to its own receptor. Of great interest is the fact that in the animals treated with Ex alone or Ex with GLP-1, the insulin mRNA levels were lower than in controls (p<0.05). Insulin mRNA levels fell an average of 60% in the presence of Ex alone.

Figure 5B:
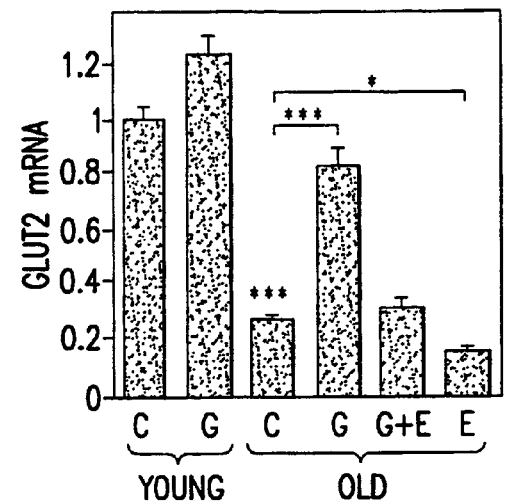

GLUT-2 mRNA levels in old animals were decreased by 70% compared with young controls and this was entirely reversed by GLP-1 treatment (FIG. 5B, P<0.001). The increase in GLUT2 mRNA levels in old animals by GLP-1 can be seen in both islet (FIG. 7) and whole pancreatic preparations (FIG. 6). in the young animals, GLP-1 did not significantly influence the GLUT2 mRNA levels (FIG. 5). The levels fell by 50% in the presence of Ex alone (FIG. 5B, P<0.05), but not in the animals treated with Ex and GLP-1 (FIG. 5B).

Figure 5C:
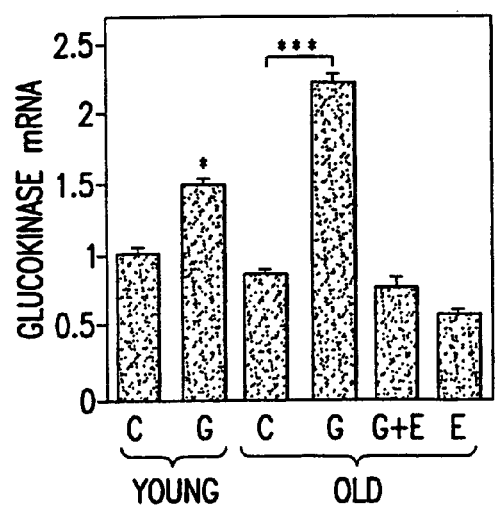

There were no differences between young and old animals in glucokinase mRNA levels (FIG. 5C). GLP-1 significantly increased glucokinase levels in young (FIG. 5, P<0.05), but much more so in old animals (FIG. 5C, P<0.001, FIG. 7). Similar results were seen in the old animals with the isolated islet preparations (FIG. 7). Ex completely prevented GLP-1—induced increases in glucokinase mRNA.

For all preparations, the results from the pancreata were reflected in the islets. Hexokinase I, II and III mRNA levels were very low in the whole pancreata and islets and did not appear to be altered by GLP-1 treatment. We also infused GLP-1 for 5d into old rats (n=6) and found the same results as with the 48-h infusion.

Following continuous infusion with GLP-1, the pancreata were surprisingly larger than control pancreata. The pancreata of treated animals weighed 26% more than the pancreata of control animals.

Also, surprisingly, insulin secretion remained improved even after removal of the exogenous source of GLP-1. The biological half-life of GLP-1's insulinotropic action in blood is 6–8 min (Elahi et al., 1994) and since GLP-1 infusion had been terminated at least 2 hours prior to performing the glucose tolerance testing the continued presence of elevated GLP-1 levels, at least in the short-term, was not necessary for the improvement in glucose tolerance in the aging Wistar animals.

GLP-1 increases insulin biosynthesis and insulin mRNA levels in vivo, as previously shown in insulinoma cells (Wang et al., *Endocrinology*, 1995). GLP-1 would also appear to be necessary for the normal maintenance of mRNA levels of insulin in the pancreas. Not only did Ex inhibit the GLP-1 effect on insulin mRNA, but it also caused a decrease in insulin mRNA in animals given Ex alone. Ex is a competitive inhibitor of GLP-1 binding to its receptor, a 10-fold higher concentration of Ex being required to inhibit GLP-1's insulinotropic effect (Wang et al., *J. Clin. Invest.*, 1995), so presumably it was inhibiting the binding of endogenous GLP-1 in the animals that received Ex alone. This means that GLP-1 has effects on maintaining insulin mRNA levels in the physiological range.

It has been proposed that in Type 2 diabetes the beta cell stores of insulin fall below a critical level, and that this causes a subsequent reduction in glucose-induced insulin responses (Hosokawa et al., 1996). As our data show, GLP-1 is capable of increasing intraislet insulin content and when given continuously, rather than just by bolus, may also induce changes beneficial to beta cell function, over and beyond its effects on simply insulin secretion.

Example 2

Exendin-4 is a peptide produced in the salivary glands of the Gila Monster lizard. In the present example, we report that in Wistar rats, bred in the National Institute of Aging (NIA), it was a far more potent insulinotropic agent in several ways than is GLP-1. We further report that exendin-4 leads to sustained improvement of diabetic control in a rodent model of type 2 diabetes.

Materials. Exendin-4 and GLP-1 were purchased from Bachem (King of Prussia, Pa.). Chemical reagents were from Sigma (St Louis, Mo.), unless otherwise stated.

Animals. Four month old Wistar rats from the Wistar colony in the NIA (Baltimore, Md.) were used for the acute experiments of the effects of exendin-4 and GLP-1 (see Example 1). They had been maintained on standard lab chow and fed ad libitum. For the long-term experiments, diabetic mice (C57BLKS/J-Lepr$^{db}$/Lepr$^{db}$) lacking the leptin receptor, and their non-diabetic littermates were purchased at 4 weeks of age from Jackson Laboratories (Bar Harbor, Me.). They were housed two per cage and also were fed ad libitum. The same mice were caged together for the duration of the study. Wistar rats are caged on wire while the bedding for the mice was a paper based product, "Carefresh" (Absorption Co., Bellingham, Wash.).

Protocols. Wistar rats were fasted overnight. Following anesthesia with 50 mg/kg pentobarbital, a catheter was placed in the femoral artery for blood sampling. A bolus of either exendin-4 or GLP-1 was given into the saphenous vein (iv) over 30 sec to 12 animals, while a bolus of normal saline (NaCl) was given to the other six. The order of the injections was rotated. Blood (taken at −5, 0, 2, 5, 15, 30, 60, 120, and 180 min) was drawn into heparinized tubes containing EDTA and aprotinin for insulin determination (See Example 1). Animals were acclimated to the facility for at least 2 days.

Eleven diabetic and 10 non-diabetic animals received 24 mmol/kg exendin-4 ip daily thereafter (7–9 am) while 10 diabetic and 10 non-diabetic animals received ip NaCl. Subsequently, whole blood glucose levels, taken from a retro-orbital sinus, were determined in the mice using a Glucometer Elite (Bayer). This regimen was continued for 12–13 weeks. On day eight two of the non-diabetic mice (cage-mates) and day fourteen one of the diabetic mice died just after receiving exendin-4. Animals were weighed weekly. After one week of the regimen blood samples were again taken from a retro-orbital sinus for determination of insulin and glucose levels. At the end of the regimen, fasting blood samples were obtained for glucose and insulin levels and whole blood containing EDTA was assayed for hemoglobin A1c (Hb A1c) on the same day from the four groups.

In another group of eight diabetic mice 14 weeks old we gave 24 nmol/kg exendin-4 ip daily and NaCl ip daily for five days to four each of the group.

cAMP determinations. Islets of Langerhans were harvested from Wistar rats (Perfetti et al., 1995) and batches of 25 islets were then incubated for 1 h at 37° C. in a buffer containing (mM) 140 NaCl, 5 KCl, 1 NaPO$_4$ 1 MgSO$_4$, 5 glucose, 2 CaCl$_2$, 20 HEPES, buffer (pH 7.4) and 0.1% bovine serum albumin. Following this, they were incubated in the same buffer for 1 h in the presence of GLP-1 (1 nM) or exendin-4 (1 nM). Some batches of islets were then washed three times with ice-cold phosphate buffer saline (PBS) and lysed with 1 ml ice-cold 0.6 mM perchloric acid.

Other batches were washed three times in the buffer at 37° C. to remove peptide and left another 15 min before being washed three times in ice-cold PBS followed by lysis with the perchloric acid. The lysates (950 μl) were then transferred to microcentrifuge tubes and cAMP measured as previously described (See Example 1) using a cAMP [$^3$H] assay kit (Amersham). Cellular protein was assayed using the Bradford method (Bio-Rad, Richmond, Calif.) using bovine γ-globulin as standard.

Assays. Plasma glucose was measured by the glucose oxidase method (Wang et al., 1997). Insulin was measured by RIA as previously described (See Example 1). Hb A1c was assayed using a BIO-RAD (Herculas Calif.) DiaSTAT machine which uses low pressure cation exchange chromatography in conjunction with gradient elution to separate hemoglobin subtypes and variants from hemolyzed blood. The separated hemoglobin fractions were monitored by means of absorption of light at 415 nm.

Statistical methods. All results are given as mean±SEM. T tests were based on the results of an F test that looked at the equality of variance of the two means. If the variances were statistically significantly different then the t test was based on unequal variances. For determination of the $EC_{50}$ the basal plasma insulin levels were subtracted and the remaining activity at each concentration was expressed as a percent of the maximal activity (achieved by an excess of peptide). This was then transformed into a logit format where logit=ln (% activity/[100-% activity]) and was plotted as a function of the log concentration of the compound.

Figure 8:
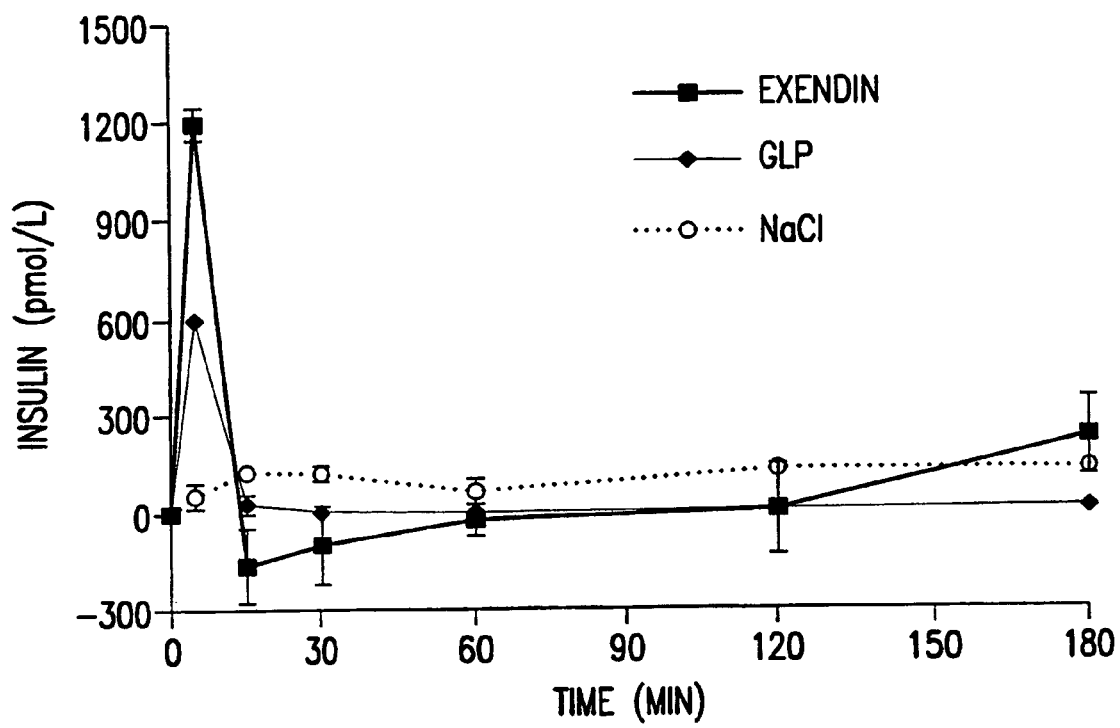
FIG. 8 shows plasma insulin concentrations in fasted anesthetized rats after intravenous (iv) boli of GLP-1 (0.4 nmol/kg) and exendin-4 (0.4 nmol/kg) in 100 µl NaCl. NaCl (100 µl) was also given iv to a control group. Values are expressed as mean±SEM (n=6 per group).
Figure 9:
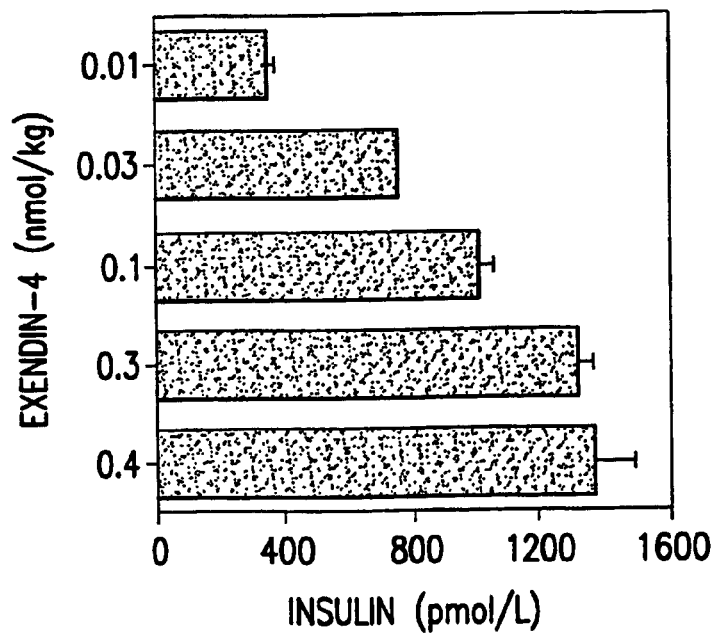
FIG. 9 shows insulin concentrations in fasted anaesthetized rats 2 min after intravenous boli of exendin-4 at the concentrations shown. Values are expressed as mean±SEM (n=6 per exendin-4 concentration).

Exendin-4 effects in Wistar rats. Exendin-4 was more potent an insulinotropic agent than GLP-1 on several levels when given intravenously. Maximal insulin response in our Wistar rats is seen with 0.4 nmol/kg GLP-1 (De Ore et al., 1997). At this same exendin-4 concentration maximal insulin response is approximately doubled (FIG. 8). Insulin levels return to baseline by 10 min with GLP-1, but with exendin-4 they actually go below baseline and have returned to baseline by 60 min. $EC_{50}$ concentration for insulin release is lower and the maximum amount of insulin secreted by exendin-4 is higher than with GLP-1. $EC_{50}$ was 0.019 (FIG. 9) versus 0.19 mmol/kg for exendin-4 versus GLP-1 (See Example 1), respectively. The animals given exendin-4 had an obvious increase in urine output for the duration of the study (we did not quantitate the volume of urine) as they continued to urinate frequently during the study despite the blood drawing which would be diminishing circulating blood volume, while the GLP-1-treated animals urinated little if any during the study.

Figure 10:
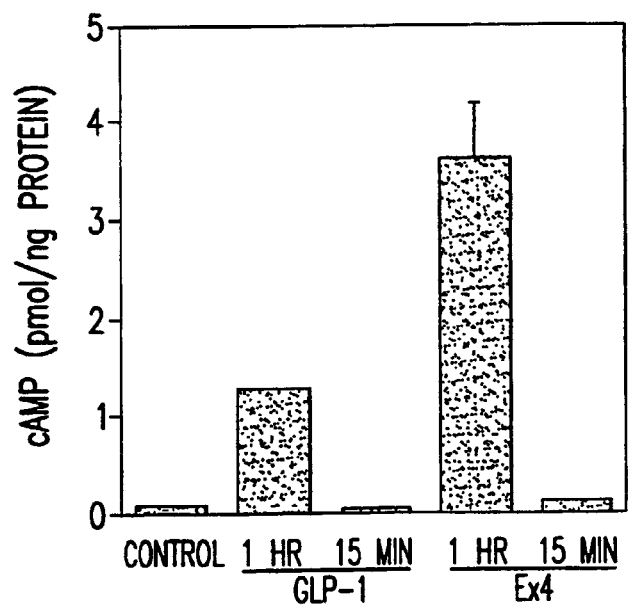
FIG. 10 shows the effects of GLP-1 (1 nM) and exendin-4 (1 nM) treatment for 1 hr on intracellular cAMP levels in islets of Langerhans. Given are means±SEM of 4 experiments, each done in triplicate. Exendin-4 was more effective than GLP-1 ($p<0.01$). Note that after washing some of the islets in buffer following the hr in the presence of the peptides and then removing the islets approximately 15 min later cAMP levels had returned to baseline.

Effects of exendin-4 and GLP-1 on cAMP levels in isolated islets. Exendin-4 increased cAMP levels more in isolated islets than GLP-1 at equimolar concentrations. GLP-1 increased cAMP in a concentration-dependent manner with maximum cAMP response at 1 nM. At that concentration of exendin-4 cAMP levels were approximately 3-fold higher (FIG. 10) than with GLP-1. This probably explains why exendin-4 causes a higher maximal insulin release than GLP-1. In an effort to see if exendin-4 or GLP-1 might remain on the GLP-1 receptor and so maintain an increase in cAMP after the removal of the peptides from the buffer solution we removed the peptide from some islets by three washes in fresh buffer and then measured cAMP after 15 min. With both peptides, cAMP levels returned to baseline at least by 15 min.

Figure 11:
FIG. 11 shows a photograph of cages housing the diabetic mice taken after nine weeks of treatment with exendin-4 (24 nmol/kg) or NaCl intraperitoneally daily, 24 hours after the previous bedding change. Diabetic mice were housed two per cage. Bedding was changed every 24 hours for the diabetic animals after the first few weeks of treatment. The cage on the right contained the exendin-4-treated animals while the cage on the left contained the NaCl-treated animals.

Effects of chronic treatment with exendin-4 in mice. The biological activity of exendin-4, as measured by its ability to lower blood sugar, was much longer than we expected when given ip or subcutaneously to diabetic animals. In preliminary experiments we found that exendin-4-treated diabetic mice had lower blood sugars 24 hours after ip and subcutaneous (sc) injections while with GLP-1 injections, blood sugars were back to baseline. This lead us to design a long-term experiment with exendin-4. At the initiation of the daily ip exendin-4 regimen in the mice fasting blood glucose was 145±51 mg/dl in the non-diabetic mice and 232±38 mg/dl in the diabetic mice. After one week of treatment the fasting glucose level in the exendin-4-treated non-diabetic mice was 70±25 mg/dl and was significantly lower than in the NaCl-treated non-diabetic animals, 135±5 mg/dl ($p<0.05$). The diabetic animals had a highly significant response to exendin-4. Glucose levels dropped to 90±11 mg/dl in the exendin-4-treated animals from 238±51 mg/dl ($p<0.002$) in the NaCl-treated animals (Table 1). We measured fasting insulin levels in the diabetic animals that received NaCl or exendin-4. They were higher in the animals that received exendin-4 ($p<0.002$). On the basis of these data, we continued to treat the animals daily with exendin-4. As the bedding was a paper-based product which turns progressively darker with increased urination, it was clear that the cages of the exendin-4-treated diabetic animals, while not totally dry as were the non-diabetic cages, always were obviously drier 24 hours after changing than the cages of the NaCl-treated diabetic animals (FIG. 11, photograph taken after 9 weeks treatment). We surmised that the decreased urination in the exendin-4-treated diabetic mice was due to less osmotic diuresis because of lower blood glucose.

The diabetic animals were clearly heavier than the non-diabetic animals. After 9 weeks the weight of the non-diabetic animals reached a plateau at approximately 28 grams (g) while the diabetic animals continued to gain weight. At 13–14 weeks of treatment the NaCl-treated animals began to lose weight (38.7 g) while the exendin-4-treated animals maintained their weight (46.7 g).

Figure 12:
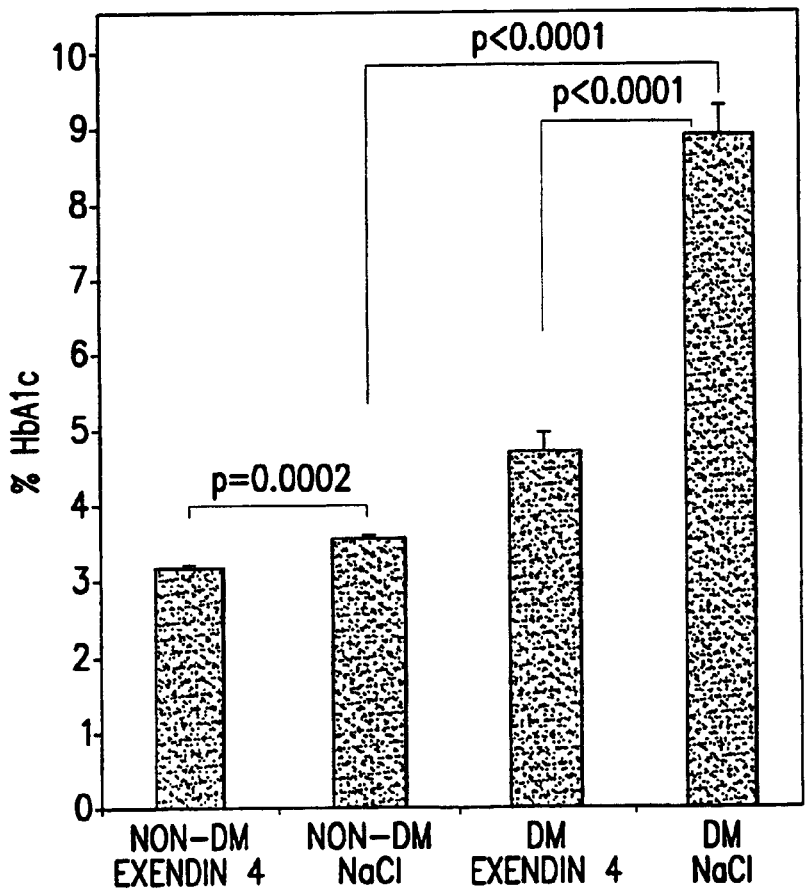
FIG. 12 shows hemoglobin A1c levels in the diabetic and non-diabetic mice given either exendin-4 (24 mmol/kg) or normal saline intraperitoneally daily for 12–13 weeks. Values are expressed as mean±SEM (n=9–10 per group).
Figure 13A:
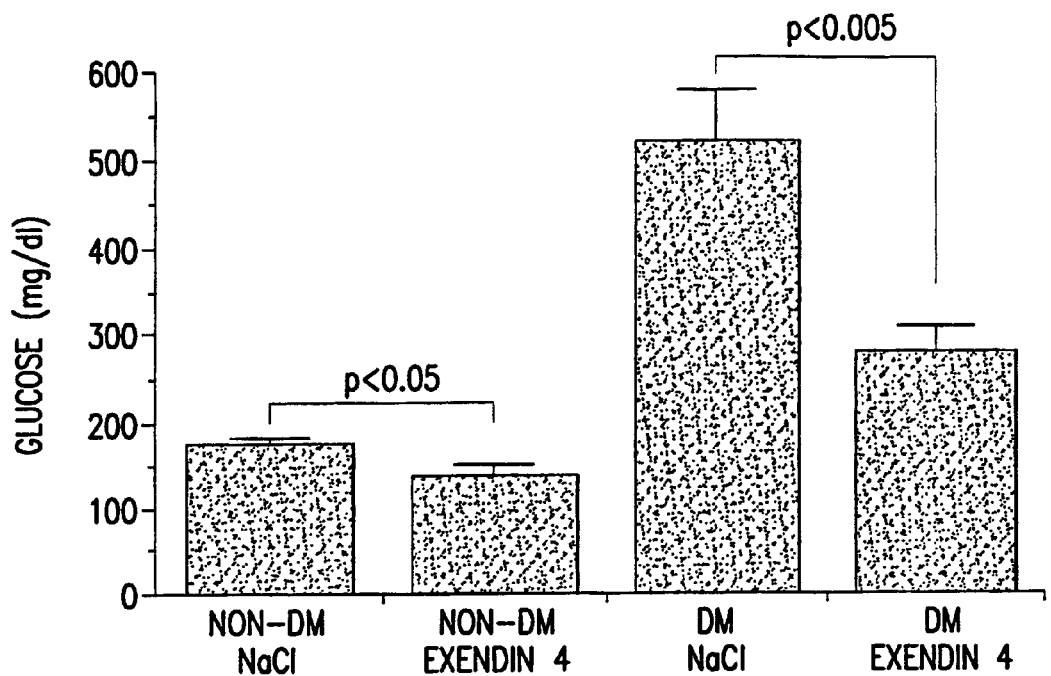
FIG. 13 shows fasting glucose and insulin concentrations in the diabetic and non-diabetic mice given either exendin-4 (24 nmol/kg) or normal saline intraperitoneally daily for 12–13 weeks. Values are expressed as mean±SEM (n=9–10 per group).
Figure 13B:
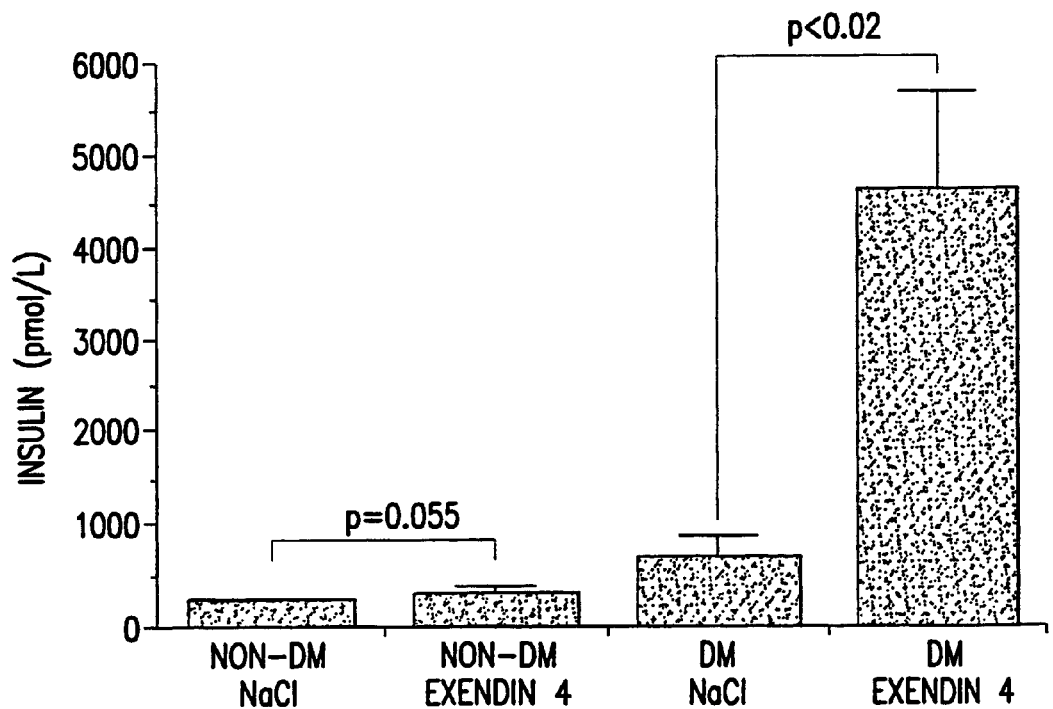

We assayed the whole blood of the saline and exendin-4-treated animals for Hb A1c determinations and we measured plasma for glucose and insulin concentrations after an overnight fast (FIG. 12). It can be seen that all these parameters were significantly altered by the daily exendin-4 treatment. Hb A1c was 8.8% in the NaCl-treated diabetic animals vs 4.7% in the exendin-4-treated animals ($p<0.0001$). Hb A1c was also lower in the non-diabetic animals, 3.5 vs. 3.1% ($p=0.0002$), exendin-4-treated vs. NaCl-treated, respectively. Glucose levels were significantly lower (278.7±30.0 vs. 517±59 mg/dl, $p<0.005$) and insulin levels significantly higher (4,600±1,114 vs. 707.2±169.7 pmol/l, $p<0.02$) in the exendin-4-treated diabetic animals (FIG. 13). The trends in glucose and insulin were the same in the non-diabetic animals with exendin-4 treatment though not as dramatic (FIG. 13).

In the eight diabetic mice that were 14 weeks old when their treatment began, blood sugars were 640±37 mg/dl in the NaCl-treated animals and 355± 21 mg/dl in the exendin-4-treated animals after five days. Their insulin levels were 6,904±705 vs. 1,072±54 pmol/l, exendin-4-treated vs. NaCl-treated, respectively.

Following sc and ip exendin-4, blood sugars in diabetic mice had a much more prolonged biological response in that the blood sugars stayed lower longer (up to 24 hours after an ip dose) than was expected from the insulin response to the iv exendin-4, with the glucose lowering effect of the ip injections being less variable than sc. This was possibly due to greater variation in the sc technique and perhaps even loss of the peptide during injections in some cases.

In the studies involving ip injection of exendin-4 ip for one week daily, the fasting blood sugars as a result of just one injection a day were actually lower than the blood sugars of the non-diabetic animals. It was also obvious looking at the cages each morning which diabetic animals were receiving exendin-4 as their cages were always drier. This effect was also seen in the non-diabetic animals that received exendin-4.

In the experiments where exendin-4 was given daily for five days to diabetic animals whose mean blood sugars were 640 mg/dl, there was also a marked effect on lowering blood sugar, and insulin levels were markedly increased. This is unlikely due to expansion of the beta cell mass and would suggest that beta cells of diabetic rats are still responsive to exendin-4 even in the face of such marked hyperglycemia.

Even after 12 weeks of exendin-4, blood sugars were lower than in the NaCl-treated animals. Typically primary antibody responses post intraperitoneal injections take up to 14–21 days and exendin-4 is a weak hapten at any rate. So for the first several weeks of treatment exendin-4 would not be expected to be neutralized by antibody. In conjunction with this, exendin-4's biological effects are at very low concentrations and therefore possibly the peptide has a higher affinity for the GLP-1 receptor than for its specific antibody and so might not be totally neutralized by antibody. Other possibilities as to why exendin-4 might not be neutralized are that there is an exendin-4-like peptide produced in rodents that are not yet identified or that an exendin-4-type molecule is made in utero in rodents which would render mature animals exendin-4-tolerant.

We have given exendin-4 at a lower concentration (1 nmol/kg) ip for one week to diabetic mice. It was just as effective at lowering blood sugar as at the larger amount reported in this example.

We saw no untoward effects of the daily injections on the behavior of the mice. We have since observed that for the first 3–4 days of injection of exendin-4 the weight of the animal drops but by the seventh day it is back to the same as NaCl-treated animals. In our long-term study we weighed weekly and so missed the initial drop. Except for the bedding being obviously drier each morning in the treated diabetic animals, we could not detect any glaring deleterious effects of exendin-4 on the animals. We therefore suggest that exendin-4 might be superior to GLP-1 as a treatment for Type 2 diabetes in humans.

Example 3

Using the protocol of Example 1, GLP-1 was administered by continuous infusion for one to five days to young and old rats, whereas control rats received comparable saline infusions. Exendin-4, in contrast, was administered intraperitoneally one time daily for five days according to the protocol of Example 2.

Approximately 20% of the cells in the GLP-1 treated pancreata were positive for PCNA at five days. At the same time point, there were proliferating cells in the islet. In addition, there were proliferating cells lining the ducts and, more surprisingly, in the acinar tissue, an area generally considered to be devoid of stem cells. Also surprisingly, a number of insulin positive cells were found outside the islets among the acinar tissue, where insulin positive cells are not expected.

These results show that continuous infusion with GLP-1 or repeated intraperitoneal injection with Exendin-4 for at least two days results in an increase in total number of insulin positive cells and in differentiation of acinar cells into insulin, IDX-1 positive cells. These results further suggest that GLP-1 and Exendin-4 increase the proliferation of cells and, specifically, an increase in proliferation of insulin producing cells within the acinar tissue.

Continuous infusion of GLP-1 promotes differentiation of non-insulin producing cells into insulin producing cells upon contacting the non-insulin producing cells with GLP-1 for greater than twenty-four. The effect was observed as early as 1 day, and the maximal effect as early as seven days. Such differentiation was surprising since the prior art showed only insulinotropic results in beta cells. Furthermore, the present invention was surprising because acinar cells, which have never been shown to be capable of producing insulin, are promoted to secrete insulin upon contact with GLP-1. The increased number of insulin producing cells remains unchanged for at least two weeks after treatment is discontinued. Since differentiation to an insulin producing cell is a terminal event, de-differentiation back into a non-insulin producing cell at even later time points is unlikely. Thus, the effect is permanent.

Exendin-4 is shown in the present invention to have the same effects as GLP-1 on the differentiation of insulin producing cells from non-insulin producing cells. Surprisingly, Exendin-4 is shown to have a much longer half-life than GLP-1. The increase in the number of insulin producing cells, thus, can be achieved with daily bolus injection, rather than continuous infusion, of Exendin-4 for two days. After two injections, insulin producing cells outside the islet are observed. The maximal effect is achieved by seven days. As with GLP-1, the effect persists for at least two weeks, and probably permanently, even after contact with the Exendin-4 is discontinued.

GLP-1, Exendin-4, growth factors having amino acid sequences substantially homologous to GLP-1 or Exendin-4, and fragments thereof affect the differentiation of non-insulin producing cells in vivo and in vitro. Furthermore, a variety of non-insulin producing cells, including stem cells and acinar cells can be promoted to differentiate into insulin producing cells. These advances over the prior art provide methods of treating diabetes mellitus whereby insulin producing cells are increased in number by administration of the growth factor to a patient or by contacting the non-insulin producing cells in vitro.

Example 4

The purpose of this study was to determine if GLP-1 and the islet hormones, glucagon and insulin, have effects on acinar tissue. We used the AR42J cells (Christophe, 1994), which are derived from a rat pancreatic exocrine tumor, as a model of acinar tissue. We then looked at some aspects of the signal transduction system through which GLP-1 is already known to work in beta cells (Goke et al., 1993; Holz et al., 1995; Yada et al., 1993).

Materials. GLP-1, glucagon, exendin-4 and exendin 9–39 were obtained from Bachem (Torrance Calif.). Cholecytokinin (CCK), insulin, genestein and vanadate were from Sigma Chemical Co (St. Louis, Mo.). The rat pancreatic cell line, AR42J, was from American Type Culture Collection (Rockville, Md.). Anti-tyrosine antibodies were purchased from Upstate Biotechnology, Inc (Lake Placid, N.Y.).

Cell Culture. AR42J cells were maintained in Dulbecco's modified Eagle's medium (Gibco, Grand Island, N.Y.) (DMEM) supplemented with 10% Fetal Calf Serum, 100 IU/ml penicillin, 100 µg/ml streptomycin and 2 mM glutamine. Cells from passage 23–36 were used throughout this study. Cells were routinely plated at about $10^5$ cells/ml in 12-well cluster dishes and incubated in a humidified incubator at 37° C. with 95% air and 5% $CO_2$. As AR42J cells responded poorly to CCK we routinely incubated the cells with 10 nM dexamethasone for 48 h before use as this was known to induce CCK responsivity in a concentration-dependent manner (Logsdon et al., 1987).

Amylase Assay. For amylase secretion, cells were washed free of medium with 2 ml phosphate buffered saline (PBS). Incubation was then carried out in DMEM containing 15 mM HEPES, 0.2% bovine serum albumin (BSA) and 0.01% soybean trypsin inhibitor. The hormones and reagents of interest were added for 50 min at 37° C. The incubation medium was then immediately removed for amylase determination and the cells were again washed in 2 ml ice-cold PBS. Lysate buffer containing (in mM) 130 Tris-HCl, 10 $CaCl_2$, 75 NaCl, and 0.2% Triton X-100 (pH 8.0) was added to the cells and the lysates were then collected for total amylase activity (Ceska et al., 1969). The released amylase was expressed as the percentage of the total amylase activity of the cells.

Measurement of cAMP. Cells were grown in 12-well dishes and treated with hormones and reagents±IBMX as described above. They were then washed 3 times in ice-cold PBS and lysed with 1 ml ice-cold 0.6 mM perchloric acid. The lysates (950 µl) were transferred to microcentrifuge tubes and the pH adjusted to 7.0 using 5 M $K_2CO_3$. After centrifugation for 5 min at $10^4$ rpm, the supernatant was vacuum dried, and then recovered in 200 µl Tris/EDTA buffer. After addition of 0.15 mM $Na_2CO_3$ (50 µl) and 0.15 mM $ZnSO^4$ (50 µl), followed by incubation for 15 min on ice, the salt precipitate was removed by centrifugation for 15 min at $3.5 \times 10^3$ rpm and 50 µl of supernatant was assayed using a cAMP [$^3$] assay kit (Amersham Corp., Arlington Heights, Ill.), (Steiner et al., 1972). Cellular protein was measured using the Bradford method (Bio-Rad, Richmond, Calif.) with bovine gamma-globulin as standard (Bradford, 1976).

Measurement of intracellular calcium, $[Ca^{2+}]_i$. AR42J cells were loaded with the fluorescent $Ca^{2+}$ probe, indo-1 acetoxymethyl ester (indo-1/AM). The loading solution consisted of 50 µg of indo-1/AM (Molecular Probes Inc.), 30 µl of dimethyl sulphoxide (DMSO) and 5 µl of 25% (w/w in DMSO) Pluronic F-127 (BASF Wyandott Corp.) This mixture was added to 2.0 ml of cells in Hank's balance salt solution (final indo-1 concentration of 25 µM) and gently mixed on a shaking plate for 1 h. The cells were then centrifuged at 400×g for 60 sec, resuspended in standard bathing solution, consisting of (in mM): 137 NaCl; 5 KCl; 1.3 $MgSO_4$; 5 $CaCl_2$; 20 HEPES; pH adjusted with NaOH to 7.4, and stored for at least 1 h before use. Both loading with indo-1 and the experiments were carried out at room temperature (22–24° C.). The cell suspension was placed in a chamber on the stage of an inverted fluorescence microscope (Spurgeon et al., 1990). The emission field was restricted to a single cell. Indo-1 was excited at 350±5 nm every 5 ms, and the fluorescence emission was split into wavelength bands of 410±5 and 490±5 nm. The 410:490 fluorescence ratio (ratio F410/F490), corrected for auto fluorescence, was used as an index of $[Ca^{2+}]_i$, using the methodology well know in the art (Spurgeon et al., 1990). The cell autofluorescence was assessed in a large number of indo-1 non-loaded cells from the same batch. In a typical experiment, the standard bathing solution was exchanged rapidly (<200 ms) with one of the test solutions injected from a micropipette placed in close vicinity to the cell (Janczewski et al., 1993; Konnerth et al., 1986). Routinely, the cells were exposed to the test solution for 240–300s.

Thereafter, the test solution was washed out, while $[Ca^{2+}]_i$ was monitored for additional 120–180s. The test solutions were prepared just prior to the experiment by adding the hormones in standard bathing solution.

GLP-1 binding. AR42J cells were plated and cultured as described above. At the start of the binding experiment the cells were incubated with serum-free DMEM for 2 h at 37° C. Cells were then washed twice with 0.5 ml binding buffer containing (in mM) 120 NaCl, 1.2 $MgSO_4$, 13 sodium acetate, 5 KCl, 10 Tris, pH 7.6. Cells were then incubated overnight at 4° C. with 0.5 ml binding buffer supplemented with 2% BSA, 500 U/ml aprotinin, 10 mM glucose, a range of concentrations of GLP-1 (0.03 nM–100 nM) and 30,000 cpm $^{125}$I-GLP-1 (2,000 Ci/mmol, Peninsula, Belmont, Calif.). We only used freshly prepared $^{125}$I-GLP-1 within two weeks of the reference date. At the end of the incubation, the supernatant was discarded and the cells were washed three times with ice-cold PBS. Cells were lysed with 0.5 ml 0.5 N NaOH/0.1% SDS for 30 min at room temperature. The radioactivity was measured in the lysates in an ICN Apec series gamma counter. Specific binding was determined by subtracting the non-specific binding present at 500 nM GLP-1 from total binding. This method has been used previously to characterize GLP-1 binding in CHO cells overexpressing GLP-1 receptor and in 3T3-L1 adipocytes (Montrose-Rafizadeh et al., *J. Biol. Chem.*, 1997; Montrose-Rafizadeh et al., *J Cell Physiol.*, 1997).

RT-PCR of the GLP-1 Receptor. Complementary DNA was synthesized from total cellular RNA using Maloney murine leukemia virus reverse transcriptase (Bethesda Research Laboratories, Gaithersburg, Md.) and random hexanucleotide primer (Pharmacia LKB Biotechnology Inc., Piscataway, N.J.). PCR amplification (30 cycles) was performed (Saiki et al., 1997) from first strand cDNA using recombinant Taq DNA polymerase (Amplitaq, Perkin-Elmer, Cetus). Oligonucleotide primers were on 5'- and 3'-end of the pancreatic GLP-1 receptor sequence (Thorens, 1992), 5'ACAGGTCTCTTCTGCAACC3' and 5'AAGATGACTTCATGCGTGCC3', respectively. PCR products were then resolved on a 1% agarose gel and visualized using ethidium bromide. The PCR products were subcloned in pBluescript vector and sequenced using the chain termination technique and Sequenase 2.0 kit (United States Biochemicals, Cleveland, Ohio). The specificity of the PCR product was also determined by the Bstx1 restriction enzyme.

Immunoprecipitation and Western blotting of the GLP-1 receptor. AR42J cells and an insulinoma cell line, RIN 1046-38 cells, were grown in 60 mm dishes as described above. When the cells reached 80% confluence, they were washed twice with Krebs-Ringer buffer containing 115 mM NaCl, 5 mM KCl, 2.5 mM $CaCl_2$, 1 mM $MgCl_2$, 24 mM $NaHCO_3$, and 25 mM HEPES and frozen in liquid nitrogen. The frozen cells were scraped and lysed in RIPA buffer containing 20 mM Tris-HCl: pH 8.0, 137 mM NaCl, 1% Triton X-100, 0.5% deoxycholate, 0.1% SDS, 0.2 mM PMSF, 10 µg/ml leupeptin, 20 µg/ml aprotinin, 1 mM Na-orthovanadate, 1 mM benzamidine. Insoluble material was removed by centrifugation at 15,000×g for 15 min at 4° C. and the supernatant was collected for immunoprecipitation and Western Blotting. Anti-GLP-1-R antibody against the N-terminal (gift from Dr. Joel Habener, Massachusetts General Hospital, Mass.) at 1:250 was added to each tube, together with 40 µl protein A and protein G. The immunoprecipitation was carried out at 4° C. overnight and the immunocomplexes were washed twice with RIPA buffer, rewashed another two times with washing buffer (25 mM Hepes, 0.1% Triton X-100 and 1 mM Na-orthovanadate), then the immunocomplex pellets were solubilized in 50 µl of SDS-PAGE sample buffer at 70° C. for 10 min. The immunoprecipitated proteins were eluted with mini-resin column and subjected to 4–20% SDS-polyacrylamide gel. After the gel was electrotransferred to PVDF membrane, the blot was blocked with 5% non-fat milk in TBST buffer (20 mM Tris-HCl [pH 7.5], 137 mM NaCl and 0.1% Tween 20) for 1 h at room temperature, and then incubated with antibody to GLP-1-receptor at 1:1500 for 1 h at room temperature. PVDF membranes were washed three times with TBST and incubated with horseradish peroxidase-conjugated anti-rabbit secondary antisera for 1 h at room temperature. After a series of washes in TBST, the blots were developed using the EC1 chemiluminescent detection system. Autoradiographs were quantified using Image-Quant™ software (version 3.3) on a Molecular Dynamics laser densitometer. In this experiment, the insulin producing cell line RIN1046-38 cells was used as a positive control for the presence of the GLP-1 receptor. Aliquots (20 µl) of clarified cell lysates were used to determine protein concentration which was estimated by the Bradford method (Bradford, 1976).

Tyrosine Phosphorylation Studies. AR42J cells were pre-incubated in Krebs-Ringer Balanced Buffer (KRBB) containing 115 mM NaCl, 5 mM KCl, 2.5 mM $CaCl_2$, 1 mM $MgCl_2$, 24 mM $NaHCO_3$, and 25 mM HEPES for 2 h at 37° C. Then the medium was removed and fresh KRBB was added, followed by placing the cell on a 37° C. hot plate for 5 min. After addition of various reagents (see FIG. 24) for 5 min the reaction was terminated by submersion of the dishes in liquid nitrogen. The frozen cells were scraped and lysed in RIPA buffer. Insoluble material was removed by centrifugation at 15,000×g for 15 min and the supernatant was collected for immunoprecipitation and immunoblotting. Phosphotyrosine-containing proteins from the clarified lysates were immunoprecipitated with monoclonal anti-phosphotyrosine antibody and separated by electrophoresis in 4–12% SDS-polyacrylamide gels under reducing conditions followed by electrotransfer to PVDF membrane and immunoblotting with a polyclonal anti-phosphotyrosine antibody. The blots were developed using the ECL chemiluminescence detection system (Amersham). Total protein content in the clarified cell lysates was assayed using the Bradford method (Bradford, 1976).

Statistical Analysis. Where applicable results were expressed as the mean±SEM and subjected to unpaired Student's t test. Within group comparisons were analyzed using one-way analysis of variance (ANOVA). $p<0.05$ was considered statistically significant.

Figure 14:
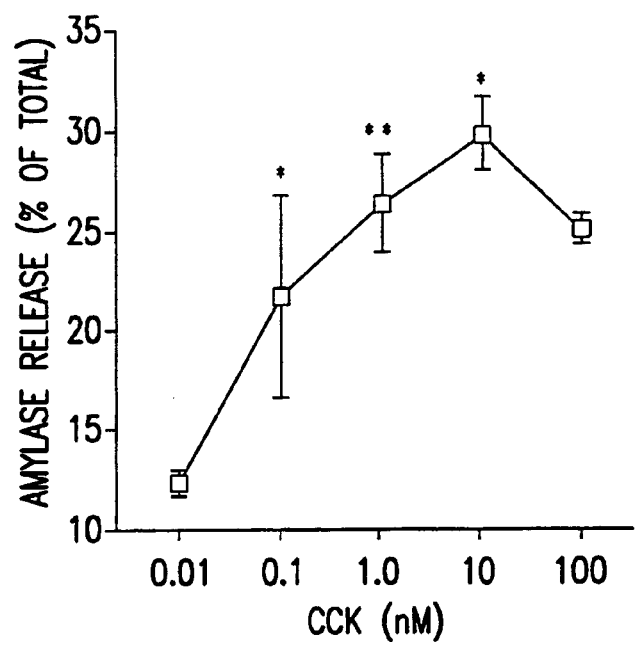
FIG. 14 shows CCK concentration-response curve of amylase release from AR42J cells. Cells were treated with CCK at the concentrations shown for 50 min. Amylase values are expressed as a percentage of the released amylase into the medium over the total amylase activity of the cells. Results are the mean±SEM of 15 experiments.
Figure 15:
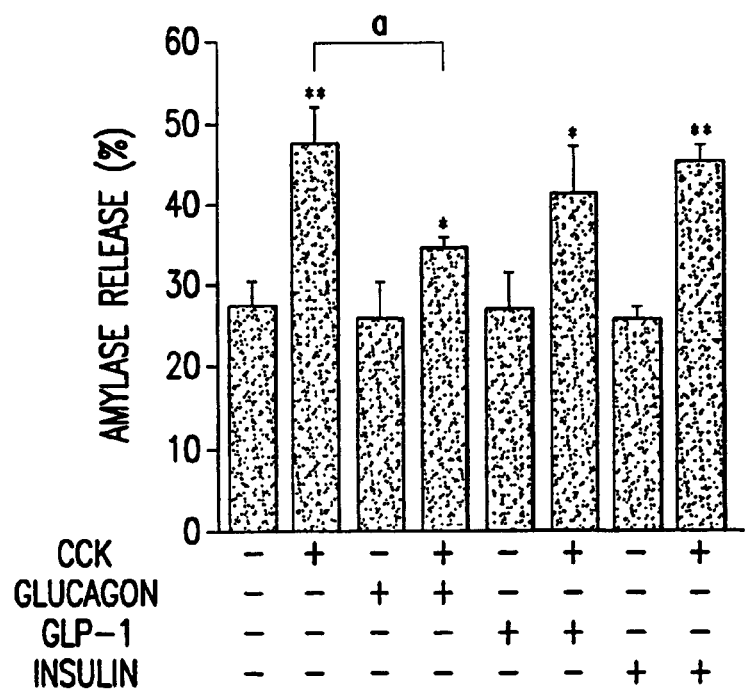
FIG. 15 shows the effects of glucagon (10 nM), GLP-1 (10 nM), and insulin (100 nM)±CCK (1 nM), on amylase release from AR42J cells. Dexamethasone-induced AR42J cells were incubated for 50 min in presence of the hormones. Amylase values are expressed as a percentage of the released amylase into the medium over the total amylase activity of the cells. Results are mean±SEM of 20 experiments, * $p<0.05$, **$p<0.01$, treatment vs. no treatment. a=$p<0.01$.
Figure 16:
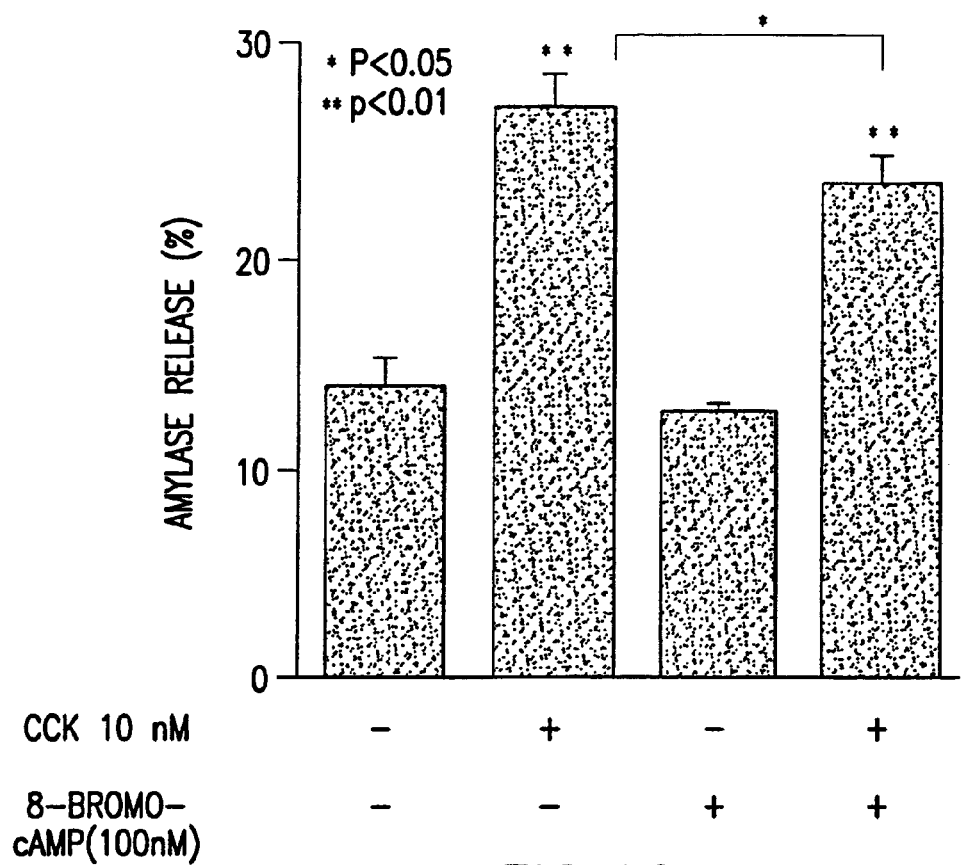
FIG. 16 shows the effect of 50 min of treatment with 8-Bromo-cAMP (100 nM) on amylase release from AR42J cells. Amylase values are expressed as a percentage of the released amylase into the medium over the total amylase activity of the cells. Results are mean±SEM of 3 experiments, * $p<0.05$, treatment vs. no treatment.
Figure 17:
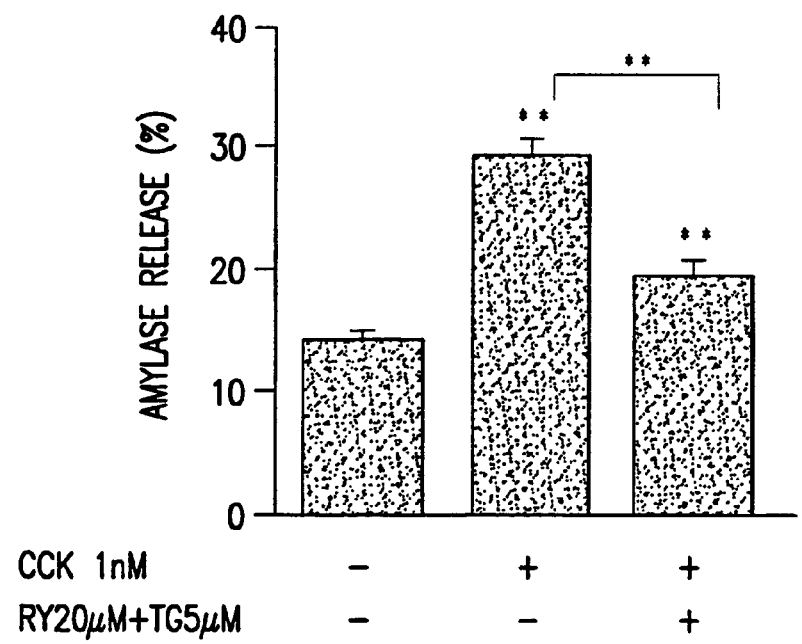
FIG. 17 shows the effects of ryanodine (RY) and thapsigargin (TG) in the presence or absence of CCK on amylase release from AR42J cells. Amylase values are expressed as a percentage of the released amylase into the medium over the total amylase activity of the cells. RY and TG were added 30 min prior to addition of CCK, which was then added for 50 min. Results are mean±SEM of 3 experiments, **$p<0.01$.
Figure 18:
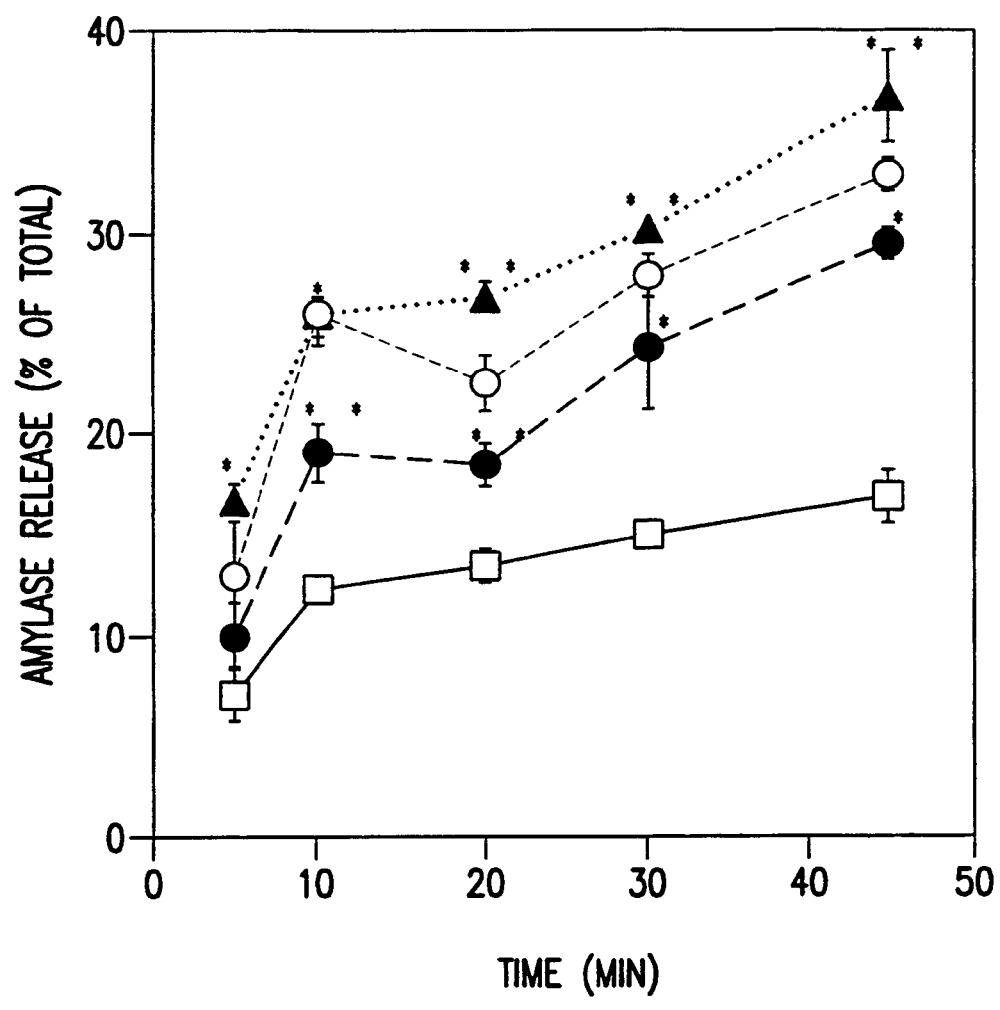
FIG. 18 shows the time course of the actions of vanadate (1 mM) (Δ) and genestein (300 μM) (●) on CCK (1 nM)-mediated amylase release from AR42J cells. Amylase release from CCK-treated (1 nM) (○) cells or control (no treatment) (□) cells is also shown. Amylase values are expressed as a percentage of the released amylase into the medium over the total amylase activity of the cells. Results are the mean±SEM of 4 experiments. * $p<0.05$, **$p<0.01$, vanadate or genestein plus CCK treatment vs. CCK treatment alone.

Amylase release. CCK was a potent stimulus of amylase release. Maximum stimulation was seen at 10 nM (FIG. 14). Although glucagon (10 or 100 nM) by itself had no effect on amylase release, when combined with CCK it inhibited, but did not fully abolish, CCK-induced amylase release (FIG. 15; n=20, p<0.01). GLP-1 and insulin, either alone or combined with CCK, did not influence amylase release (FIG. 15). We also examined exendin-4 (concentrations ranging from 10 nM to 10 nM) for potential effects on amylase release, and, similar to GLP-1, it did not appear to influence amylase release. As GLP-1 and glucagon might be expected to raise cAMP levels in AR42J cells we looked at the effect of 8-Bromo-cAMP (8-Br-cAMP), a cAMP analog, on amylase release to look for specific cAMP effects. While 8-Br-cAMP appeared to have no effect on amylase release when given alone, it reduced CCK-induced amylase release (FIG. 16). We also used thapsigargin and ryanodine, specific inhibitors of ryanodine receptors/ER $Ca^{2+}$ release channels and of the ER $Ca^{2+}$ pumps, respectively, alone and in combination with CCK, to investigate the role of a rise of intracellular calcium on amylase release. The combination of thapsigargin and ryanodine decreased, but did not fully inhibit, CCK-induced amylase release (FIG. 17; n=3, p<0.01). Naf, which mimics CCK's effects on amylase release in acinar tissue (Vajanaphanich et al., 1995), did like-wise in the AR42J cells. Genestein (300 µM), the tyrosine kinase inhibitor, decreased CCK-mediated amylase release, especially at the early time points of the CCK treatment, while vanadate, the tyrosine phosphatase inhibitor, increased significantly basal and CCK-mediated amylase release (FIG. 18). We have shown that when beta cells of the pancreas are treated with GLP-1 for 24 h there is an increase in glucose- and GLP-1-mediated insulin release (Wang et al., *Endocrinology*, 1995). We therefore looked for any long-term effects GLP-1 might have on amylase release. Pre-incubation of AR42J cells for 8, 24, 48 or 72 h with GLP-1 (10 nM) and insulin (100 nM) did not increase basal or CCK (1 nM)-induced amylase release.

$[Ca^{2+}]_i$ responses to CCK in AR42J cells. Under the present experimental conditions, most (85%; n=35) of the AR42J cells responded to 1 nM CCK with a transient increase in $[Ca^{2+}]_i$. FIG. 6A shows a representative example of the CCK-induced $[Ca^{2+}]_i$ transients, which commenced after 5–25 seqs following exposure to CCK and peaked within the next 5–15 secs. The peak $[Ca^{2+}]_i$, assessed from the peak indo-1 fluorescence ratio (IFR), exceeded the resting IFR by 2.5–3.5 fold. Relaxation of the $[Ca^{2+}]_i$ transients commenced immediately following the peak and usually consisted of an initial rapid phase, followed by a plateau and a slower final phase. After the $[Ca^{2+}]_i$ transient, baseline $[Ca^{2+}]_i$ decreased below the level of resting $[Ca^{2+}]_i$, measured prior to the exposure to CCK (FIG. 19A). During the subsequent rest, baseline $[Ca^{2+}]_i$ showed a gradual increase, but usually did not fully recover to the control levels within 10 min. $[Ca^{2+}]_i$ transients elicited by a repeated exposure to CCK prior to a full recovery of resting $[Ca^{2+}]_i$ were reduced by 30–40% vs. the preceding $[Ca^{2+}]_i$.

The CCK-induced $[Ca^{2+}]_i$ transients were almost completely abolished in cells pretreated with 10 µM ryanodine and 500 µM thapsigargin (FIG. 19B; n=7). These results support the concept that in acinar cells, the ER is the major source of changes in $[Ca^{2+}]_i$ induced by CCK (Muallem et al., 1988; Ochs et al., 1983). Consistent with this idea, exposures to CCK added to a nominally $Ca^{2+}$-free superfusing solution (FIG. 19C) did not appreciably affect the rate of rise or the magnitude of the $[Ca^{2+}]_i$ transients (n=5). However, as shown in FIG. 19C, a reduction in the extracellular $Ca^{2+}$ shortened the duration of the $[Ca^{2+}]_i$ transients, suggesting, as shown before (Muallem et al., 1988); Ochs et al., 1983), that extracellular $Ca^{2+}$ may play a role in sustaining the delayed component of the $[Ca^{2+}]_i$ transient initiated by CCK-induced ER $Ca^{2+}$ release.

$[Ca^{2-}]_i$ responses to GLP-1 in AR42J cells. Exposure to GLP-1 elicited $[Ca^{2+}]_i$ responses in approximately 50% (n=27) of AR42J cells. The GLP-1-induced transients (FIG. 20A) displayed considerable variability, but usually developed at a slower rate and attained smaller amplitudes (1.5–2.5 fold increase over resting IFR) than the $[Ca^{2+}]_i$ responses to CCK. Moreover, the GLP-1-induced $[Ca^{2+}]_i$ transients relaxed at a slower rate than those induced by CCK (FIGS. 20A vs. 19A and 20B,C). FIG. 20B shows the effects on $[Ca^{2+}]_i$ of CCK applied<10 min after an exposure to GLP-1 in the same cell. In experiments of this type, the CCK-induced transients retained their characteristic configuration (as in FIG. 19A) but reached smaller amplitudes.

Figure 19:
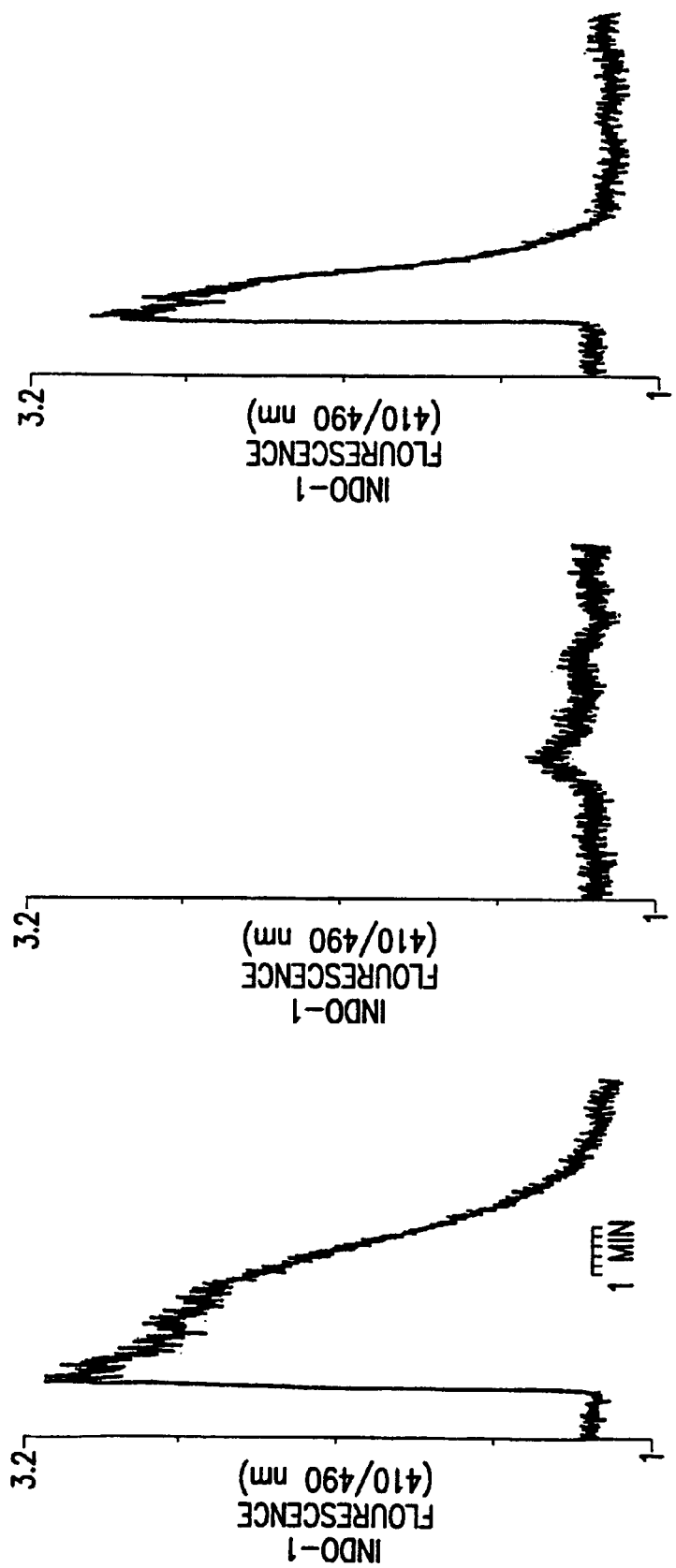
FIG. 19 shows the effects of CCK on intracellular free $[Ca^{2+}]_i$ in single AR42J cells. The bar indicates the time of exposure to 10 nM CCK in three different cells.
Figure 20:
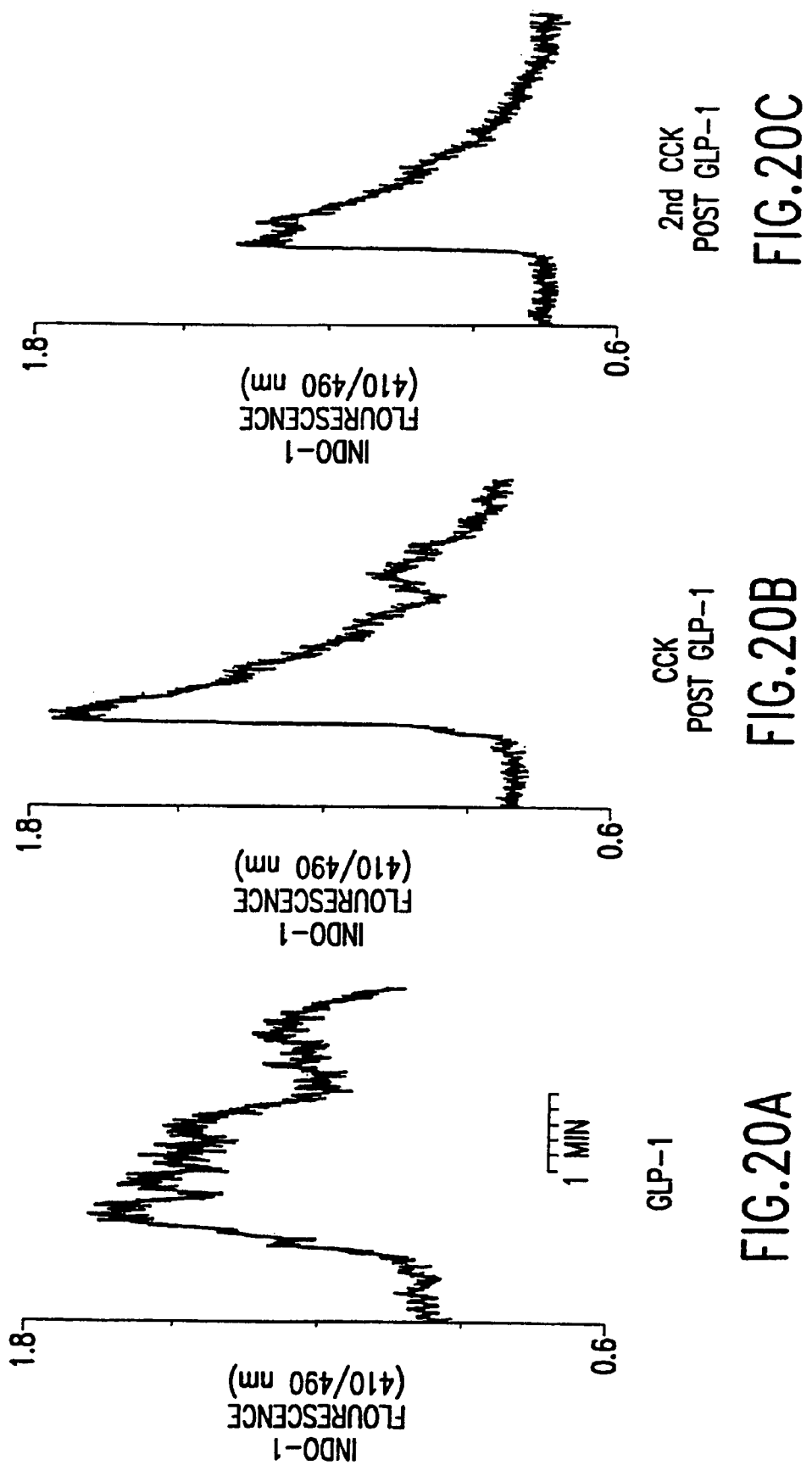
FIG. 20 shows the effects of GLP-1 on $[Ca^{2+}]_i$ and CCK-induced $[Ca^{2+}]_i$ transients in single AR42J cells. The same cell was studied in A–C.

The latter effect can be attributed, at least in part, to a reduction of the $[Ca^{2+}]_i$ content, indicated by a reduction in the baseline IFR, and/or partial depletion of the ER $Ca^{2+}$ content (see FIG. 19). On exposure to CCK for a second time the amplitudes were even smaller (FIG. 20C). Pretreatment with ryanodine (100 μM) and thapsigargin (500 μM) virtually abolished $[Ca^{2+}]_i$ responses to GLP-1. Taken together, these results indicate that CCK and GLP-1 have access to the same intracellular pools of $Ca^{2+}$, presumably the ER, but perhaps release $Ca^{2+}$ by differing mechanisms. Exendin-4, the GLP-1 homolog from Gila monster, had identical effects as GLP-1 on $[Ca^{2+}]_i$ but was approximately one order of magnitude more potent. The GLP-1 antagonist, exendin 9–39 (Goke et al., 1993), inhibited GLP-1-induced calcium transients when used at a 10-fold higher concentration than GLP-1.

Figure 21:
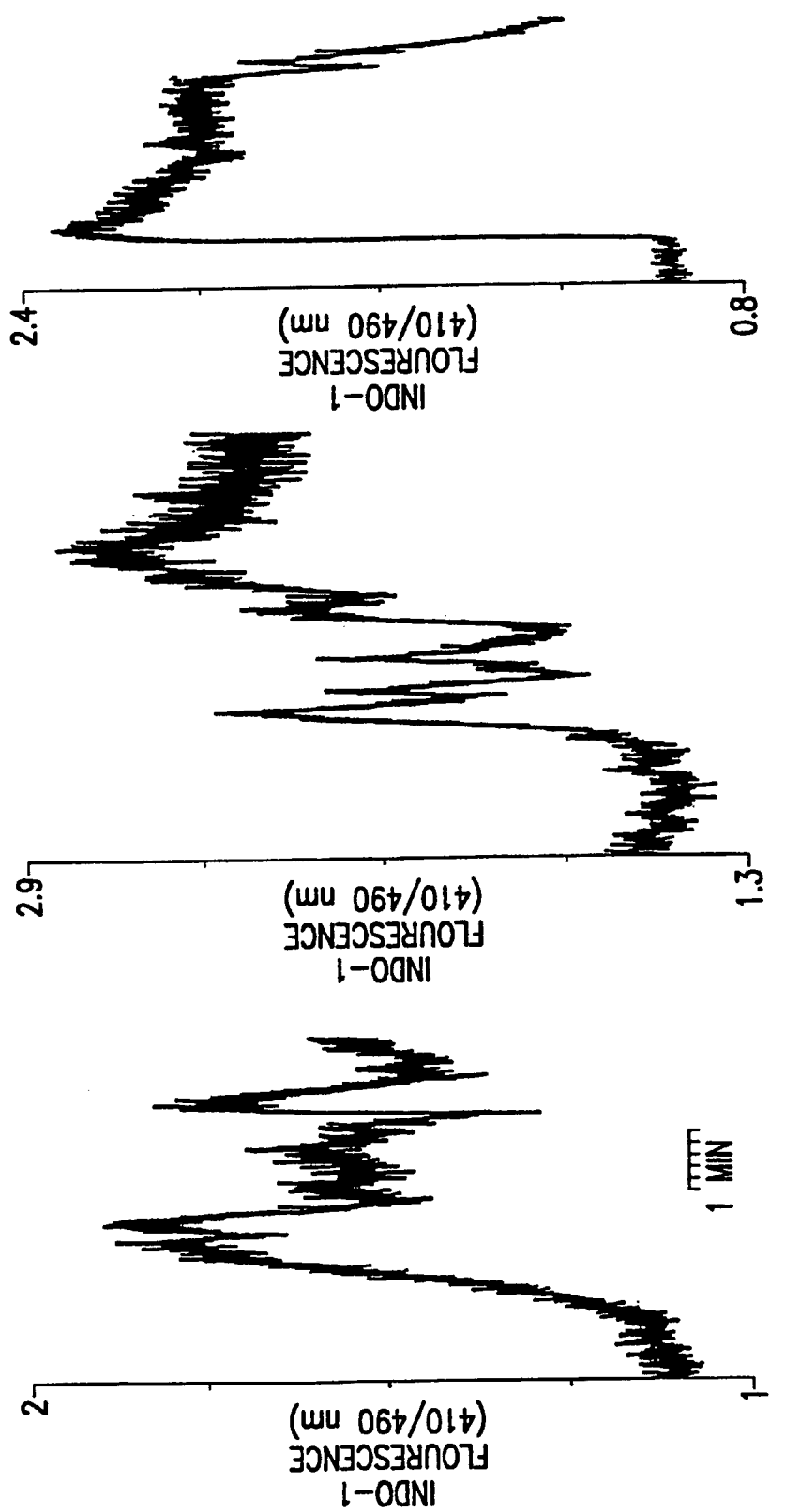
FIG. 21 shows the effects of glucagon and 8-bromo-cAMP (8BcAMP) on $[Ca^{2+}]_i$ in single AR42J cells.

Effects of glucagon and 8-bromo-cAMP on $[Ca^{2-}]_i$ AR42J cells. Exposures to glucagon (10 nM) induced $[Ca^{2+}]_i$ responses in 70% (n=12) of AR42J cells. The $[Ca^{2+}]_i$ transients commenced briefly after exposure to glucagon, developed at a relatively slow rate, peaked at 200–250% of the resting IFR level and showed a prolonged, slow relaxation (FIG. 21A). The $[Ca^{2+}]_i$ transients induced by CCK shortly after treatment with glucagon (or with both treatments added simultaneously) showed an attenuated rate of rise and a very slow rate of relaxation (FIG. 21B). Similarly, brief (60–300 sec) exposures to 0.1 μM 8-bromo-cAMP, a membrane-permeable form of cAMP, usually did not markedly affect the rate of rise of the CCK-induced $[Ca^{2+}]_i$ transients but markedly slowed their rate of relaxation (FIG. 21C). A reduction in intracellular mobilization of $[Ca^{2+}]_i$ with the acetoxymethyl ester of dibutyryl cAMP in the presence of CCK has previously been shown in acinar cells (Kimura et al., 1996).

Figure 22:
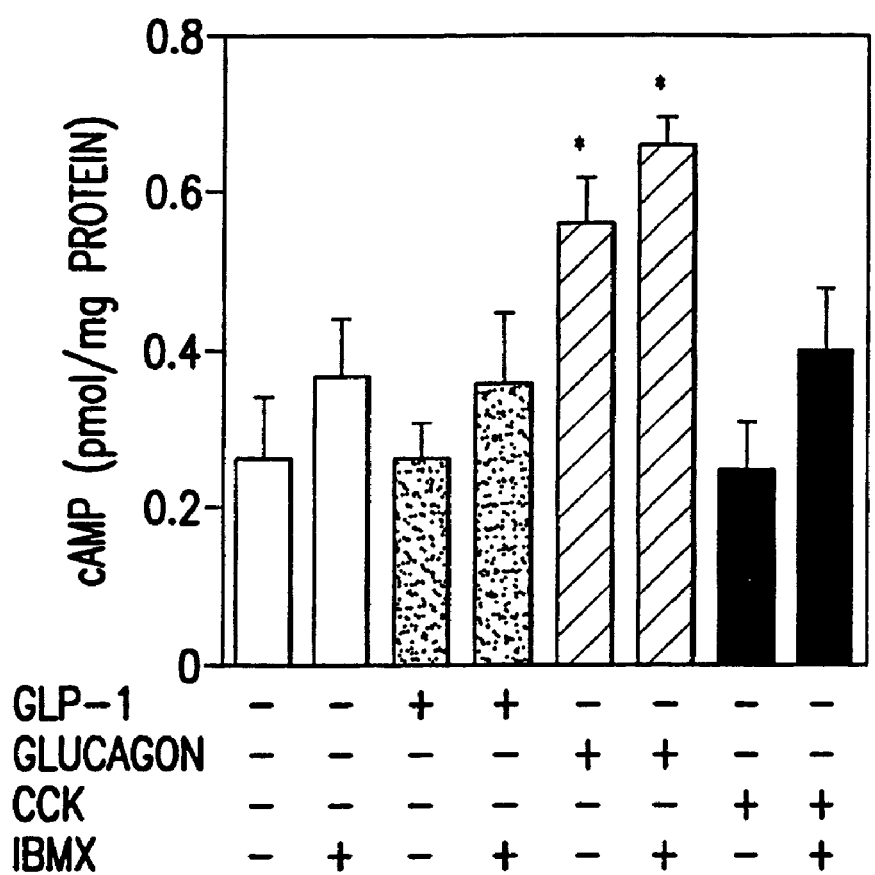
FIG. 22 shows the effects of GLP-1 (10 nM), glucagon (10 nM) and CCK (1 nM) treatment±IBMX (100 nM) for 50 min on intracellular cAMP levels in AR42J cells. Results are mean±SEM of 3 experiments, *$p<0.05$.

GLP-1 Binding. Specific $^{125}$I-GLP-1 binding, as determined by displacement of total binding by the presence of 500 μM cold GLP-1, was 0.64±0.16% (n=9, the amount of specific binding was significantly greater than zero, p<0.01) of total radioactivity added and 27±3.2% (n=9) of total binding. Because of the low specific binding, a full Scatchard analysis was not performed.

cAMP levels. Intracellular cAMP levels were not altered in AR42J cells by 1 h treatment with GLP-1 (0.1 to 100 nM) or IBMX (100 nM) in the presence or absence of CCK (1 nM), or with CCK (0.1 to 100 nM) alone. While IBMX caused a slight increase in cAMP levels, in 3 experiments it was not statistically different from non-IBMX-treated cells. Glucagon (10 nM) caused a 2-fold increase in cAMP levels in the presence and absence of CCK (FIG. 22). Exendin-4 (0.1 to 10 nM) did not alter cAMP levels.

Figure 23:
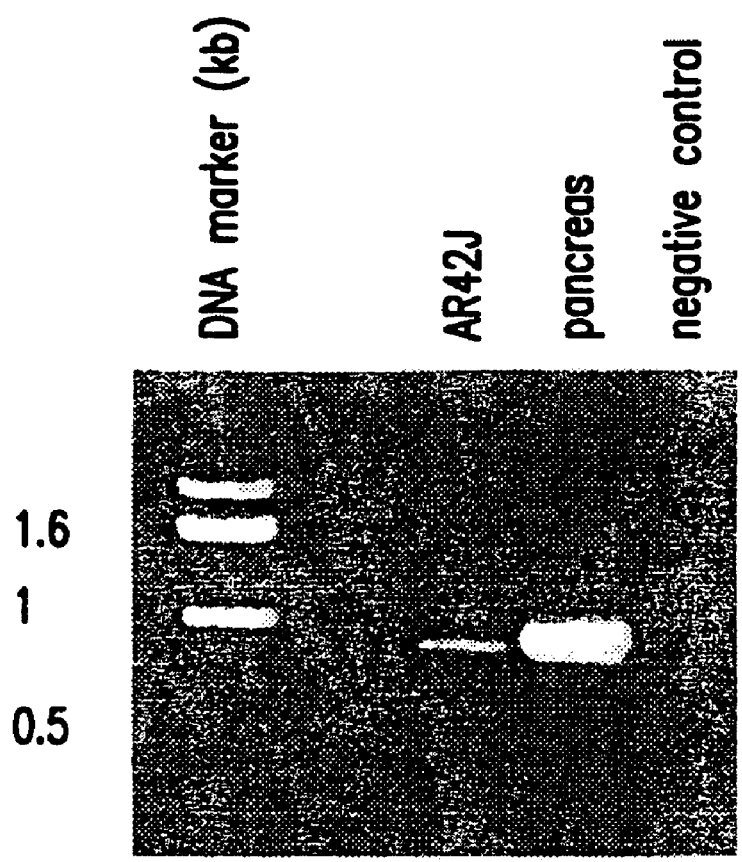
FIG. 23 shows RT-PCR of GLP-1 receptors in AR42J cells and rat pancreas. cDNA was amplified for 30 cycles using primers in the 5'-and 3'-end of the rat pancreatic GLP-1 receptor. PCR products were resolved on a 1% agarose gel and visualized using ethidium bromide. From left to right; Lane 1, DNA marker; Lane 2, blank; Lane 3, AR42J cells; Lane 4, rat pancreas; Lane 5, water control. In Lanes 3 and 4 we see the expected 928 bp band, corresponding to the GLP-1 receptor.

RT-PCR of the GLP-1 Receptor. The presence of GLP-1 receptor mRNA was detected in AR42J cells by using RT-PCR. FIG. 23 shows that using primers identical to the known pancreatic GLP-1 receptor sequence (Thorens, 1992), PCR product of predicted size (bp928; see Egan et al., 1994) can be detected in AR42J cells and rat pancreas, but not in PCR of water control. The absence of any genomic DNA contamination is established as our primers span intronic sequences that would yield PCR bands of 1.8 K bases. No additional bands were observed corresponding to contaminating genomic DNA PCR in our PCR reactions. The PCR reactions were cloned, partially sequenced and identified to be the beta cell GLP-1 receptor.

Figure 24:
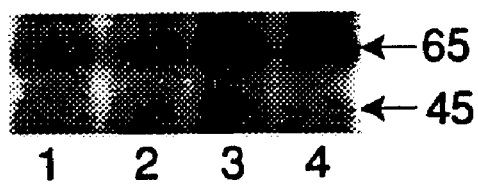
FIG. 24 shows western blot analysis of GLP-1 receptor expression in AR42J (Lane 1,2) and RIN 1046-38 (Lane 3,4) cells. Cells were solubilized and GLP-1 receptors were detected after immunoprecipitation and Western blotting with antibody to the amino-terminus of the GLP-1 receptor. The positions of the molecular markers, in kDa, are on the right. The 65 and 46 kDa bands have been shown to correspond to the mature and core-glycosylated GLP-1 receptors, respectively (28).

Western blot analysis of GLP-1 expression. Using an antibody against the N-terminal region of the GLP-1 receptor, specific bands were obtained at 65 and 45 kDa in the positive control cells, the RIN1046-38 cells, and in the AR42J cells. These have been shown to correspond to the mature and core-glycosylated GLP-1 receptors, respectively (FIG. 24).

Figure 25:
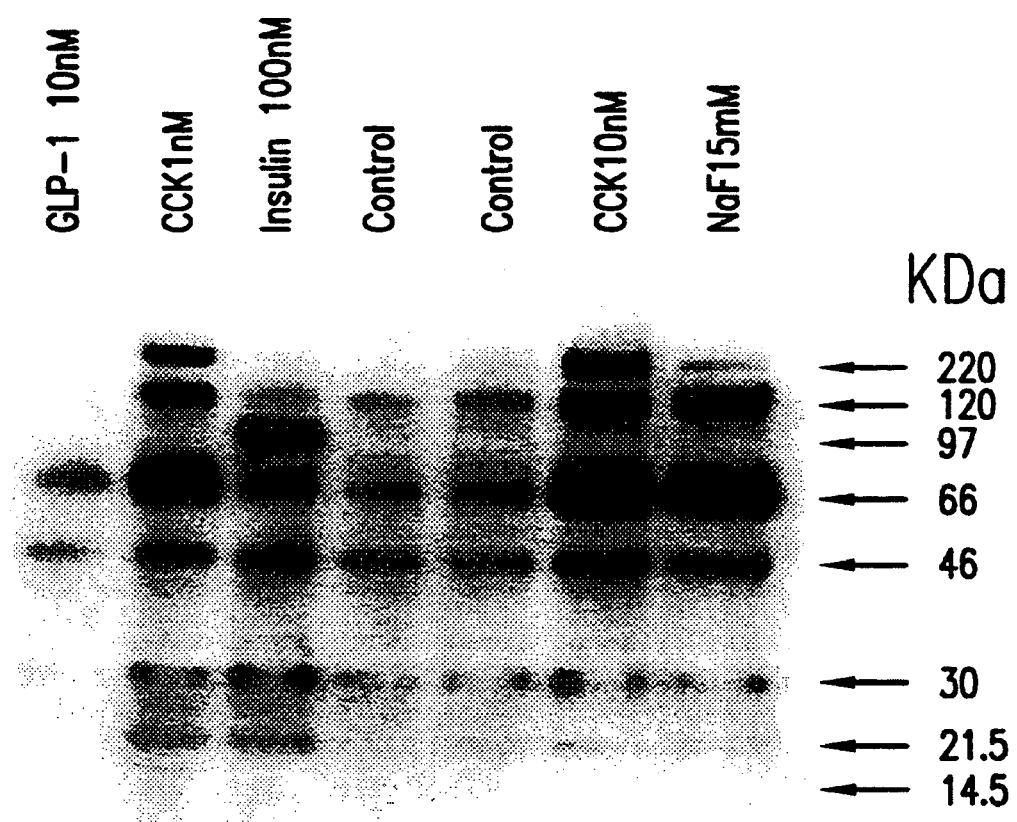
FIG. 25 shows protein tyrosine phosphorylation in AR42J cells in response to various stimuli. A representative anti-phosphotyrosine immunoblot of total cellular proteins from un-treated (control) cells and 5 min-treated cells as indicated (n=3). Note the increase in tyrosine phosphorylation with CCK and sodium fluoride (NaF) of 46, 66, 120 and 190 kDa bands. GLP-1 did not have any effect on those proteins. Insulin caused increased phosphorylation of 97 kDa band, corresponding to the insulin receptor β-subunit.
Figure 26A:
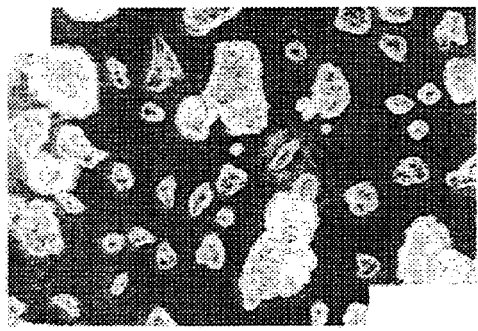
FIG. 26A shows control AR42J cells, anti-insulin antibody.
Figure 26B:
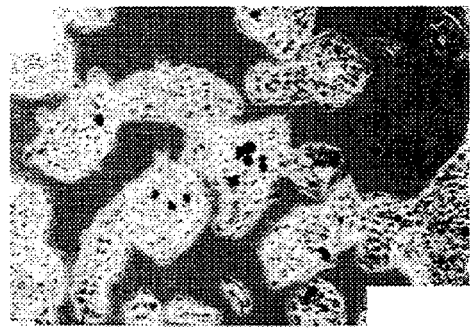
FIG. 26B shows GLP-1 (10 nM)-treated cells for 48 hours, anti-insulin antibody.
Figure 26C:
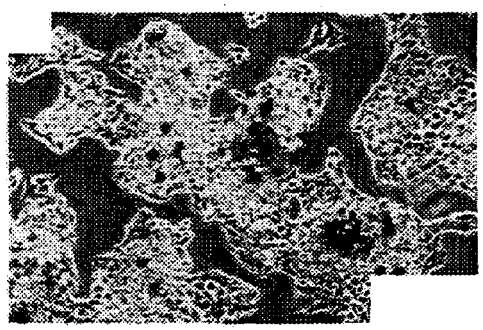
FIG. 26C shows GLP-1 (10 nM)-treated AR42J cells for 72 hours, anti-insulin antibody.
Figure 26D:
FIG. 26D shows RIN 1046-38 insulinoma cells, anti-insulin antibody.
Figure 26E:
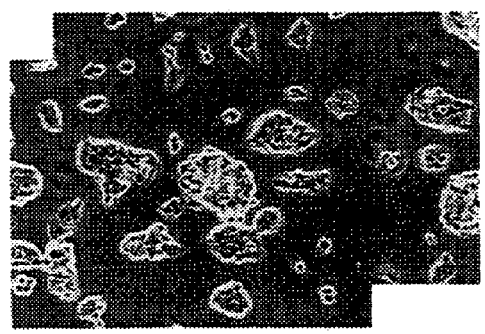
FIG. 26E shows control cells, anti-glucagon antibody.
Figure 26F:
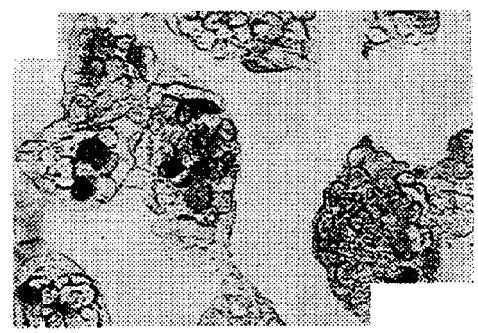
FIG. 26F shows GLP-1 (10 nM)-treated cells for 48 hours, anti-glucagon antibody.

Tyrosine Phosphorylation Studies. In the absence of any stimulation, some proteins exhibited a basal level of phosphorylation which was increased in the presence of CCK and NaF, but not GLP-1 (FIG. 25). Four proteins (46, 66, 120 and 190 kDa) were the most obviously influenced in the presence of CCK with at least a 2-fold increase in the phosphorylation levels of those proteins. Genistein decreased tyrosine phosphorylations induced by CCK and diminished CCK-mediated amylase release, as already shown in FIG. 18.

AR42J cells respond in a physiological manner to CCK as evidenced by induction of amylase release in a concentration-dependent manner and increased intracellular calcium. CCK also induced protein tyrosine phosphorylation as had previously been shown (Lutz et al., 1993). CCK induced substantial increases in tyrosine phosphosubstrates of kDa 190, 120, 66 and 46 on the basis of apparent molecular masses when separated on SDS-polyacrylamide gels. Two of those phosphorylations, 120 and 66 kDa, have already been described (Id.). Inhibition of tyrosine phosphorylation by genistein inhibited amylase release and also decreased tyrosine phosphorylation events. This suggests that in AR42J cells, as in acinar cells, that tyrosine phosphorylation is involved in regulated amylase secretion. Insulin induced phosphorylation of most probably its own receptor beta subunit at 97 kDa. NaF, a well known activator of G proteins (Rivard et al., 1995), has previously been shown to mimic CCK's effects in acinar cells in that it increases amylase release and increases tyrosine kinase activity in acinar cells (Id.). NaF mimics CCK's effects on tyrosine phosphorylation events in AR42J cells and therefore lends credence to the hypothesis that there exists a fluoride-sensitive G protein that functions as a transducer between the CCK receptor and tyrosine phosphorylation (Id.).

GLP-1 clearly increased intracellular calcium but did not appear to increase amylase release alone or with CCK in AR42J cells. No increase in cAMP was demonstrated in the presence of GLP-1 though it was obvious with glucagon. Malhotra et al. (1992), using rat acinar cells, stated that exendin-4, the Gila monster venom that is homologous to GLP-1, potentiated CCK-induced amylase release and increased cellular cAMP but did not discuss GLP-1 effects. However, increased cAMP was not seen until $10^{-8}$ M exendin-4 was used, at which concentration exendin-4 may be interacting through other receptors (Id.). Likewise the effect on potentiating CCK-induced amylase release (from 12% of total amylase released by CCK alone vs. 16% with exendin-4 and CCK together) was seen with $10^{-8}$ M exendin-4 and reached statistical significance only at the 15 min time point (p<0.02) of a time course of exposure to CCK for 1 hour. The methods may not be sensitive enough to pick up such a very small and time-specific effect of GLP-1 or exendin-4 if it were occurring, and, once again, the effect on secretion shown by Malhotra et al. may be due to interaction with other receptors. In beta cells of the pancreas exendin-4 increases cAMP and insulin secretion with concentrations as low as $10^{-10}$ M concentrations (Goke et al., 1993). Alternatively, due to low receptor affinity, small, acute changes in cAMP levels with GLP-1 may not have been detected.

The response of AR42J cells is similar to that seen in peripheral cells (liver, fat, and skeletal muscle), which do not show an increase in cAMP levels either (Valderde And Villanueva-Penacarrillo, 1996). It appears that GLP-1 might be coupled to either a different G-protein subtype than in beta cells or to other G-protein subtypes. The CCK receptor has been shown to be coupled to $G_i$ subtypes as well as $G_q$ subtypes in acinar cells (Schnefel et al., 1990). In AR42J cells, GLP-1 may be coupled to at least a $G_i$ subtype and possibly other G-protein alpha subunits. In 3T3-L1 adipocytes, in which GLP-1 increases lipid synthesis and glucose uptake, it has been shown that the GLP-1 receptor is most likely coupled to a $G_i$ subtype (Montrose-Rafizadeh et al., *J. Biol. Chem.*, 1997) and that in CHO cells which overexpress the GLP-1 receptor it is coupled to other alpha subunits (Montrose-Rafizadeh et al., *Diabetes*, 1997).

Similar to CCK, the rise in intracellular calcium induced by GLP-1 was from the endoplasmic reticulum. However, the pattern of the calcium gradients was not the same as with CCK, implying that the signaling to the release of calcium by CCK was possibly different from that by glucagon and GLP-1. GLP-1 did not increase tyrosine phosphorylation events. This demonstrates once again the importance of tyrosine phosphorylation for regulated amylase release. It also demonstrates that pathways independent of an elevation of intracellular calcium are important for the secretion of amylase. This is further underscored by the results obtained in the presence of thapsigargin and ryanodine. While they prevented any rise in intracellular calcium they reduced, but did not completely prevent, CCK-induced amylase release. So a rise of intracellular calcium is necessary for the full expression of CCK-induced amylase release but of itself it is clearly not sufficient to induce amylase release in AR42J cells.

Any cell type may contain diverse beta subunits of the GTP-binding proteins (von Weizsacker et al., 1992). This could mean that depending on the subtype activated, i.e., $G_q$ by CCK or GLP-1, $G_s$ by glucagon or GLP-1, or $G_i$ by both CCK and GLP-1, a different $G_{\beta\gamma}$ subunit may be released. A specific $G_{\beta\gamma}$ might then be required for the tyrosine phosphorylation events observed in AR42J cells as already described for mitogen-activated protein kinase activation (Hawes et al., 1995). It also raises the possibility that if two different $G_{\beta\gamma}$ subunits are released by the action of one hormone they might have additive or antagonistic effects on various down-stream events.

GLP-1 receptors are present on AR42J cells. Their activation by GLP-1 and exendin-4 leads to increased intracellular calcium, probably from the ER. Their activation, however, does not lead to an increase in amylase release and CCK-induced amylase release is not potentiated.

Example 5

As discussed in Example 4, GLP-1 receptors are present on AR42J cells, and acute treatment of AR42J cells with GLP-1 raises intracellular calcium in the cells. Furthermore, previous studies showed that, although dexamethasone promoted AR42J cells to become acinar-like cells (Christophe, 1994), betacellulin and activin A converted approximately 10% of AR42J cells into insulin-producing cells (Mashima et al., *J. Clin. Invest.* 1996). Similarly, after exposure to hepatocyte growth factor (HGF, also known as heptocyte scatter factor (HSF)), about 3% of AR42J cells were insulin positive; whereas exposure to HGF and activin A resulted in about 10% insulin positive cells (Mashima et al., *Endocrinology*, 1996). There was no mention in either of the above studies relating to either GLP-1 or exendin-4. Furthermore, either GLP-1 or Exendin-4 can convert AR42J cells into insulin-producing cells in far greater numbers than combined treatment with activin A and betacellulin or combined treatment with HGF and activin A. The mechanism of the effect by GLP-1 or exendin-4 may involve, as a final step, activation of the ERK/MAPK pathway, as inhibition of ERK activation prevented the insulin and glucagon production.

Materials. AR42J cells were obtained from ATCC (Rockville, Md.). GLP-1, exendin-4 and exendin 9–39 (the GLP-1 receptor antagonist) were from Bachem (Torrance, Calif.). Anti-insulin and anti-glucagon antibodies were from Linco (Charles, Mo.). Anti-rat ERK1/2 antibody (ERK1-CT) and Myelin Basic Protein (MBP) were purchased from Upstate Biotechnology Incorporated (Lake Placid, N.Y.). Insulin radioimmunoassay reagents were from Peninsula Laboratories (Belmont, Calif.). Protein measurement reagents were obtained from Bio-Rad (Hercules, Calif.). Peroxidase ABC kits were obtained from Vector Laboratories (Burlingame, Calif.). Tian™ One Tube RT-PCR system was purchased from Boehringer Mannheim (Indianapolis. Ind.). Deoxyribonuclease I was obtained from Gibco BRL (Gaithersburg, Md.). Glass coverslips were from VWR Scientific (Baltimore, Md.). The protein kinase C (PKC) inhibitor 1-o-Hexadecyl-2-o-methyl-rac-glycerol (PKI), and the MAP kinase kinase (MAPKK) inhibitor, PD98059, were from Calbiochem (San Diego, Calif.).

Cell culture. AR42J cells were maintained in Dulbecco's modified Eagle's medium (DMEM) supplemented with 10% fetal calf serum (FBS), 100 IU/ml penicillin, 100 µg/ml streptomycin and 2 mM glutamine. Cells from passage 23–35 were used throughout this study. Cells were routinely plated at a density of about $10^5$ cells/ml in 12-well cluster dishes or on coverslips and incubated in a humidified incubator at 37° C. with 95% air and 5% $CO_2$.

Immunocytochemistry analysis. Cells were cultured on glass coverslips, washed with phosphate buffered saline (PBS) to remove serum, and fixed with 0.5% glutaraldehyde in PBS. Cells were permeabilized with 0.2% Triton X-100 for 5 min and the rest of the procedure was carried out at room temperature in a humidified chamber. Suction was used to remove reagents between each step but drying of specimens was avoided. Sufficient reagent was used to cover each specimen (approximately 1 or 2 drops was usually adequate). The coverslips were incubated in 0.3% $H_2O_2$ in PBS for 30 min to quench endogenous peroxidase activity and washed in PBS×3 times, followed by incubation with 2% goat serum in PBS for 30 min to block non-specific binding of IgG. Excess serum was removed by blotting. The specific primary polyclonal antisera (anti-insulin 1:300; anti-glucagon 1:300) were used. Antibody was diluted in PBS containing 1% goat serum. This was applied to the coverslip and incubated at room temperature for 1 h. The coverslips were washed ×3 times in PBS, each time for 5 min, then incubated with biotinylated second antibody for 1 h and washed ×3 times with PBS. Avidin-biotin-peroxidase complex in PBS was applied for 30 min. Immunoperoxidase labeling was performed with a Vectostain ABC kit (Vector Labs, Burlingame, Calif.). After extensive washing in PBS for 4–5 times (each 5 min), the coverslips were incubated in diaminobenzidine tetrahydrochloride (DAB) in PBS, with 0.01% hydrogen peroxide for 3 min. The reaction was stopped by washing the coverslips in PBS and examined under a light microscope. To confirm specific staining, samples incubated with preabsorbed primary antibody were used as negative control, and the insulin producing cell line RIN 1046-38 cells were used as positive control for our experiments. The avidin-biotin-peroxidase (ABC) procedure was performed according to methods known in the art (Hsu et al., 1981).

Measurement of immunoreactive insulin. AR42J cells were cultured as before in 12-well cluster plates. When cells reached 60% confluence, they were treated with GLP-1 for 3 days. At the beginning of the experiments, an aliquot of the medium was taken in order to assay the insulin accumulation in the medium. Then the cells were twice washed with Kreb's Ringer Balanced Buffer (KRBB) and incubated in the same buffer containing 10 mM glucose for another 1 h. The medium was collected and kept at −20° C. until insulin levels were assayed by RIA (See Example 1; Wang et al., *Endocrinology,* 1995). The cells were washed with PBS and detached with 0.25% typsin and 0.02% EDTA. The cell pellet was collected and lysed with formic acid for protein determination by the Bradford method (Bradford, 1976), using bovine-globulin as standard.

Reverse-transcription polymerase chain reaction (RT-PCR). Total RNA was isolated from treated AR42J cells by the methods of Chomczynski and Sacchi (1987). The total RNA samples were pretreated with DNAse in 20 mM Tris-HCL (pH 8.4), 2 mM $MgCl_2$ and 50 mM KCl to remove any traces of contaminating genomic DNA. RT-PCR was undertaken in a volume of 50 µl of buffer containing 50 mM KCl, 10 mM Tris-HCl, 3.5 mM $MgCl_2$, 200 µM each dNTPs, 0.4 µM each of sense and antisense primers to rat insulin I and II (insulin sense primer=5'TGCCCAGGCTTTTGTCAAACAGCACCTT3'; insulin antisense primer=5'CTCCAGTGCCAAGGTCTGAA 3'). Amplification was undertaken for 25 cycles at denaturing temperature 94° C. for 1 min, annealing temperature 60° C. for 45 sec and an extension temperature 72° C. for 1 min. mRNA from RIN 1046-38 cells were used as a positive control. In the case of glucagon RT-PCR, the denaturing and extension temperature was similar to insulin except the annealing temperature was 65° C. for 1 min (glucagon sense primer=5' GTGGCTGGATTGTTTGTAATGCTGCTG3'; antisense primer=5' CGGTTCCTCTTGGTGTTCATCAAC3'). The RT-PCR products were visualized by ethidium bromide staining on 2% agarose gels.

MAP Kinase Activity. After treatment, 60 mm dishes of 80% confluent cells were lysed at 4° C. in lysis buffer (in mM): 50 TRIS-HCl, PH 8, 150 NaCl, 5 EDTA, 1% NP-40, 0.25% sodium deoxycholate, 1 NaF, 10 sodium pyrophosphate, 0.1 PMSF, 1 sodium orthovanadate, 20 µg/ml aprotinin, and 10 µg/ml leupeptin. The cell lysate was clarified by centrifugation at 16,000×g at 4° C. for 20 min. The clarified cell lysate was immunoprecipitated overnight at 4° C., rotating with 4.5 µg of ERK1-CT antibody and 40 µl of packed protein G+protein A agarose resin (Oncogene Research Product, Cambridge, Mass.). The immune pellet was assayed for MAPK activity using MBP as the substrate. MBP (18.6 µg) was phosphorylated at 20° C. for 10 min in a final volume of 60 µl containing 20 mM Hepes, PH 7.4, 10 mM $MgCl_2$, 1 mM DTT, 20 uM unlabeled ATP and 40 µCi (3,000 Ci/mmol) [$^{32}P$]-ATP. The reaction was terminated by the addition of 25 µl of 3× Laemmli sample buffer and heating at 70° C. for 10 min. MAPK activity was assessed by SDS-PAGE and auto-radiography. The autoradiograms were quantified by densitometry.

Amylase Assay. For amylase determination, cells were washed free of medium with 2 ml PBS. Incubation was then carried out in DMEM containing 15 mM HEPES, 0.2% BSA and 0.01% soybean trypsin inhibitor. CCK (1 nM) was added for 50 min at 37° C. The incubation medium was then immediately removed for amylase determination and the cells were again washed in 2 ml ice-cold PBS. Lysate buffer containing (in mM) 130 Tris-HCl, 10 $CaCl_2$, 75 NaCl, and 0.2% Triton X-100 (pH 8.0) was added to the cells and the lysates were then collected for total amylase (Ceska et al., 1969). The released amylase was expressed as the percentage of the total amylase in the cells.

Statistics. All data values are shown as mean±SEM, and the differences among the treated groups were analyzed by one factor ANOVA analysis. Differences between treated and non-treated cells were analyzed using the Students' t test. p<0.05 was considered significant difference.

Effects of GLP-1 on the expression of insulin and glucagon. After GLP-1 or exendin-4 treatment, AR42J cells convert to insulin-containing cells. Using anti-insulin antibody, intense immunostaining was present in AR42J cells. In contrast, no immunostaining was observed in AR42J cells not treated with GLP-1. Preabsorption of the antibodies with an excess of insulin and glucagon prevented staining (FIG. 26).

Figure 27:
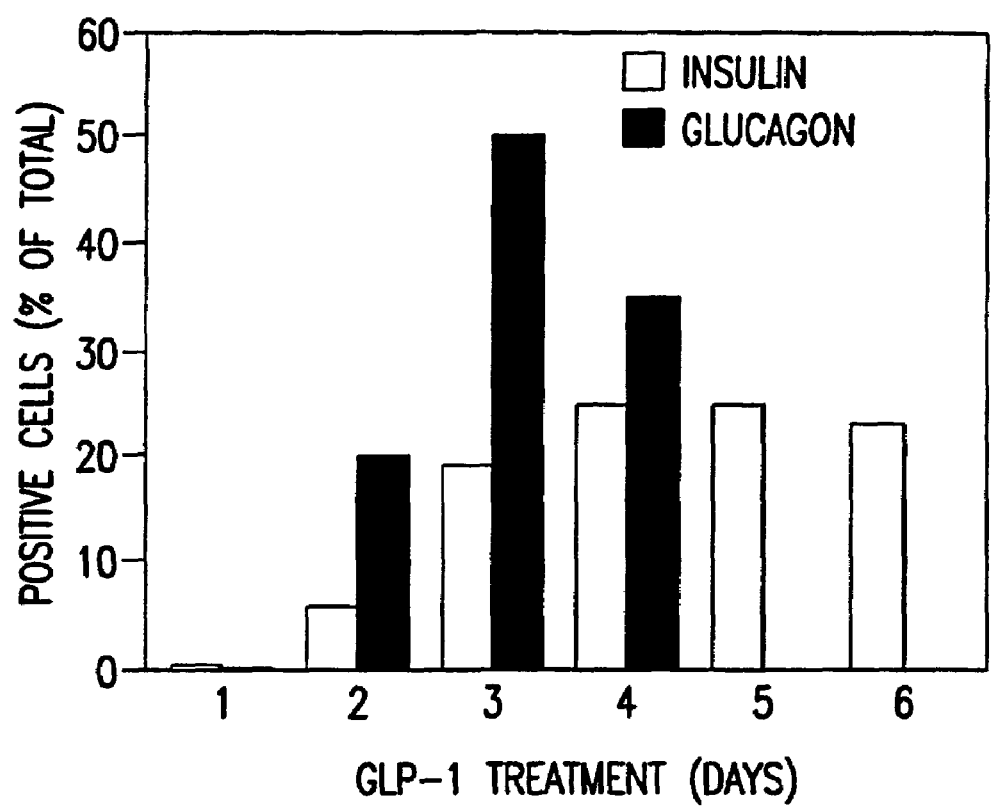
FIG. 27 shows the effect of time on the induction of glucagon and insulin by GLP-1 (10 nM) production in AR42Jcells. For this experiment, cells were plated on the coverslips as described herein, all on the same day. They were then stained with anti-insulin or anti-glucagon antibody on the days indicated. This has now been repeated numerous times (at least 5 times) on different days and insulin and glucagon have always been present.

With 1 nM GLP-1, ~10% converted into insulin-positive cells after 3 days. When 10 nM GLP-1 or 0.1 nM exendin-4 were used for 3 days, ~25% of the AR42J cells converted into insulin-positive cells. In some areas of the slides whole sheets of contiguous cells became positive for insulin. An occasional glucagon-positive cell appeared as early as 24 h. By 48 h, 20% of all treated AR42J cells were glucagon positive, with ~6% of the cells being insulin-positive. By 72 h fully half of all the treated cells contained glucagon. The number of cells contained glucagon declined thereafter but still ~25% of cells remained insulin-positive for at least 7 days (FIG. 27). The presence or absence of dexamethasone in the culture medium did not in any way influence the number of cells that converted to "endocrine" cells in the presence of GLP-1. When PD98059 (50 µM), a selective inhibitor of MEK which phosphorylates and activates ERK, or PKI (300 µM) were added concurrently with GLP-1, conversion of the cells did not occur.

Insulin release. After a 3 day period of treating AR42J cells with 1 nM GLP-1, insulin was readily detected in the culture medium by radioimmunoassay. Over 3 separate cultures 5.1±0.4 pg insulin/µg protein (mean±SD) was present in the cell culture medium from the 60–72 h time period. To investigate whether glucose could induce insulin secretion from 3 day-GLP-1-treated and non-treated cells, the medium was removed and the cells washed with glucose-free KRBB×3 times. This was followed by the addition of KRBB containing 10 mM glucose for 1 h and the cells maintained at 37° C. The incubating buffer was collected and insulin measured. Insulin was zero from the control cells, whereas there was 0.65±0.15 pg insulin/µg protein present in the buffer of cells that had previously seen 3 days of GLP-1. Insulin secretion was barely detected in the presence of 200 µM PKI or in the presence of PD98059 (50 µM).

Figure 28:
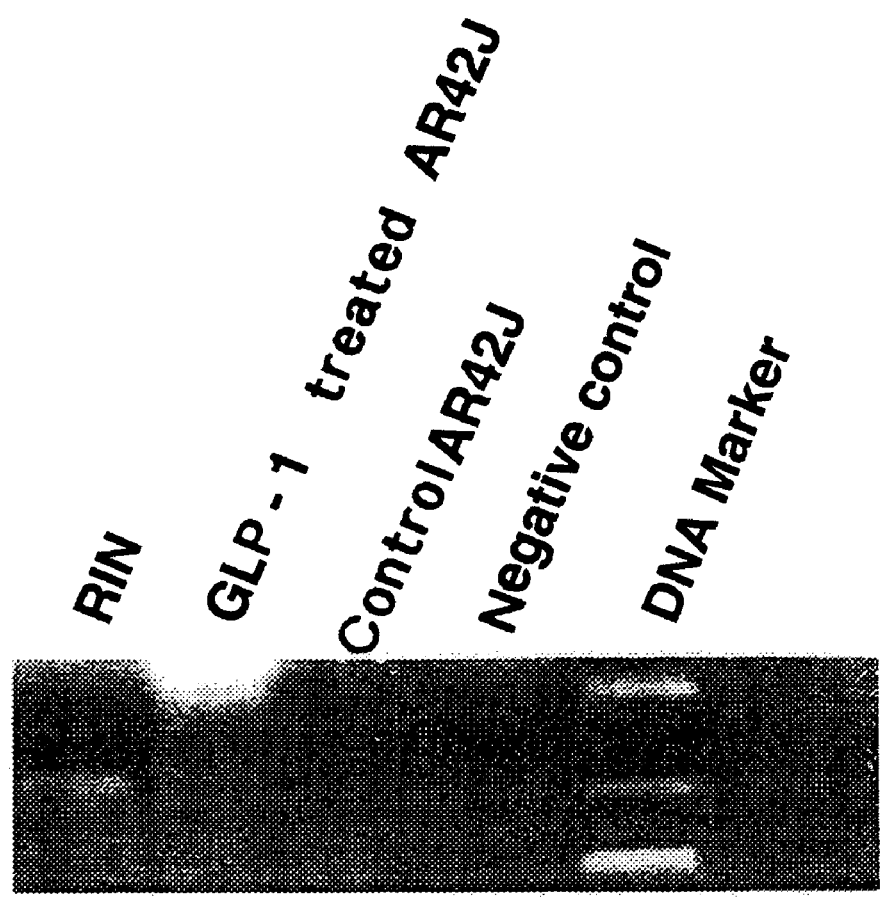
FIG. 28 shows expression of mRNAs for insulin and glucagon using RT-PCR.

RT-PCR analysis. RT-PCR analysis demonstrated a 187 bp rat insulin I and II mRNA in GLP-1-treated AR42J cells for 3 days. The RIN cells were used as positive control. In this experiment, RNA was pretreated with DNAse, only a mRNA fragment of insulin I and II with the predicted length was amplified, thus the band that appeared at 187 bp was the specific insulin mRNA product (FIG. 28A). In contrast, no RT-PCR products were detected in the negative control or in non-GLP-1-treated cells. Northern blot analysis of GLP-1-stimulated AR42J cells was faintly positive and therefore the band scanned poorly. Glucagon mRNA at 236 bp was detected in GLP-1-treated AR42J cells at 48 h (FIG. 28B).

Figure 29:
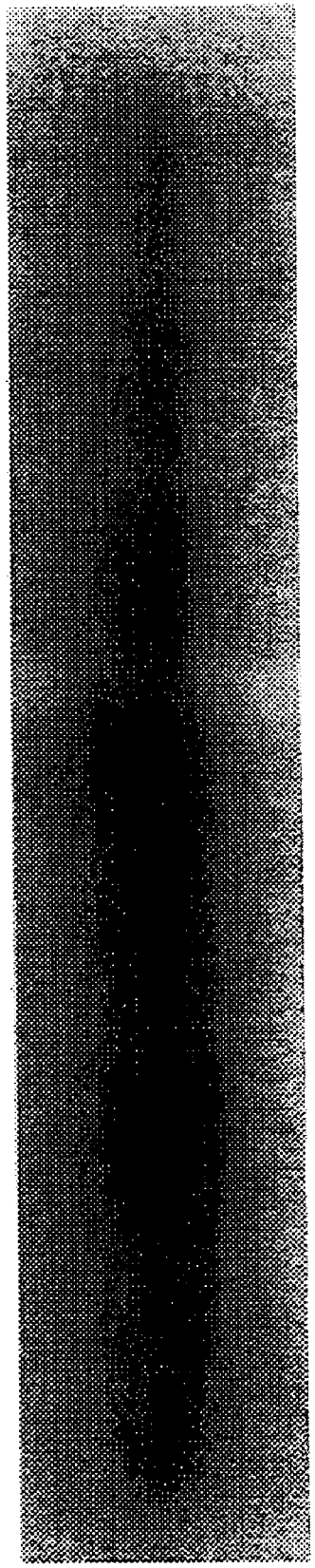
FIG. 29 shows the effect of GLP-1 and exendin-4 in the presence or absence of a protein kinase C inhibitor in AR42J cells from one representative experiment, which was repeated 3 times.

MAP kinase activity. ERK activation was readily detected in AR42J cells. Its activity was markedly increased with GLP-1 and exendin-4, the Gila monster venom peptide, that is 52% homologous to GLP-1 and been shown to be an insulin secretagogue (Goke et al., 1993). Exendin-4 was about 100-fold more potent than GLP-1 (FIGS. 29A and 29B). PKI (300 μM) alone decreased MAPK activity to less than that of control cells.

Figure 30:
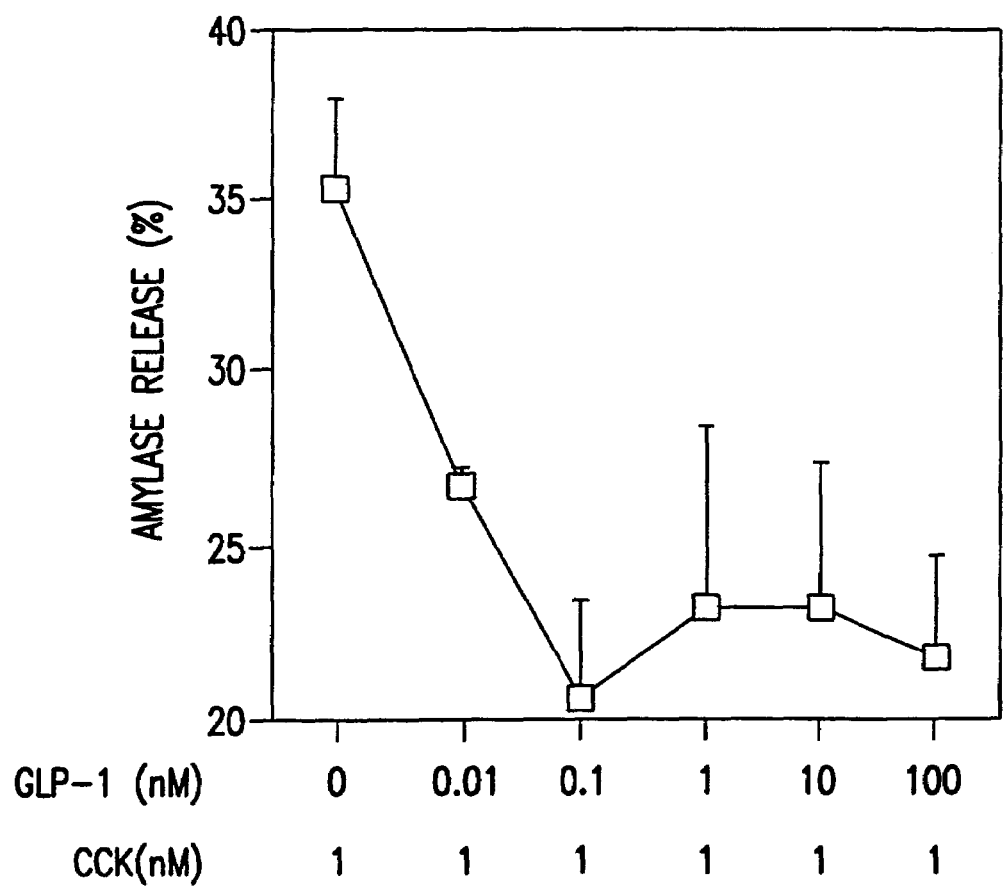
FIG. 30 shows the dose-response effect of GLP-1 on amylase release from dexamethasone-treated AR42J cell. After 3 days treatment with different concentration of GLP-1 the AR42J cells were washed and 1 nM CCK was added. The cells were incubated for another 50 min and the samples were collected for amylase assay. N=4, Mean±SEM.

Amylase change. Incubating AR42J with dexamethasone for 72 h increased amylase content 6.6-fold (12.57 U/l) in the cells compared with non-dexamethasone-treated cells (1.88 U/l). When GLP-1 was added together with dexamethasone, the total amylase content was decreased compared to dexamethasone treatment alone (7.76 U/1). The acute response to CCK (1 nM) was also decreased in the cells that were pretreated with GLP-1 for 72 h (FIG. 30).

GLP-1 induces AR42J cells to differentiate into pancreatic endocrine cells, or, at the very least, into cells with endocrine traits. In conjunction with this observation, the same pattern occurs in the developing embryonal pancreas (Guz et al., 1995). Glucagon is the first hormone detected (Rall et al., 1973). It is postulated that cells containing glucagon are precursor cells for various other types of islet endocrine cells, and that they, in turn, arose from ductal epithelium (Guz et al., 1995). But the mechanisms regulating formation and differentiation of the pancreatic hormone-producing cells is still largely undetermined. GLP-1 turns on glucagon production very early in AR42J cells and this is then closely followed by insulin production. Eventually the majority of the "endocrine" AR42J cells are insulin-producing cells as the glucagon production wanes. Exendin-4 was even more potent than GLP-1 as a factor for insulin production in AR42J cells. Some insulin-containing cells were seen in the presence of concentrations as low as $10^{-11}$ molar exendin-4. GLP-1 (and/or a GLP-1-like peptide, perhaps resembling exendin-4) may be a differentiation factor in the embryo for islets. Such a peptide would be expected to be present in high concentrations locally as the pancreas is forming from the primitive gut.

Glucagon has been hypothesized to be the signal for differentiation of the beta cells by increasing cAMP which would lead to a decrease in cell proliferation and to changes in macromolecular synthesis, culminating in the beta cell phenotype. (Rall et al., 1973) This might still be applicable in the AR42J cells. As glucagon is the hormone seen first in our system it could be the signal for insulin production. GLP-1 produced in the primitive gut might be the signal for the glucagon expression (and subsequently the insulin expression), which would lead to the further formation of endocrine cells and islet-like structures.

The final common pathway to "endocrine" cell differentiation in AR42J cells, as well as other cell types, is likely through the ERK/MAPK pathway. GLP-1 or Exendin-4 produce little or no insulin staining in AR42J cells and no insulin into the medium when the ERK activity is inhibited. Little or no insulin in the presence of GLP-1 and a PKC inhibitor is observed. As the GLP-1 receptor is known to be G-protein linked, is present on AR42J cells, and raises intracellular calcium in AR42J cells (see Example 4), its activation by ligand binding probably leads to PKC activation as well as other as yet undetermined down-stream events (Nishizuka, 1984; Zamponi et al., 1997). PKC, in turn, has been shown to be one of the factors that activates the MAPK pathway (Offermanns et al., 1993; Siddhanti et al., 1995). Therefore, blocking PKC activation by GLP-1 probably lead to diminishing MAPK activity and prevented the development of the "endocrine" cell phenotype.

Moreover, not all cells convert to "endocrine" cells with GLP-1, even with incubations as long as 7 days. The treated AR42J cells possess both exocrine and neuroendocrine properties, as has been described for untreated AR42J cells (see Christophe, 1994). Morphologically, various populations of the treated cells do not appear the same. Thus, sub-populations of cells may be present in the untreated AR42J cells. Specifically, some of these populations may possess the GLP-1 receptor, and others may not. Cell preparations made from the total population of AR42J cells possess GLP-1 receptors by Western blotting, PCR analysis and partial sequencing. On sequencing, the receptor is identical to that found on beta cells and which has been fully characterized already (see Example 4). Furthermore, at least 50% of the AR42J cells increase intracellular calcium in response to GLP-1. Therefore, GLP-1 probably activates a series of events which require increased intracellular calcium and as yet other hitherto unknown factors which are definitely present in AR42J cells and commit them to become "endocrine" cells.

Example 6

Subjects diagnosed with Type 1 diabetes can be selected for treatment with GLP-1 or exendin-4. The treatment method of Gutniak et al., 1992 can be modified so that GLP-1 is administered for at least twenty four hours by cannula in the antecubital vein. The cannula can be connected to an insulin infusion system pumping between 0.03 and 4.80 nmoles/kg/min GLP-1. Blood glucose levels can be monitored regularly, using methods well known in the art, during administration of GLP-1 and following the twenty-four hour period of GLP-1 administration. After twenty four hours of GLP-1 infusion, the subject shows levels of blood glucose that approach normal levels and has a reduced need for insulin therapy.

Alternatively, subjects with Type 1 diabetes can be treated with exendin-4 by a single subcutaneous injection or by daily repeated subcutaneous injections of 0.01 nmole/kg to 0.4 nmole/kg. Blood glucose levels can be monitored regularly after administration of exendin-4. The need for insulin replacement therapy should decrease and blood glucose levels should approach normal levels.

The preceding examples are intended to illustrate, but not limit, the invention. While they are typical of those that might be used, other procedures known to those skilled in the art may be alternatively employed.

By contacting cells with GLP-1 or Exendin-4 as described above, it is understood that both GLP-1 or Exendin-4, substantially homologous sequences, or fragments thereof could be used together.

Throughout this application various publications are referenced. The disclosures of these publications in their entirety are hereby incorporated by reference into this application in order to more fully describe the state of the art to which this invention pertains.

REFERENCES

1. Arver et al. 1991. Different aetiologies of type 2 (non-insulin-dependent) diabetes mellitus in obese and non-obese subjects. *Diabetologia.* 34: 483–487.
2. Bradford. 1976. A rapid and sensitive method for the quantitation of microgram quantities of protein utilizing the principle of protein-dye binding. *Annal. Biochem.* 72: 248–254.
3. Bressler, R. and Johnson, G. G. 1997. Pharmacological regulation of blood glucose levels in non-insulin dependent diabetes. *Arch. Int. Med.* 157:836–848.
4. Busik et al. 1997. Glucose-Specific Regulation of Aldose Reductase in Capan-1 Human Pancreatic Dcust Cells In Vitro. *J. Clin. Invest.* 100: 1685–1692.

5. Ceska et al. 1969. A new and rapid method for the clinical determination of alpha-amylase activities in human serum and urine. *Clin. Chim. Acta* 26: 437–444.

6. Chen and Drucker. 1997. Tissue-specific expression of unique mRNAs that encode pro-glucagon-derived peptides or exendin-4 in the lizard. *J. Biol. Chem.* 272: 4108–4115.

7. Chigwin et al. 1979. Isolation of biologically active ribonucleic acid from sources enriched in ridonuclease. Biochemistry. 18: 5294–5299.

8. Chomczynski and Sacchi. 1987. Single-step method of RNA isolation by acid guanidinium thiocyanate-phenol-chloroform extraction. *Analyt. Biochem.* 162: 156–159.

9. Christophe. 1994. Pancreatic tumoral cell line AR42J: an amphicrine model. Am. J. Physiol. 266: G963–971.

10. De Ore et al. 1997. The effects of GLP-1 on insulin release in young and old rats in the fasting state and during an intravenous glucose tolerance test. *J. Geront.* 52: B245–249.

11. Drucker et al. 1987. Glucagon-like Peptide 1 stimulates insulin gene expression and increases cyclic AMP in a rat islet cell line Proc. Natl. Acad. Sci. USA. 84: 3434–3438.

12. Egan et al. 1994. Glucagon-like peptide-1 (7–36) amide (GLP-1) enhances insulin-stimulated glucose metabolism in 3T3-L1 adipocytes: one of several potential extrapancreatic sites of GLP-1 action. *Endocrinology* 135: 2070–2075.

13. Egan et al. 1991. Glucose stimulated insulin release by individual beta cells: potentiation by glyburide. J. Exp. Med. Biol. 196: 203–210.

14. Elahi, et al. 1994. The insulinotropic actions of glucose-dependent insulinotropic polypeptide (GIP) and glucagon-like peptide-1 (737) in normal and diabetic subjects. *Regulatory Peptides.* 51: 63–74.

15. Elahi, et al. 1985. The effect of age and glucose concentration on insulin secretion by the isolated perfused pancreas. *Endocrinology* 116: 11–16.

16. Fehmann and Habener. 1992. Insulinotropic hormone glucagon-like peptide-1 (7–37) stimulation of proinsulin gene expression and proinsulin biosynthesis in insulinoma βTC-1 cells. *Endocrinology* 130: 159–166.

17. Fehmann et al. 1995. Cell and Molecular Biology of the Incretin Hormones Glucagon-Like Peptide-I and Glucose-Dependent Insulin Releasing Polypeptide. *Endocrine Rev.* 16:390–410.

18. Ghazzi et al. 1997. Cardiac and glycemic benefits of troglitazone treatment in NIDDM. *Diabetes.* 46: 433–439. Care. 15: 270–276.

19. Glisin et al. 1974. Ribonucleic acid isolated by cesium chloride centrifugation. Biochemistry. 13: 2633–2637.

20. Goke et al. 1993. Exendin-4 is a potent agonist and truncated exendin-(9–39)-amide an antagonist at the GLP-1-(7–36)-amide receptor of insulin-secreting β-cells. *J. Biol. Chem.* 268; 19650–19655.

21. Goldfine et al. 1997. The Endocrine Secretion of Human Insulin and Growth Hormone by Exocrine Glands of the Gastrointestinal Tract. *Nature Biotechnology* 15:1378–1382.

22. Gromada et al. 1998. Glucagon-Like Peptide 1(7–36) Amide Stimulates Exocytosis in Human Pancreatic β-Cells by Both Proximal and Distal Regulatory Steps in Stimulus-Secretion Coupling. *Diabetes* 47:57–65.

23. Gutniak et al. 1992. Antidiabetogenic effect of glucagon-like peptide-1 (7–36) amide in normal subjects and patients with diabetes mellitus. *N.Engl. J. Med.* 326: 1316–1322.

24. Guz et al. 1995. Expression of murine STF-1, a putative insulin gene transcription factor, in β cells of pancreas, duodenal epithelium and pancreatic exocrine and endocrine progenitors during ontogeny. Development 121: 11–18.

25. Hawes et al. 1995. Distinct pathways of $G_i$-and $G_q$-mediated mitogen-activated protein kinase activation. *J. Biol. Chem.* 270: 17148–17153.

26. Holz et al. 1995. Activation of a cAMP-regulated $Ca^{2+}$-signaling pathway in pancreatic beta-cells by the insulinotropic hormone glucagon-like-peptide-1. *J. Biol. Chem.* 270: 17749–17757.

27. Hosokawa et al. 1996. Mechanism of impaired glucose-potentiated insulin secretion in diabetic 90% pancreatectomy rats. Study using glucagonlike peptide-1 (7–37). J. Clin. Invest. 97: 180–186.

28. Hsu et al. 1981. Use of avidin-biotin-peroxidase complex (ABC) in immunoperoxidase techniques: A comparison between (ABC) and unlabeled antibody (PAP) procedures. *J. Histochem. Cytochem.* 29: 577–580.

29. Janczewski and Lakatta. 1993. Buffering of calcium influx by sarcoplasmic reticulum during the action potential in guinea-pig ventricular myocytes. *J. Physiol.* 471: 343–363.

30. Kimura et al. 1996. High concentrations of cholecystokinin octapeptide suppress protein kinase C activity in guinea pig pancreatic acini, *Peptides* 17: 917–925.

31. Konnerth et al. 1986. Nonsynaptic epileptogenesis in the mammalian hippocarnpus in vitro. I. Development of seizurelike activity in low extracellular calcium. *J. Neurophysiol.* 56: 409–423.

32. Logsdon et al. 1987. Mechanism of glucocorticoid-induced increase in pancreatic amylase gene transcription. *J. Biol. Chem.* 262: 15765–15769.

33. Lutz et al. 1993. A role for cholecystokinin-stimulated protein tyrosine phosphorylation in regulated secretion by the pancreatic acinar cell. *J. Biol. Chem.* 268: 11119–11124.

34. Malhotra et al. 1992. Exendin-4, a new peptide from heloderma suspectum venom, potentiates cholecystokinin-induced amylase release from rat pancreatic acini. *Regul. Pept.* 41: 149–156.

35. Mashima et al. 1996. Betacellulin and activin A coordinately convert amylase-secreting AR42J cells into insulin-secreting cells. *J. Clin. Invest.* 97:1647–1654.

36. Mashima et al. 1996, Formation of Insulin-Producing Cells from Pancreatic Acinar AR42J Cells by Hepatocyte Growth Factor. *Endocrinology* 137: 3969–3976.

37. Matschinsky. 1990. Glucokinase as glucose sensor and metabolic signal generator in pancreatic β-cells. Diabetes. 39: 647–652.

38. Montrose-Rafizadeh et al. 1997. High potency antagonists of the pancreatic glucagon-like peptide-1 receptor. *J. Biol. Chem.* 272: 21201–21206.

39. Montrose-Rafizadeh et al. 1994. Incretin hormones regulate glucose-dependent insulin secretion in RIN 1046-38 cells: mechanism of action. Endocrinology. 135: 589–594.

40. Montrose-Rafizadeh et al. 1997. Evidence of direct coupling of pancreatic GLP-1 receptor to different G-protein alpha subunits. *Diabetes* 46: 0724a (Abstr.)

41. Montrose-Rafizadeh et al. 1997. Novel signal transduction and peptide specificity of glucagon-like peptide receptor in 3T3-L1 adipocytes. *J. Cell. Physiol.* 172: 275–280.

42. Muallem et al. 1988. Agonist-sensitive calcium pool in the pancreatic acinar cell. I. Permeability properties. *Am. J. Physiol.* 255: G221–228.

43. Mueckler. 1990. Family of glucose-transporter genes. Implications for glucose homeostasis and diabetes. *Diabetes.* 39: 6–11.

44. Nathan et al. 1992. Insulinotropic action of glucagonlike peptide-1-(7–37) in diabetic and nondiabetic subjects. *Diabetes Care.* 15: 270–276.

45. Nauck et al. 1993. preserved incretin activity of Glucagon-like peptide 1 (7–36) amide but not of synthetic human gastric inhibitory polypeptide in patients with Type-2 diabetes mellitus. *J. Clin. Invest.* 91: 301–307.

46. Nauck et al. 1993. normalization of fasting hyperglycemia by exogenous glucagon-like peptide 1 (7–36) amide in Type 2 (non-insulin-dependent) diabetic patients. *Diabetologia.* 36: 741–744.

47. Nishizuka. 1984. The role of protein kinase C in cell surface signal transduction and tumor promotion. *Nature* 308: 693–698.

48. Ochs et al. 1983. Intracellular free calcium concentrations in isolated pancreatic acini: effects of secretagogues. *Biochem. Biophys. Res. Commun.* 117: 122–128.

49. Offermanns et al. 1993. Stimulation of tyrosine phosphorylation and mitogen-activated-protein (MAP) kinase activity in human SH-SY5Y neuroblastoma cells by carbachol. *Biochem. J.* 294: 545–550.

50. Orskov. 1992. Glucagon-like peptide-1, a new hormone of the entero-insular axis. *Diabetologia.* 35: 701–711.

51. Perfetti et al. 1995. Age-dependent reduction in insulin secretion and insulin mRNA in isolated islets from rats. *Am. J. Physiol.* 269: E983–990.

52. *Physician's Guide to Insulin Dependent [Type 1] Diabetes Mellitus: Diagnosis and Treatment.* American Diabetes Association, 1988.

53. Rall et al. 1973. Early differentiation of glucagon-producing cells in embryonic pancreas; a possible developmental role for glucagon. *Proc. Nat. Acad. Sci. USA* 70: 3478–3482.

54. Ritzel et al. 1995. Pharmacokinetic, insulinotropic, and glucagonostatic properties of GLP-1 [7–36 amide] after subcutaneous injection in healthy volunteers. Dose-response-relationships. *Diabetologia.* 38: 720–725.

55. Rivard et al. 1995. Novel model of integration of signaling pathways in rat pancreatic acinar cells. *Am. J. Physiol.* 269: G352–G362.

56. Saiki et al. 1988. Primer-directed enzymatic amplification of DNA with a thermostable DNA polymerase. *Science* 239: 487–491.

57. Schaffert et al. 1997. Modification of Blood Group A Expression in Human Pancreatic Tumor Cell Lines by Inhibitors of N-Glycan Processing. *Internat'l J. Pancreatology* 21: 21–29.

58. Schnefel et al. 1990. Cholecystokinin activates $G_i1$-, $G_i2$-, $G_i3$-and several $G_s$-proteins in rat pancreatic acinar cells. *Biochem. J.* 269: 483–488.

59. Siddhanti et al. 1995. Forskolin inhibits protein kinase C-induced mitogen-activated protein kinase activity in MC3T3-E1 osteoblasts. *Endocrinology.* 136: 4834–4841.

60. Spurgeon et al. 1990. Simultaneous measurement of $Ca^{2+}$, contraction, and potential in cardiac myocytes. *Am. J. Physiol.* 258: H574–H586.

61. Steiner et al. 1972. Radioimmunoassay for cyclic nucleotides II adenosine 3',5'-monophosphate and guanosine 3',5'-monophosphate in mammalian tissues and body fluids. *J. Biol. Chem.* 247: 1114–1120.

62. Teitelman. Induction of beta-cell neogenesis by islet injury. *Diabetes Metabolism Rev.* 12: 91–102, 1996.

63. Thorens. 1992. Expression cloning of the pancreatic beta cell receptor for the gluco-incretin hormone glucagon-like peptide 1. *Proc. Natl. Acad. Sci. USA* 89: 8641–8645.

64. Thorens et al. 1993. Cloning and functional expression of the GLP-1 receptor: Demonstration that exendin-4 is an agonist and exendin-3(9–39) is an antagonist of the receptor. *Diabetes.* 42: 1678–1672.

65. Thorens and Waeber. 1993. Glucagon-like peptide-1 and the control of insulin secretion in the normal state and in NIDDM. *Diabetes.* 42: 1219–1225.

66. UK Prospective Study Group. 1995. UK Prospective Diabetes Study 16: Overview of 6 years' therapy of Type 2 diabetes: A progressive disease. *Diabetes.* 44: 1249–1258.

67. Vajanaphanich et al. 1995. Cross-talk between calcium and cAMP-dependent intracellular signaling pathways. *J. Clin. Invest.* 96: 386–393.

68. Valverde and Villanueva-Penacarrillo. 1996. In vitro insulinomimetic effects of GLP-1 in liver, muscle and fat. *Acta Physiologica Scandinavica* 157: 359–360.

69. von Weizsacker et al. 1992. Diversity among the beta subunits of heterotrimeric GTP-binding proteins; Characterization of a novel beta-subunit cDNA. *Biochem. Biophys. Res. Commun.* 183: 350–356.

70. Wang et al. 1997. Glucagon-like peptides-1 can reverse the age related decline in glucose tolerance in rats. *J. Clin. Invest.* 99: 2883–2889.

71. Wang et al. 1995. Glucagon-like peptide-1 affects gene transcription and messenger ribonucleic acid stability of components of the insulin secretory system in RIN 1046-38 cells. *Endocrinology.* 136: 4910–4917.

72. Wang et al. 1996. GIP regulates glucose transporters, hexokinases, and glucose-induced insulin secretion in RIN 1046-38 cells. *Moll. Cell. Endo.* 116: 81–87.

73. Wang et al. 1995. Glucagon-like peptide-1 is a physiological incretin in rat. *J. Clin. Invest.* 95: 417–421.

74. Wang et al. 1988. Effects of aging on insulin synthesis and secretion. Differential effects on proinsulin messenger mRNA levels, proinsulin biosynthesis, and secretion of newly made and preformed insulin in the rat. *J. Clin. Invest.* 81: 176–184.

75. Wang and Rowe. 1988. Age-related impairment in the short term regulation of insulin biosynthesis by glucose in rat pancreatic islets. *Endocrinology* 123: 1008–1013.

76. Widmann et al. 1996. Desensitization and phosphorylation of the glucagon-like peptide-1 (GLP-1) receptor by GLP-1 and 4-phorbol 12-Myristate 13-acetate. *Mol. Endocrinol.* 10: 62–75.

77. Wills et al. 1996. Gastric emptying, glucose responses, and insulin secretion after a liquid test meal: effects of exogenous glucagon-like peptide-1-(7–36) amide in Type 2 (non-insulin-dependent) diabetic patients, *J. Clin. Endocrinol. Metab.* 81: 327–332.

78. Yada et al. Glucagon-like peptide-1-(7–36) amide and a rise in cyclic adenosine 3',5'-monophosphate increase cytosolic free $Ca^{2+}$ in rat pancreatic β-cells by enhancing $Ca^{2+}$ channel activity. *Endocrinology* 133: 1685–1692.

79. Zamponi et al. 1997. Crosstalk between G proteins and protein kinase C mediated by the calcium channel alpha 1 subunit. *Nature.* 385: 442–446.

80. Scharp et al. 1991. *Transplant.* 51: 76.

81. Warnock et al. 1991. *Diabetologia* 34: 55.

What is claimed is:

1. An isolated population of insulin-producing cells obtained from non-insulin-producing cells by a process comprising contacting the non-insulin-producing cells in vitro for at least twenty-four hours with an amount of a substance effective to induce insulin production, wherein the substance is selected from the group consisting of a GLP-1 peptide, a GLP-1 peptide containing one or more conservative amino acid substitutions at positions other than positions 7, 10, 12, 13 and 15 of GLP-1, and a fragment of any one of the preceding GLP-1 peptides, and wherein the GLP-1 peptide or fragment thereof has the ability to differentiate non-insulin-producing cells into insulin-producing cells.

2. The population of claim 1, wherein the non-insulin-producing cells comprise pancreatic cells.

3. The population of claim 1, wherein the non-insulin-producing cells comprise pancreatic acinar cells.

4. The population of claim 1, wherein the non-insulin-producing cells comprise stem cells.

5. The population of claim 1, wherein the non-insulin-producing cells comprise pancreatic stem cells.

6. The population of claim 1, wherein the non-insulin-producing cells comprise mammalian cells.

7. The population of claim 6, wherein the mammalian cells comprise human cells.

8. The composition of claim 1, wherein the contacting is at least 3 days.

9. The composition of claim 1, wherein the substance is a GLP-1 peptide.

10. The composition of claim 1, wherein the substance is a GLP-1 peptide containing one or more conservative amino acid substitutions at positions other than positions 7, 10, 12, 13 and 15 of GLP-1.

11. The composition of claim 1, wherein the substance is the fragment of a GLP-1 peptide, or a GLP-1 peptide containing one or more conservative amino acid substitutions at positions other than positions 7, 10, 12, 13 and 15 of GLP-1.

12. A method for differentiating non-insulin-producing cells into insulin-producing cells, comprising contacting the non-insulin-producing cells in vitro for at least twenty four hours with an amount of a substance effective to induce differentiation of non-insulin-producing cells into insulin-producing cells, wherein the substance is selected from the group consisting of a GLP-1 peptide, a GLP-1 peptide containing one or more conservative amino acid substitutions at positions other than positions 7, 10, 12, 13 and 15 of GLP-1, and a fragment of any one of the preceding GLP-1 peptides, and wherein the GLP-1 peptide or fragment thereof has the ability to differentiate non-insulin-producing cells into insulin-producing cells.

13. The method of claim 12, wherein the non-insulin-producing cells comprise pancreatic cells, pancreatic acinar cells, stem cells, pancreatic stem cells, or mammalian cells.

14. The method of claim 13, wherein the mammalian cells are human cells.

15. The method of claim 12, wherein the contacting is at least 3 days.

16. The method of claim 12, wherein the substance is a GLP-1 peptide.

17. The method of claims 12, wherein the substance is a GLP-1 peptide containing one or more conservative amino acid substitutions at positions other than positions 7, 10, 12, 13 and 15 of GLP-1.

18. The method of claims 12, wherein the substance is the fragment of a GLP-1 peptide, or a GLP-1 peptide containing one or more conservative amino acid substitutions at positions other than positions 7, 10, 12, 13 and 15 of GLP-1.

19. A method of enriching an isolated population of cells for insulin-producing cells, comprising contacting non-insulin-producing cells in vitro for at least twenty four hours with an amount of a substance effective to induce differentiation of non-insulin-producing cells into insulin-producing cells, wherein the substance is selected from the group consisting of a GLP-1 peptide, a GLP-1 peptide containing one or more conservative amino acid substitutions at positions other than positions 7, 10, 12, 13 and 15 of GLP-1, and a fragments of any one of the preceding peptides, and wherein the peptide or fragments thereof has the ability to differentiate non-insulin-producing cells into insulin-producing cells.

20. A method of promoting pancreatic amylase-producing cells to produce insulin, comprising contacting the pancreatic amylase-producing cells in vitro for at least twenty-four hours with an amount of a substance effective to induce insulin production, wherein the substance is selected from the group consisting of a GLP-1 peptide, a GLP-1 peptide containing one or more conservative amino acid substitutions at positions other than positions 7, 10, 12, 13 and 15 of GLP-1, and a fragment of any one of the preceding peptides, and wherein the GLP-1 peptide or fragment thereof has the ability to differentiate non-insulin-producing cells into insulin-producing cells.

21. An isolated population of insulin-producing cells obtained from non-insulin-producing cells by a process comprising contacting the non-insulin-producing cells in vitro for at least twenty-four hours with an amount of a substance effective to induce insulin production, wherein the substance is selected from the group consisting of an Exendin-4 peptide, an Exendin-4 peptide containing one or more conservative amino acid substitutions at positions other than positions 1, 4, 6, 7 and 9 of Exendin-4, and a fragment of any one of the preceding Exendin-4 peptides, and wherein the Exendin-4 peptide or fragment thereof has the ability to differentiate non-insulin-producing cells into insulin-producing cells.

22. The population of claim 21, wherein the non-insulin-producing cells comprise pancreatic cells.

23. The population of claim 21, wherein the non-insulin-producing cells comprise pancreatic acinar cells.

24. The population of claim 21, wherein the non-insulin-producing cells comprise stem cells.

25. The population of claim 21, wherein the non-insulin-producing cells comprise pancreatic stem cells.

26. The population of claim 21, wherein the non-insulin-producing cells comprise mammalian cells.

27. The population of claim 26, wherein the mammalian cells comprise human cells.

28. The composition of claim 21, wherein the contacting is at least 3 days.

29. The composition of claim 21, wherein the substance is exendin-4.

30. The composition of claim 21, wherein the substance is an Exendin-4 peptide containing one or more conservative amino acid substitutions at positions other than positions 1, 4, 6, 7 and 9 of Exendin-4.

31. The composition of claim 21, wherein the substance is the fragment of an Exendin-4 peptide, or an Exendin-4 peptide containing one or more conservative amino acid substitutions at positions other than 1, 4, 6, 7 and 9 of Exendin-4.

32. A method for differentiating non-insulin-producing cells into insulin-producing cells, comprising contacting the non-insulin-producing cells in vitro for at least twenty four hours with an amount of a substance effective to induce differentiation of non-insulin-producing cells into insulin-producing cells, wherein the substance is selected from the group consisting of an Exendin-4 peptide, an Exendin-4 peptide containing one or more conservative amino acid substitutions at positions other than positions 1, 4, 6, 7 and 9 of Exendin-4, and a fragment of any one of the preceding Exendin-4 peptides, and wherein the Exendin-4 peptide or fragment thereof has the ability to differentiate non-insulin-producing cells into insulin-producing cells.

33. The method of claim 32, wherein the non-insulin-producing cells comprise pancreatic cells, pancreatic acinar cells, stem cells, pancreatic stem cells, or mammalian cells.

34. The method of claim 33, wherein the mammalian cells are human cells.

35. The method of claim 32, wherein the contacting is at least 3 days.

36. The method of claim 32, wherein the substance is exendin-4.

37. The method of claim 32, wherein the substance is an Exendin-4 peptide containing one or more conservative amino acid substitutions at positions other than positions 1, 4, 6, 7 and 9 of Exendin-4.

38. The method of claims 32, wherein the substance is the fragment of an Exendin-4 peptide, or an Exendin-4 peptide containing one or more conservative amino acid substitutions at positions other than 1, 4, 6, 7 and 9 of Exendin-4.

39. A method of promoting pancreatic amylase-producing cells to produce insulin, comprising contacting the pancreatic amylase-producing cells in vitro for at least twenty-four hours with an amount of a substance effective to induce insulin production, wherein the substance is selected from the group consisting of an Exendin-4 peptide, an Exendin-4 peptide containing one or more conservative amino acid substitutions at positions other than 1, 4, 6, 7 and 9 of Exendin-4, and a fragment of any one of the preceding peptides, and wherein the Exendin-4 peptide or fragment thereof has the ability to differentiate non-insulin-producing cells into insulin-producing cells.

40. A method of enriching an isolated population of cells for insulin-producing cells, comprising contacting non-insulin-producing cells in vitro for at least twenty-four hours with an amount of a substance effective to induce differentiation of non-insulin-producing cells into insulin-producing cells, wherein the substance is selected from the group consisting of an Exendin-4 peptide, an Exendin-4 peptide containing one or more conservative amino acid substitutions at positions other than 1, 4, 6, 7 and 9 of Exendin-4, and a fragment of any one of the preceding peptides, and wherein the peptide or fragment thereof has the ability to differentiate non-insulin-producing cells into insulin-producing cells.

* * * * *

UNITED STATES PATENT AND TRADEMARK OFFICE
CERTIFICATE OF CORRECTION

PATENT NO.        : 7,056,734 B1
APPLICATION NO.   : 09/762538
DATED             : June 6, 2006
INVENTOR(S)       : Josephine Egan et al.

It is certified that error appears in the above-identified patent and that said Letters Patent is hereby corrected as shown below:

COL. 1, LN 13 INSERT

--The Government of the United States of America, as represented by the Secretary, Department of Health and Human Services, National Institutes of Health, Rockville, MD, and The General Hospital Corporation, Boston, MA--

TITLE PAGE, ITEM (56)
Other Publications:

Fehmann and Habener et al., the words "proisulin biosysthesis" should be replaced with --proinsulin biosynthesis--.

Goke et al., the word "exdenin" should be replaced with --exendin--.

Mashima et al., the word "insulin" should be replaced with --insulin--.

Montrose-Rafizdeh et al., the word "gluccagon" should be replaced with --glucagon--.

Nuack et al., the word "Gucagon" should be replaced with --Glucagon-- and the word "gastirc" should be replaced with --gastric--.

Nuack et al., the word "glluagoon" should be replaced with --glucagon--.

Perfetti et al., the word "insullin" should be replaced with --insulin--.

Ritzel et al., the word "Pharacokinetic" should be replaced with --Pharmacokinetic--.

Thorens et al., the word "Dempstration" should be replaced with --Demonstration--.

Wang et al., (pp 4910-4917) the word "stablity" should be replaced with --stability--.

UNITED STATES PATENT AND TRADEMARK OFFICE
CERTIFICATE OF CORRECTION

| | |
|---|---|
| PATENT NO. | : 7,056,734 B1 |
| APPLICATION NO. | : 09/762538 |
| DATED | : June 6, 2006 |
| INVENTOR(S) | : Josephine Egan et al. |

It is certified that error appears in the above-identified patent and that said Letters Patent is

TITLE PAGE, ITEM (56) OTHER PUBS.

Wang et al., (pp 417-421) the word "phsyiological" should be replaced with --physiological--.

Widmann et al., the word "phosporylation" should be replaced with --phosphorylation-- and the word "llike" should be replaced with --like--.

Willms et al., the word "exgenous" should be replaced with --exogenous--.

Yada et al., the word "cyosolic" should be replaced with --cytosolic--.

**TITLE PAGE, ITEM
(57) ABSTRACT** At line 6, the word "fragmets" should be replaced with --fragments--.

Column 5, line 19, the word "mmol/kg" should be replaced with --nmol/kg--.

Column 16, line 19 and 20, the word "intranimal" should be replaced with --intra-animal--

Column 16, line 63, the word "ans" should be replaced with --and--.

Column 20, line 4, the word "leads" should be replaced with --led--.

Column 26, line 26, the word "seqs" should be replaced with --secs--.

Column 29, line 58, the word "heptocyte" should be replaced with --hepatocyte--.

Column 31, line 10, the word "typsin" should be replaced with --trypsin--.

Column 35, line 9, the word "ridonuclease" should be replaced with --ribonuclease--.

UNITED STATES PATENT AND TRADEMARK OFFICE
CERTIFICATE OF CORRECTION

PATENT NO. : 7,056,734 B1
APPLICATION NO. : 09/762538
DATED : June 6, 2006
INVENTOR(S) : Josephine Egan et al.

It is certified that error appears in the above-identified patent and that said Letters Patent is hereby corrected as shown below:

Column 36, line 29, the word "hippocarnpus" should be replaced with --hippocampus--.

Signed and Sealed this

Fifth Day of December, 2006

JON W. DUDAS
*Director of the United States Patent and Trademark Office*